(12) United States Patent
Fletcher et al.

(10) Patent No.: US 11,760,752 B2
(45) Date of Patent: Sep. 19, 2023

(54) CARBOXYLIC ACID, ACYL SULFONAMIDE AND ACYL SULFAMIDE-DERIVATIZED BICYCLIC AZA-HETEROAROMATICS AS SELECTIVE MCL-1 INHIBITORS AND AS DUAL MCL-1/BCL-2 INHIBITORS

(71) Applicant: University of Maryland, Baltimore, Baltimore, MD (US)

(72) Inventors: Steven Fletcher, Baltimore, MD (US); Brandon Drennen, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/825,561

(22) Filed: Mar. 20, 2020

(65) Prior Publication Data
US 2020/0299285 A1    Sep. 24, 2020

Related U.S. Application Data

(60) Provisional application No. 62/821,482, filed on Mar. 21, 2019.

(51) Int. Cl.
| | |
|---|---|
| C07D 235/24 | (2006.01) |
| C07D 413/12 | (2006.01) |
| C07D 231/56 | (2006.01) |
| C07D 403/12 | (2006.01) |
| C07D 405/12 | (2006.01) |
| C07D 401/12 | (2006.01) |

(52) U.S. Cl.
CPC ......... *C07D 413/12* (2013.01); *C07D 231/56* (2013.01); *C07D 235/24* (2013.01); *C07D 401/12* (2013.01); *C07D 403/12* (2013.01); *C07D 405/12* (2013.01)

(58) Field of Classification Search
CPC .................................................. C07D 235/24
See application file for complete search history.

(56) References Cited

U.S. PATENT DOCUMENTS

2007/0043057 A1*  2/2007  Matteucci ............ C07D 209/44
                                                            514/252.04

OTHER PUBLICATIONS

Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Shamas-Din, A., Kale, J., Leber, B., and Andrews, D. W., "Mechanisms of Action of Bcl-2 Family Proteins." Cold Spring Harbor Perspectives in Biology, 2013, 5, 4, pp. 1-21.
Hanahan, D. and Weinberg, R. "Hallmarks of Cancer: The Next Generation." Cell 2011, 144, 5, pp. 646-674.
Gross, A., McDonnell, J.M., and Korsmeyer, S.J. "BCL-2 Family Members and the Mitochondria in Apoptosis." Genes & Development. 1999, 13, 15, pp. 1899-1911.
Ashkenazi, A., Fairbrother, W.J., Leverson, J. D., and Souers, A. J. "From Basic Apoptosis Discoveries to Advanced Selective BCL-2 Family Inhibitors." Nature Reviews Drug Discovery, 2017, 16, 4, pp. 273-284.
Delbridge, A. R. D., and Strasser, A. "The BCL-2 Protein Family, BH3-Mimetics and Cancer Therapy." Cell Death and Differentiation, 2015, 22, 7, pp. 1071-1080.
Tse, C., Shoemaker, A. R., Adickes, J., Anderson, M. G., et al. "ABT-263: A Potent and Orally Bioavailable Bcl-2 Family Inhibitor." Cancer Research, 2008, 68, 9, pp. 3421-3428.
Shoemaker, A. R., Mitten, M. J., Adickes, J., Oleksijew, A., Zhang, H., et al. "The Bcl-2 Family Inhibitor ABT-263 Shows Significant but Reversible Thrombocytopenia in Mice." Blood, 2006, 108, 11, p. 1107.
Souers, A. J., Leverson, J. D., Boghaert, E. R., Ackler, S. L., Catron, N. D., Chen, J., Dayton, B. D., et al. "ABT-199, a Potent and Selective BCL-2 Inhibitor, Achieves Antitumor Activity while Sparing Platelets." Nature Medicine, 2013, 19, 2, pp. 202-208.
"FDA approves Venetoclax in Combination for AML in Adults". U.S Food and Drug Administration, 2018. https://www.fda.gov/drugs/fda-approves-venetoclax-combination-aml-adults.
Tahir, S.K., Smith, M.L., Hessler, P., Rapp, L. R., Idler, K. B., Park, C. H., Leverson, J. D., and Lam, L. T. "Potential Mechanisms of Resistance to Venetoclax and Strategies to Circumvent it". BMC Cancer, 2017, 17, 399, pp. 1-10.
Xiang, W., Yang, C., and Bai, L. "MCL-1 Inhibition in Cancer Treatment." OncoTargets and Therapy, 2018, 11, pp. 7301-7314.
Tron, A. E., Belmonte, M. A., Adam, A., Aquila, B. M., Boise, L. H., Chiarparin, E., Cidado, J., et al. "Discovery of Mcl-1-Specific Inhibitor AZD5991 and Preclinical Activity in Multiple Myeloma and Acute Myeloid Leukemia." Nature Communications, 2018, 9, 1, pp. 1-14.
Caenepeel, S., Brown, S. P., Belmontes, B., Moody, G., Keegan, K. S., Chui, D., Whittington, D. A., et al. "AMG 176, a Selective MCL1 Inhibitor, Is Effective in Hematologic Cancer Models Alone and in Combination with Established Therapies." Cancer Discovery, 2018, 8, 12, pp. 1582-1597.
Ramsey, H. E., Fischer, M. A., Lee, T., Gorska, A. E., Arrate, M. P., Fuller, L., et al. "A Novel MCL-1 Inhibitor Combined with Venetoclax Rescues Venetoclax-Resistant Acute Myelogenous Leukemia." Cancer Discovery, 2018, 8, 12, pp. 1566-1581.
Prukova, D., Andrea, L., Nahacka, Z., Karolova, J., Svaton, M., Klanova, M., Havranek, O., et al. "Co-targeting of BCL-2 with Venetoclax and MCL-1 with S63845 is Synthetically Lethal In Vivo in Relapsed Mantle Cell Lymphoma." Clinical Cancer Research, 2019, 25, 14, pp. 4455-4465.
Anighoro, A., Bajorath, J., and Rastelli, G. "Polypharmacology: Challenges and Opportunities in Drug Discovery." Journal of Medicinal Chemistry, 2014, 57, pp. 7874-7887.
Antolin, A. A., Workman, P., Mestres, J., and Al-Lazikani, B. "Polypharmacology in Precision Oncology: Current Applications and Future Prospects." Current Pharmaceutical Design, 2016, 22, 46, pp. 6935-6945.

(Continued)

*Primary Examiner* — Shawquia Jackson
(74) *Attorney, Agent, or Firm* — Morgan, Lewis & Bockius LLP

(57) ABSTRACT

Mcl-1 selective inhibitors, Bcl-2 selective inhibitors, and Mcl-1/Bcl-2 dual inhibitors and methods of using the same for the treatment of disease are disclosed.

15 Claims, 1 Drawing Sheet

(56) References Cited

OTHER PUBLICATIONS

Friberg, A., Vigil, D., Zhao, B., Daniels, N. R., Burke, J. P., Garcia-Barrantes, P. M., et al. "Discovery of Potent Myeloid Cell Leukemia 1 (MCL-1) Inhibitors Using Fragment-Based Methods and Structure-Based Design." Journal of Medicinal Chemistry, 2013, 56, pp. 15-30.

Lee, E. F., Czabotar, P. E., Smith, B. J., Deshayes, K., Zobel, K., Colman, P. M., and Fairlie, W. D. "Crystal Structure of ABT-737 Complexed with BCL-XL: Implications for Selectivity of Antagonists of the Bcl-2 Family." Cell Death & Differentiation, 2007, 14, pp. 1711-1713.

Longwoth, M., Banister, S. D., Mack, J. B. C., Glass, M., Connor, M., and Kassiou, M. "The 2-Alkyl-2H-Indazole Regioisomers of Synthetic Cannabinoids Ab-Chminaca, Ab-Fubinaca, Ab-Pinaca, and 5F-AB-PINACA are Possible Manufacturing Impurities with Cannabimimetic Activities." Forensic Toxicology, 2016, 34, pp. 286-303.

Cheung, M., Boloor, A., and Stafford, J. A. "Efficient and Regioselective Synthesis of 2-Alkyl-2H-Indazoles." Journal of Organic Chemistry, 2003, 68, 10, pp. 4093-4095.

Kotschy, A., Szlavik, Z., Murray, J., Davidson, J., Maragno, A. L., Toumelin-Braizat, G., Chanrion, M., et al. "The MCL1 Inhibitor S63845 Is Tolerable and Effective in Diverse Cancer Models." Nature, 2016, 538, 7626, pp. 477-482.

Hird, A. W., and Tron, A. E. "Recent Advances in the Development of MCL-1 Inhibitors for Cancer Therapy." Pharmacology & Therapeutics, 2019, 198, pp. 59-67.

Song et al. "Substituted indole Mcl-1 inhibitors: a patent evaluation (WO2015148854A1)" Expert Opinion on Therapeutic Patents, Epub Oct. 4, 2016; 26(11): pp. 1227-1238.

Pelz et al. "Discovery of 2-Indole-acylsulfonamide Myeloid Cell Leukemia 1 (Mcl-1) Inhibitors Using Fragment-Based Methods" J Med Chem Mar. 10, 2016; 59(5): pp. 2054-5066.

Wang et al. "Fragment-Based Design, Synthesis, and Biological Evaluation of 1-Substituted-indole-2-carboxylic Acids as Selective Mcl-1 Inhibitors" Arch. Pharm. Chem. Life Sci. 2017, 350, e1600251: pp. 1-12.

Xu et al., "1-Phenyl-1H-indole derivatives as a new class of Bcl-2/Mcl-1 dual inhibitors: Design, synthesis, and preliminary biological evaluation," Bioorg Med Chem Oct. 15, 2017;25(20):5548-5556.

Liu et al. "Design, synthesis and preliminary biological evaluation of indole-carboxylic acid-based skeleton of Bcl-2/Mcl-1 dual inhibitors" Bioorganic & Medicinal Chemistry 25 92017): pp. 1939-1948.

Shenglin Luan et al. "Discovery and structure-activity relationship studies of N-substituted indole derivatives as novel Mcl-1 inhibitors" Bioorganic & Medicinal Chemistry Letters 27 (2017): pp. 1943-1948.

Anders Friberg et al. "Discovery of potent myeloid cell leukemia 1 (Mcl 1) Inhibitors using fragment based methods and structure based design" J Med Chem. Jan. 10, 2013; 56(1): pp. 15-30.

* cited by examiner

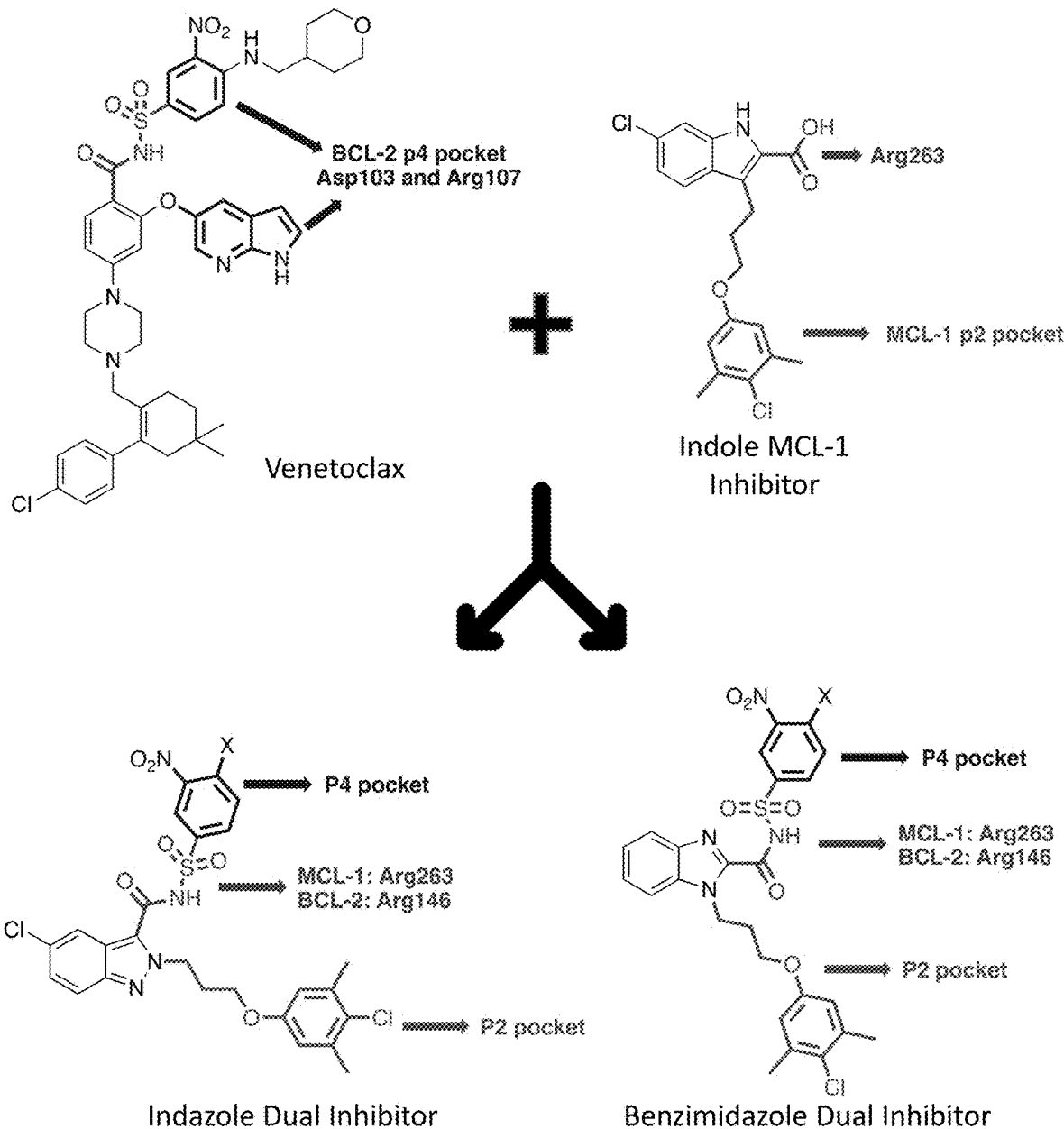

CARBOXYLIC ACID, ACYL SULFONAMIDE AND ACYL SULFAMIDE-DERIVATIZED BICYCLIC AZA-HETEROAROMATICS AS SELECTIVE MCL-1 INHIBITORS AND AS DUAL MCL-1/BCL-2 INHIBITORS

CROSS-REFERENCE TO RELATED APPLICATION

This application is a U.S. Nonprovisional application which claims the benefit of U.S. Provisional Patent Applications No. 62/821,482, filed Mar. 21, 2019, which is incorporated by reference herein in its entirety.

FIELD OF THE INVENTION

The invention relates generally to compounds and methods of using the same for treating conditions characterized by the overexpression or upregulated activity of Myeloid Cell Leukemia-1 (Mcl-1) family proteins, and/or B-Cell Lymphoma-2 (Bcl-2) family of proteins, and more particularly, but not exclusively, to compounds and methods of using the same that bind both Mcl-1 and Bcl-2 oncoproteins.

BACKGROUND OF THE INVENTION

Apoptosis, or programmed cell death, is initiated when cells have sustained irreparable damage or developed detrimental mutations. The intrinsic apoptosis pathway is regulated by the B-cell lymphoma 2 (BCL-2) family of proteins, which contains both pro-apoptotic (e.g. BAK, BAX, BIM and NOXA) and anti-apoptotic (e.g. BCL-2, BCL-XL and MCL-1) members. These proteins regulate apoptosis through a protein-protein interaction between the pro-apoptotic and anti-apoptotic members. Under apoptotic conditions, the interaction is disrupted by displacement of the pro-apoptotic proteins by BH3-only proteins, initiating apoptosis. Unfortunately, cancerous cells upregulate the expression of the anti-apoptotic proteins to capture the BH3-only proteins before displacement can occur, thus inhibiting apoptosis.

A current strategy deployed to combat this protein imbalance are BH3 mimics, small molecules that can mimic the pro-apoptotic protein's α-helical BH3 binding domain. BH3 mimetics act by releasing both the native activator and effector proteins, ultimately restoring apoptosis regulation. However, BH3 mimetics possess significant drawbacks. The dual BCL-2/BCL-$X_L$ inhibitor ABT-263 (Navitoclax) induces thrombocytopenia due to its inhibition of BCL-$X_L$, which platelets require to survive. FDA approved ABT-199 (Venetoclax) was later synthesized to remedy the thrombocytopenia toxicity through increased selectivity for BCL-2, but has been reported to increase MCL-1 expression within cancerous cells, mitigating its efficacy.

Mcl-1 overexpression and/or amplification of the Mcl-1 gene immortalizes cells, and has been observed in many human solid tumors, including pancreatic, prostate, cervical, lung and breast cancers, as well as B-cell lymphomas and hematological cancers, including acute myeloid leukemia (AML). The B-Cell Lymphoma-2 (Bcl-2) family of proteins regulates the intrinsic apoptosis pathway that is responsible for programmed cell death. The pathway involves protein-protein interactions (PPIs) between pro-apoptotic members of the Bcl-2 family, such as Bim, Bak and Bad, and anti-apoptotic members, such as Bcl-xL and myeloid cell leukemia-1 (Mcl-1). Through conserved hydrophobic crevices, the anti-apoptotic Bcl-2 proteins capture the BH3 α-helical domains of their pro-apoptotic counterparts, effectively "neutralizing" their cell killing functions. Evasion of apoptosis is a hallmark of cancer, and is also one culprit for the development of resistance to current chemo- and radiotherapies. While certain Bcl-$_{xL}$/Bcl-2 inhibitors perform well in clinical trials, their low affinity for Mcl-1 is a contributing factor to the observed resistance of several tumor cell lines. Moreover, the upregulation of Mcl-1 has been directly linked to the reduced efficacy of several FDA-approved anti-cancer chemotherapies.

SUMMARY OF THE INVENTION

The disclosure provides in one aspect a compound of formula (I), formula (II), formula (III), formula (IV), formula (V), formula (VI), or formula (VII), or a pharmaceutically acceptable salt, solvate, hydrate, cocrystal, or prodrug thereof:

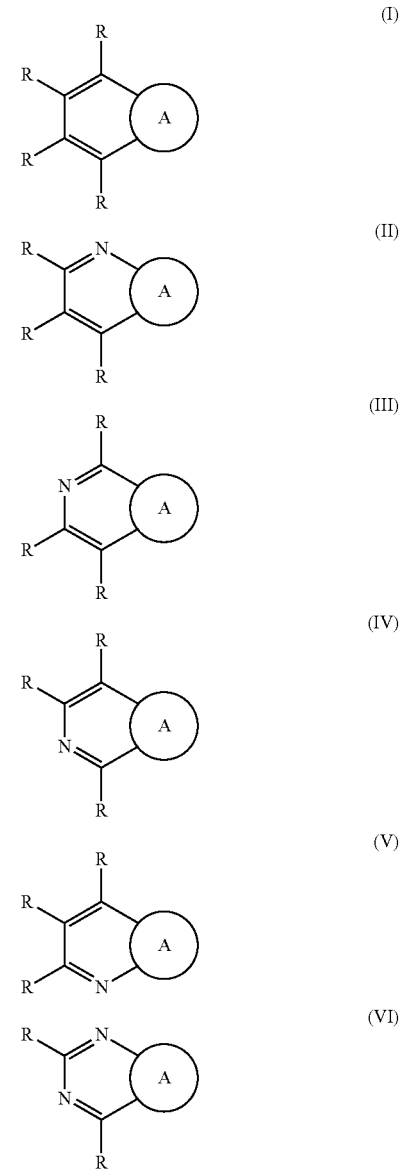

-continued

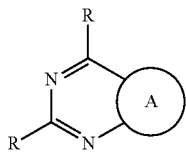
(VII)

wherein:

A is a substituted heterocycle selected from:

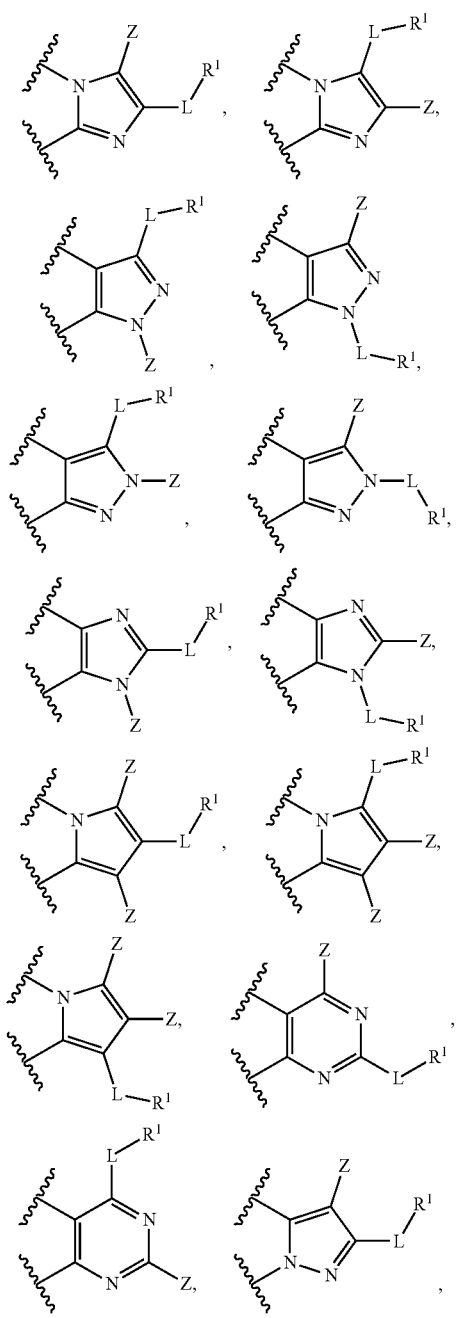

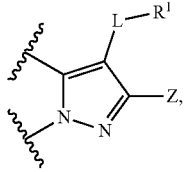

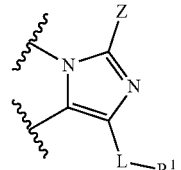

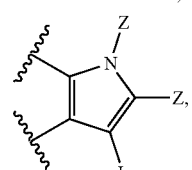

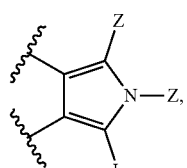

L is selected from —C(O)O—, —OC(O)—, —C(O)NR$^a$—, —NR$^a$C(O)—, —C(O)NR$^a$SO$_2$—, —SO$_2$NR$^a$C(O)—, —C(O)NR$^a$SO$_2$NR$^a$—, and —NR$^a$SO$_2$NR$^a$C(O)—; and R, R$^1$, R$^a$, and Z are independently selected at each occurrence from H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl.

In some embodiments, L is selected from —C(O)O—, —C(O)NHSO$_2$—, and —C(O)NHSO$_2$NH—. In some embodiments, R$^1$ is selected from H, alkyl, and substituted aryl. In some embodiments, R$^1$ is selected from H, methyl, and a substituted phenyl having one or more substituents selected from halogen, nitro, and optionally substituted amino. In some embodiments, Z is independently selected from H, Cl, F, Br, —CH$_2$R$^b$, —CH$_2$CH$_2$R$^b$, —CH$_2$CH$_2$CH$_2$R$^b$, and —C≡CR$^b$, wherein R$^b$ is selected from optionally substituted alkyl, optionally substituted cycloalkyl, optionally substituted aryl, and optionally substituted heteroaryl. In some embodiments, Z includes at least one of H, Cl, a —CH$_2$— group, and —C≡C— group, a substituted phenyl, a nitro group, an ether moiety, and a heterocycle. In some embodiments, a heterocycle is selected from a morpholinyl group, a thiomorpholinyl group, a pyridine group, a furanyl group, a tetrahydrofuranyl group, a piperidine group, and a piperazine group.

In some embodiments, the compound of formula (I), formula (II), formula (III), formula (IV), formula (V), formula (VI), or formula (VII), or a pharmaceutically acceptable salt, solvate, hydrate, cocrystal, or prodrug thereof, is selected from Table 1. In some embodiments, the compound of formula (I), formula (II), formula (III), formula (IV), formula (V), formula (VI), or formula (VII), or a pharmaceutically acceptable salt, solvate, hydrate, cocrystal, or prodrug thereof, is selected from Table 1 and R is independently selected from H, a halogen, and —COCH₃. In some embodiments, the compound of formula (I), formula (II), formula (III), formula (IV), formula (V), formula (VI), or formula (VII), or a pharmaceutically acceptable salt, solvate, hydrate, cocrystal, or prodrug thereof, is selected from Table 1 and Z is independently selected from H, halogen, optionally substituted alkyl, optionally substituted cycloalkyl, optionally substituted aralkyl, and optionally substituted heteroaryl. In some embodiments, compound of formula (I), formula (II), formula (III), formula (IV), formula (V), formula (VI), or formula (VII), or a pharmaceutically acceptable salt, solvate, hydrate, cocrystal, or prodrug thereof, is selected from Table 1 and Z is independently selected from:

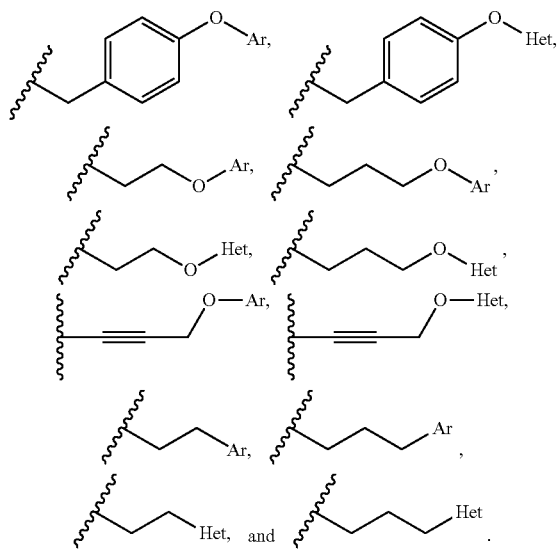

In some embodiments, Ar is an optionally substituted phenyl group, and Het is an optionally substituted heterocycle. In some embodiments, Ar is

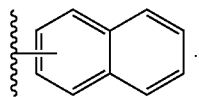

In some embodiments, Ar is

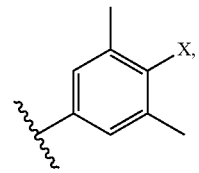

wherein X is a halogen. In some embodiments, X is Cl. In some embodiments, a halogen is Cl. In some embodiments, Het is N-morpholinyl. In some embodiments, the compound of formula (I) is selected from Table 2.

The disclosure provides in another aspect a pharmaceutical composition for treating a condition alleviated by selectively inhibiting Mcl-1 protein activity, the pharmaceutical composition comprising one or more compounds described herein, or a pharmaceutically acceptable salt, solvate, hydrate, cocrystal, or prodrug thereof, and a pharmaceutically acceptable carrier. In some embodiments, the disclosure provides a pharmaceutical composition for treating a condition alleviated by selectively inhibiting Bcl-2 protein activity, the pharmaceutical composition comprising one or more compounds described herein, or a pharmaceutically acceptable salt, solvate, hydrate, cocrystal, or prodrug thereof, and a pharmaceutically acceptable carrier. In some embodiments, the disclosure provides a pharmaceutical composition for treating a condition alleviated by dual inhibition of Mcl-1 protein and Bcl-2 protein activity, the pharmaceutical composition comprising one or more compounds described herein, or a pharmaceutically acceptable salt, solvate, hydrate, cocrystal, or prodrug thereof, and a pharmaceutically acceptable carrier. In some embodiments, compounds described herein include, but are not limited to, the following compounds, or a pharmaceutically acceptable salt, solvate, hydrate, cocrystal, or prodrug thereof: compounds of formula (I), formula (II), formula (III), formula (IV), formula (V), formula (VI), or formula (VII), and their features and limitations as described herein; compounds of formulas 5, 9-12, 31-52, 1001-1153, and 2001-2008, and their features and limitations as described herein; compounds NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, and their features and limitations as described herein. In some embodiments, the pharmaceutical compositions described herein are for treating pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, myeloid leukemia, acute myeloid leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

The disclosure also provides a method of treating a condition by selectively inhibiting Mcl-1 protein activity in a patient in need of said treatment, the method comprising administering to the patient a therapeutically effective amount of one or more compounds described herein, or a pharmaceutically acceptable salt, solvate, hydrate, cocrystal, or prodrug thereof. In some embodiments, the disclosure provides a method of treating a condition by selectively inhibiting Bcl-2 protein activity in a patient in need of said treatment, the method comprising administering to the patient a therapeutically effective amount of one or more compounds described herein, or a pharmaceutically acceptable salt, solvate, hydrate, cocrystal, or prodrug thereof. In some embodiments, the disclosure provides a method of treating a condition by dual inhibition of Mcl-1 protein activity and Bcl-2 protein activity in a patient in need of said treatment, the method comprising administering to the patient a therapeutically effective amount of one or more compounds described herein, or a pharmaceutically acceptable salt, solvate, hydrate, cocrystal, or prodrug thereof. In some embodiments, compounds described herein include, but are not limited to, the following compounds, or a pharmaceutically acceptable salt, solvate, hydrate, cocrystal, or prodrug thereof: compounds of formula (I), formula (II), formula (III), formula (IV), formula (V), formula (VI), or formula (VII), and their features and limitations as described herein; compounds of formulas 5, 9-12, 31-52, 1001-1153, and 2001-2008, and their features and limitations as described herein; compounds NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, and their features and limitations as described herein. In some embodiments, the condition is selected from pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, myeloid leukemia, acute myeloid leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

BRIEF DESCRIPTION OF THE FIGURES

FIG. 1 illustrates the overall design for dual-selective BCL-2 and MCL-1 inhibitors as adapted from previously identified selective inhibitors.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The terms "active pharmaceutical ingredient" and "drug" include, but are not limited to, the compounds described herein and, more specifically: compounds of formula (I), formula (II), formula (III), formula (IV), formula (V), formula (VI), or formula (VII), and their features and limitations as described herein; compounds of formulas 5, 9-12, 31-52, 1001-1153, and 2001-2008, and their features and limitations as described herein; compounds NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, and their features and limitations as described herein. The terms "active pharmaceutical ingredient" and "drug" may also include those compounds described herein that bind Mcl-1 and/or Bcl-2 protein, and thereby modulate Mcl-1 and/or Bcl-2 protein activity, selectively bind Mcl-1, selectively bind Bcl-2, or dually bind Mcl-1 and Bcl-2.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., increased sensitivity to apoptosis). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs disclosed herein, can also be incorporated into the described compositions and methods.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition).

As used herein, the terms "modulate" and "modulation" refer to a change in biological activity for a biological molecule (e.g., a protein, gene, peptide, antibody, and the like), where such change may relate to an increase in biological activity (e.g., increased activity, agonism, activation, expression, upregulation, and/or increased expression) or decrease in biological activity (e.g., decreased activity, antagonism, suppression, deactivation, downregulation, and/or decreased expression) for the biological molecule. In some embodiments, the biological molecules modulated by the methods and compounds of the invention to effect treatment may include the Mcl-1 oncoprotein and Bcl-2 oncoprotein.

As used herein, the term "prodrug" refers to a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of a compound of formula (I), formula (II), formula (III), formula (IV), formula (V), formula (VI), or formula (VII), or formula 5, 9-12, 31-52, 1001-1153, and 2001-2008, or formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., a compound of formula (I), formula (II), formula (III), formula (IV), formula (V), formula (VI), or formula (VII); a compound of any of formulas 5, 9-12, 31-52, 1001-1153, and 2001-2008; or any of compounds NB-1-070, NB-1-084, NB-1-086, NB-1-087, NB-1-088, NB-1-089, CG-1-016, CG-1-018, CG-1-019, CG-1-022, CG-1-

023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b) is a prodrug within the scope of the invention. Various forms of prodrugs are well known in the art. A comprehensive description of pro drugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g. organ or tumor-targeting, lymphocyte targeting), to modify or improve aqueous solubility of a drug (e.g., i.v. preparations and eyedrops), to improve topical drug delivery (e.g. dermal and ocular drug delivery), to improve the chemical/enzymatic stability of a drug, or to decrease off-target drug effects, and more generally in order to improve the therapeutic efficacy of the compounds utilized in the invention.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}C$- or $^{14}C$-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., ($C_{1-10}$)alkyl or $C_{1-10}$alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N-$R^a$)N($R^a$)$_2$, —N($R^a$)S(O)$_t R^a$ (where t is 1 or 2), —S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$ where each $R^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocyclyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., ($C_{2-10}$)alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t R^a$ (where t is 1 or 2), —S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., ($C_{2-10}$)alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C═O)H radical.

"Carboxyl" refers to a —(C═O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_{3-10}$)cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a ($C_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acylsulfonamide" refers a —S(O)$_2$—N(R$^a$)—C(=O)— radical, where R$^a$ is hydrogen, alkyl, fluoroalkyl, carbocyclyl, carbocyclylalkyl, aryl, aralkyl, heterocycloalkyl, heterocycloalkylalkyl, heteroaryl or heteroarylalkyl. Unless stated otherwise specifically in the specification, an acylsulfonamide group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl "Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^a$, and NR$^a$R$^a$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)

$_tR^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "aryloxy" refers to the group —O-aryl.

The term "substituted aryloxy" refers to aryloxy wherein the aryl substituent is substituted (i.e., —O-(substituted aryl)). Unless stated otherwise specifically in the specification, the aryl moiety of an aryloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., C$_1$-C$_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" or "Het" refers to a 5- to 18-membered aromatic radical (e.g., C$_5$-C$_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolin yl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —NO$_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S($O_2$)—H, —S($O_2$)-(optionally substituted alkyl), —S($O_2$)-(optionally substituted amino), —S($O_2$)-(optionally substituted aryl), —S($O_2$)-(optionally substituted heteroaryl), and —S($O_2$)-(optionally substituted heterocycloalkyl).

"Sulfonamidyl" or "sulfonamido" refers to a —S($=O$)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S($=O$)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All embodiments of the invention can, in the alternative, be more specifically defined by any of the transitional terms "comprising," "consisting essentially of," and "consisting of."

Selective Mcl-1 Inhibitors, Selective Bcl-2 Inhibitors, and Dual Mcl-1/Bcl-2 Inhibitors In an embodiment, the invention includes compounds that are selective inhibitors of Mcl-1 oncoprotein. In an embodiment, the invention includes compounds that are selective inhibitors of Bcl-2 oncoprotein. In an embodiment, the invention includes compounds that are dual inhibitors of Mcl-1 and Bcl-2 oncoproteins. As described herein, apoptosis, or programmed cell death, is controlled by the B-cell lymphoma 2 (BCL-2) family of cellular proteins, which contains both pro-apoptotic (e.g., BAK, BAX, BIM and NOXA) and anti-apoptotic (e.g., BCL-2, BCL-X$_L$ and MCL-1) members. The pro-apoptotic members can be further divided into the BCL-2 effectors (BAK, BAX), multi-BH domain proteins located within the mitochondria membrane, and the BH3-only activators (BID, NOXA), proteins that solely express the α-helical BH3 domain of the effector proteins. Under homeostatic conditions, the effector proteins' α-helical BH3 domain interacts with the hydrophobic binding groove on the surface of the anti-apoptotic proteins, capturing the effector proteins and blocking apoptosis. Once a cell is exposed to apoptotic stress, it expresses the BH3-only activator proteins which release the effector proteins from sequestration to initiate apoptosis. Various human cancers exploit this pathway by upregulating the expression of the anti-apoptotic proteins, resulting in the capture of the BH3-only proteins before they can release the effector proteins, thus inhibiting apoptosis. A current strategy deployed to combat this oncogenic transformation is BH3 mimicry, which is the development of small molecules that can mimic the α-helical BH3 domain and thereby free up the native BH3-only proteins to initiate apoptosis. BH3 mimetics have shown promising activity in clinical studies. Indeed, ABT-199, a selective BH3 mimetic for BCL-2, has recently been approved by the FDA for chronic lymphocytic leukemia. For example, see U.S. Pat. No. 9,539,251, the entirety of which is incorporated herein by reference. Unfortunately, resistance has been observed in cancer cells exposed to ABT-199, manifested by the upregulation of MCL-1 as a compensatory mechanism to counter BCL-2 inhibition.

In some embodiments, the compounds described herein may decrease the activity of Mcl-1 protein. In some embodiments, the compounds described herein may decrease the activity of Bcl-2 protein. In some embodiments, the compounds described herein may decrease the activity of Mcl-1 protein and Bcl-2 protein. In some embodiments, the compounds described herein may be delivered as a listed or as a pharmaceutically acceptable salt, solvate, hydrate, cocrystal, tautomer, or prodrug thereof The disclosure provides in one aspect a compound of formula (I), formula (II), formula (III), formula (IV), formula (V), formula (VI), or formula (VII), or a pharmaceutically acceptable salt, solvate, hydrate, cocrystal, or prodrug thereof:

wherein:

A is a substituted heterocycle selected from:

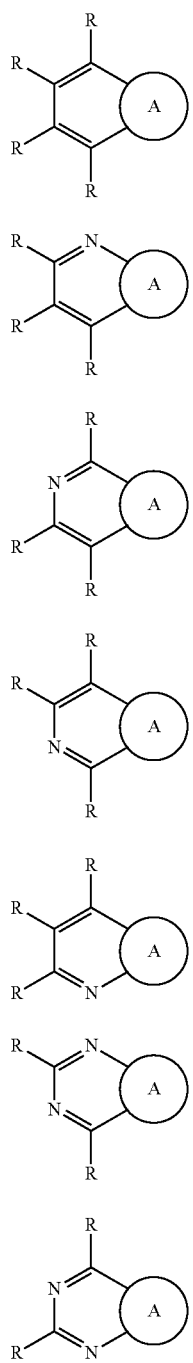

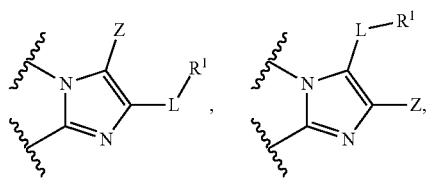

L is selected from —C(O)O—, —OC(O)—, —C(O)NR$^a$—, —NR$^a$C(O)—, —C(O)NR$^a$SO$_2$—, —SO$_2$NR$^a$C(O)—, —C(O)NR$^a$SO$_2$NR$^a$—, and —NR$^a$SO$_2$NR$^a$C(O)—; and R, R$^1$, R$^a$, and Z are independently selected at each occurrence from H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl. In some embodiments, A is a substituted heterocycle selected from:

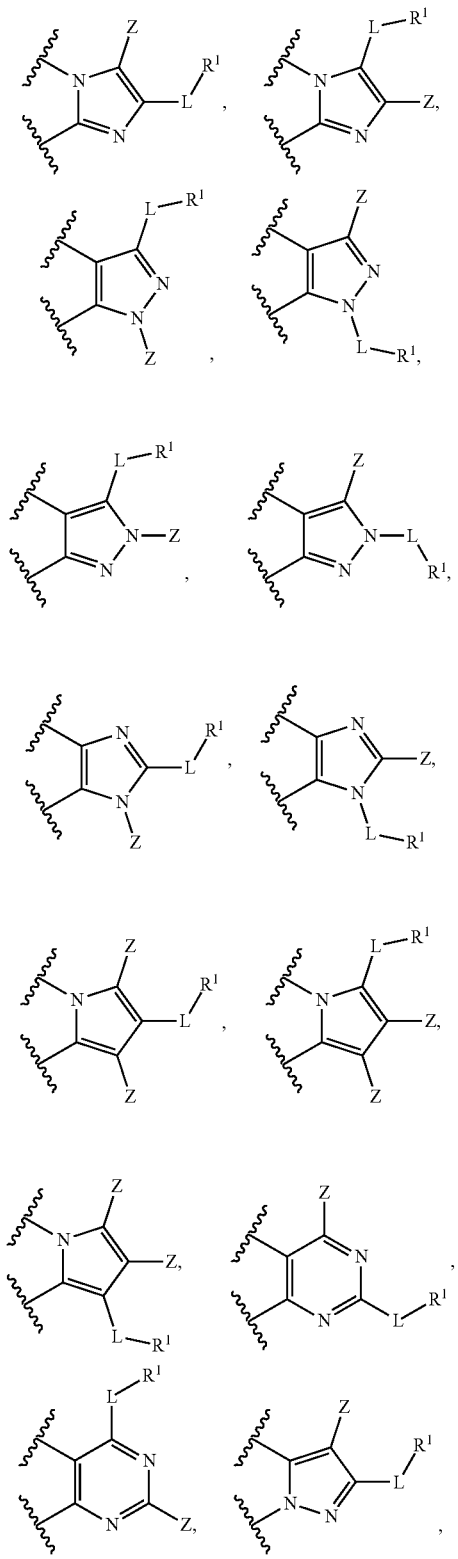

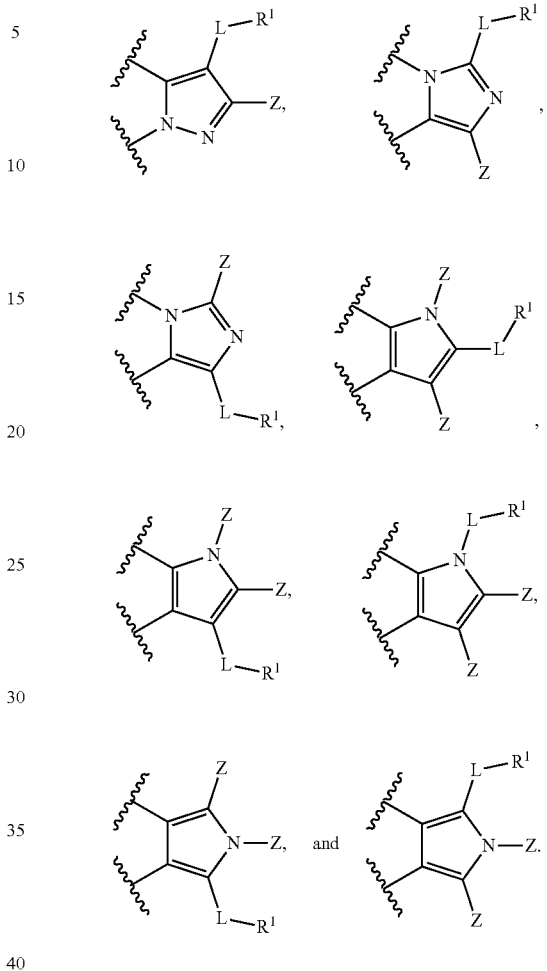

Any suitable L group can be used, as apparent to one skilled in the art. In some embodiments, L is selected from —C(O)O—, —OC(O)—, —C(O)NH—, —NHC(O)—, —C(O)NHSO₂—, —SO₂NHC(O)—, —C(O)NHSO₂NH—, and —NHSO₂NHC(O)—; In some embodiments, L is selected from —C(O)O—, —C(O)NHSO₂—, and —C(O)NHSO₂NH—. In some embodiments, R¹ is selected from H, alkyl, and substituted aryl. In some embodiments, R¹ is selected from H, methyl, and a substituted phenyl having one or more substituents selected from halogen, nitro, and optionally substituted amino. In some embodiments, Z is independently selected from H, CL, F, Br, —CH₂Rᵇ, —CH₂CH₂Rᵇ, —CH₂CH₂CH₂Rᵇ, and —C≡CRᵇ, wherein Rᵇ is selected from optionally substituted alkyl, optionally substituted cycloalkyl, optionally substituted aryl, and optionally substituted heteroaryl. In some embodiments, Z includes at least one of H, CL, a —CH₂— group, and —C≡C— group, a substituted phenyl, a nitro group, an ether moiety, and a heterocycle. In some embodiments, a heterocycle is selected from a morpholinyl group, a thiomorpholinyl group, a pyridine group, a furanyl group, a tetrahydrofuranyl group, a piperidine group, and a piperazine group.

In some embodiments, the compound of formula (I), formula (II), formula (III), formula (IV), formula (V), formula (VI), or formula (VII), or a pharmaceutically acceptable salt, solvate, hydrate, cocrystal, or prodrug thereof, is selected from Table 1:

TABLE 1

| Compound # | A | L | R¹ |
|---|---|---|---|
| 1001 | (imidazole with Z on N, L-R¹ on C) | —C(O)O— | H |
| 1002 | (pyrazole with L-R¹ on C3, Z on N1) | —C(O)O— | H |
| 1003 | (imidazole with Z on N, L-R¹ on C2) | —C(O)O— | H |
| 1004 | (pyrrole with Z on N, L-R¹ on C, Z substituent) | —C(O)O— | H |
| 1005 | (pyrimidine with Z, L-R¹) | —C(O)O— | H |
| 1006 | (pyrazole with Z, L-R¹) | —C(O)O— | H |
| 1007 | (imidazole with Z on N, L-R¹ on C) | —C(O)NHSO₂— | 4-chlorophenyl |
| 1008 | (pyrazole with L-R¹ on C3, Z on N1) | —C(O)NHSO₂— | 4-chlorophenyl |

TABLE 1-continued

| Compound # | A | L | R¹ |
|---|---|---|---|
| 1009 | imidazole with Z on N, L-R¹ on C2 | —C(O)NHSO₂— | 4-chlorophenyl |
| 1010 | pyrrole with Z on N and ring carbon, L-R¹ on C | —C(O)NHSO₂— | 4-chlorophenyl |
| 1011 | pyrimidine with Z, L-R¹ on C2 | —C(O)NHSO₂— | 4-chlorophenyl |
| 1012 | pyrazole with Z, L-R¹ | —C(O)NHSO₂— | 4-chlorophenyl |
| 1013 | imidazole with Z on N, L-R¹ on C | —C(O)NHSO₂— | 4-morpholino-3-nitrophenyl |
| 1014 | pyrazole with Z on N, L-R¹ on C3 | —C(O)NHSO₂— | 4-morpholino-3-nitrophenyl |
| 1015 | imidazole with Z on N, L-R¹ on C2 | —C(O)NHSO₂— | 4-morpholino-3-nitrophenyl |
| 1016 | pyrrole with Z on N and ring carbon, L-R¹ on C | —C(O)NHSO₂— | 4-morpholino-3-nitrophenyl |

TABLE 1-continued

| Compound # | A | L | R¹ |
|---|---|---|---|
| 1017 | pyrimidine with Z, L-R¹ | —C(O)NHSO₂— | 4-morpholino-3-nitrophenyl |
| 1018 | pyrazole with Z, L-R¹ | —C(O)NHSO₂— | 4-morpholino-3-nitrophenyl |
| 1019 | imidazole with Z, L-R¹ | —C(O)NHSO₂— | 3-nitro-4-((pyridin-3-ylmethyl)amino)phenyl |
| 1020 | pyrazole with L-R¹, Z | —C(O)NHSO₂— | 3-nitro-4-((pyridin-3-ylmethyl)amino)phenyl |
| 1021 | imidazole with L-R¹, Z | —C(O)NHSO₂— | 3-nitro-4-((pyridin-3-ylmethyl)amino)phenyl |
| 1022 | pyrrole with Z, L-R¹, Z | —C(O)NHSO₂— | 3-nitro-4-((pyridin-3-ylmethyl)amino)phenyl |
| 1023 | pyrimidine with Z, L-R¹ | —C(O)NHSO₂— | 3-nitro-4-((pyridin-3-ylmethyl)amino)phenyl |

TABLE 1-continued

| Compound # | A | L | R¹ |
|---|---|---|---|
| 1024 | pyrazole with Z, L-R¹ substituents | —C(O)NHSO₂— | 2-NO₂-phenyl-NH-CH₂-(pyridin-3-yl) |
| 1025 | imidazole with Z, L-R¹ substituents | —C(O)NHSO₂— | 2-NO₂-phenyl-NH-CH₂CH₂-morpholine |
| 1026 | pyrazole with L-R¹, Z substituents | —C(O)NHSO₂— | 2-NO₂-phenyl-NH-CH₂CH₂-morpholine |
| 1027 | imidazole with L-R¹, Z substituents | —C(O)NHSO₂— | 2-NO₂-phenyl-NH-CH₂CH₂-morpholine |
| 1028 | pyrrole with Z, L-R¹, Z substituents | —C(O)NHSO₂— | 2-NO₂-phenyl-NH-CH₂CH₂-morpholine |
| 1029 | pyrimidine with Z, L-R¹ substituents | —C(O)NHSO₂— | 2-NO₂-phenyl-NH-CH₂CH₂-morpholine |
| 1030 | pyrazole with Z, L-R¹ substituents | —C(O)NHSO₂— | 2-NO₂-phenyl-NH-CH₂CH₂-morpholine |
| 1031 | imidazole with Z, L-R¹ substituents | —C(O)NHSO₂— | 2-NO₂-phenyl-NH-CH₂-(furan-2-yl) |

TABLE 1-continued

| Compound # | A | L | R¹ |
|---|---|---|---|
| 1032 | pyrazole (L-R¹ at 3, Z at 1 and 5) | —C(O)NHSO₂— | 2-nitro-4-[(furan-2-ylmethyl)amino]phenyl |
| 1033 | imidazole (L-R¹ at 2, Z at 1 and 4/5) | —C(O)NHSO₂— | 2-nitro-4-[(furan-2-ylmethyl)amino]phenyl |
| 1034 | pyrrole (Z at 1 and 2/5, L-R¹ at 3/4) | —C(O)NHSO₂— | 2-nitro-4-[(furan-2-ylmethyl)amino]phenyl |
| 1035 | pyrimidine (Z at 5, L-R¹ at 2) | —C(O)NHSO₂— | 2-nitro-4-[(furan-2-ylmethyl)amino]phenyl |
| 1036 | pyrazole (Z at 1 and 5, L-R¹ at 3) | —C(O)NHSO₂— | 2-nitro-4-[(furan-2-ylmethyl)amino]phenyl |
| 1037 | imidazole (Z at 1 and 5, L-R¹ at 4) | —C(O)NHSO₂— | 2-nitro-5-(morpholin-4-yl)phenyl |
| 1038 | pyrazole (L-R¹ at 3, Z at 1 and 5) | —C(O)NHSO₂— | 2-nitro-5-(morpholin-4-yl)phenyl |
| 1039 | imidazole (L-R¹ at 2, Z at 1 and 4/5) | —C(O)NHSO₂— | 2-nitro-5-(morpholin-4-yl)phenyl |

TABLE 1-continued

| Compound # | A | L | R¹ |
|---|---|---|---|
| 1040 | pyrrole with Z, Z, R¹-L substituents | —C(O)NHSO₂— | 4-nitro-3-morpholinophenyl |
| 1041 | pyrimidine with Z, L-R¹ | —C(O)NHSO₂— | 4-nitro-3-morpholinophenyl |
| 1042 | pyrazole with Z, L-R¹ | —C(O)NHSO₂— | 4-nitro-3-morpholinophenyl |
| 1043 | imidazole with Z, L-R¹ | —C(O)NHSO₂— | 4-nitro-3-((pyridin-3-ylmethyl)amino)phenyl |
| 1044 | pyrazole with L-R¹, Z | —C(O)NHSO₂— | 4-nitro-3-((pyridin-3-ylmethyl)amino)phenyl |
| 1045 | imidazole with Z, L-R¹ | —C(O)NHSO₂— | 4-nitro-3-((pyridin-3-ylmethyl)amino)phenyl |
| 1046 | pyrrole with Z, Z, L-R¹ | —C(O)NHSO₂— | 4-nitro-3-((pyridin-3-ylmethyl)amino)phenyl |
| 1047 | pyrimidine with Z, L-R¹ | —C(O)NHSO₂— | 4-nitro-3-((pyridin-3-ylmethyl)amino)phenyl |

TABLE 1-continued
| Compound # | A | L | R¹ |
|---|---|---|---|
| 1048 | 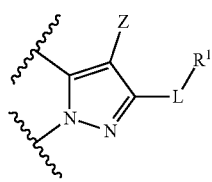 | —C(O)NHSO₂— | 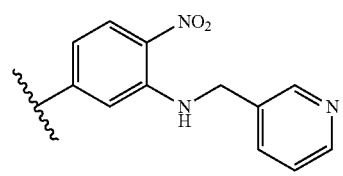 [SMILES: *c1ccc([N+](=O)[O-])c(NCc2cccnc2)c1] |
| 1049 | 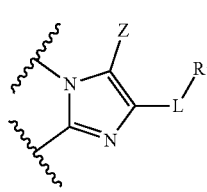 | —C(O)NHSO₂— | 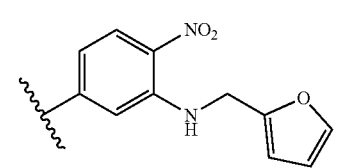 [SMILES: *c1ccc([N+](=O)[O-])c(NCc2ccco2)c1] |
| 1050 | 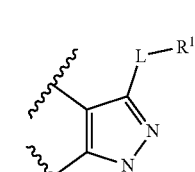 | —C(O)NHSO₂— | 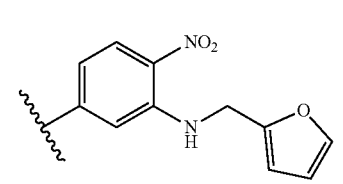 [SMILES: *c1ccc([N+](=O)[O-])c(NCc2ccco2)c1] |
| 1051 | 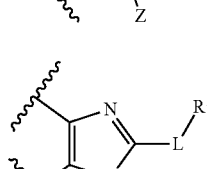 | —C(O)NHSO₂— | 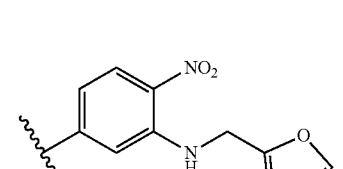 |
| 1052 | 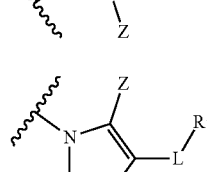 | —C(O)NHSO₂— | 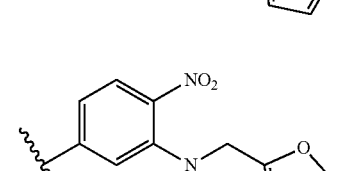 |
| 1053 | 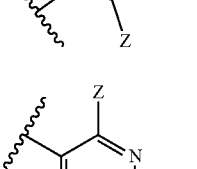 | —C(O)NHSO₂— | 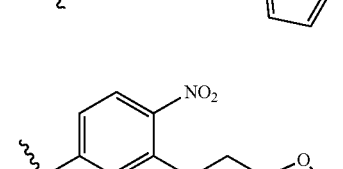 |
| 1054 | 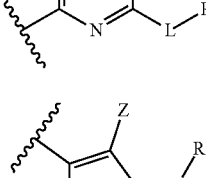 | —C(O)NHSO₂— | 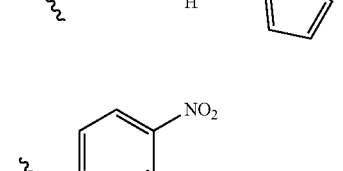 |
| 1055 | 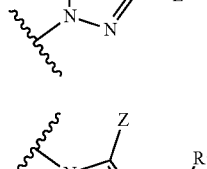 | —C(O)NHSO₂— | 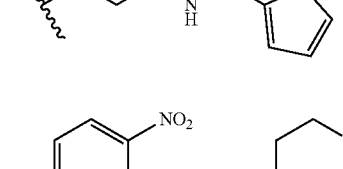 |

TABLE 1-continued

| Compound # | A | L | R¹ |
|---|---|---|---|
| 1056 | pyrazole with L-R¹ at 3-position, Z at N1 | —C(O)NHSO₂— | 4-nitro-3-(2-morpholinoethylamino)phenyl |
| 1057 | imidazole with L at 2-position, Z at N1 | —C(O)NHSO₂— | 4-nitro-3-(2-morpholinoethylamino)phenyl |
| 1058 | pyrrole with N-Z and L-R¹ | —C(O)NHSO₂— | 4-nitro-3-(2-morpholinoethylamino)phenyl |
| 1059 | pyrimidine with Z and L-R¹ | —C(O)NHSO₂— | 4-nitro-3-(2-morpholinoethylamino)phenyl |
| 1060 | pyrazole with Z and L-R¹ | —C(O)NHSO₂— | 4-nitro-3-(2-morpholinoethylamino)phenyl |
| 1061 | imidazole with Z and L-R¹ | —C(O)NHSO₂— | 4-nitro-3-(4-ethylpiperazin-1-yl)phenyl |
| 1062 | pyrazole with L-R¹ and Z | —C(O)NHSO₂— | 4-nitro-3-(4-ethylpiperazin-1-yl)phenyl |
| 1063 | imidazole with L-R¹ and Z | —C(O)NHSO₂— | 4-nitro-3-(4-ethylpiperazin-1-yl)phenyl |

TABLE 1-continued

| Compound # | A | L | R[1] |
|---|---|---|---|
| 1064 | pyrrole with Z, Z, L-R[1] | —C(O)NHSO$_2$— | 4-(4-ethylpiperazin-1-yl)-3-nitrophenyl-like (NO$_2$, N-ethylpiperazine) |
| 1065 | pyrimidine with Z, L-R[1] | —C(O)NHSO$_2$— | NO$_2$, N-ethylpiperazinyl phenyl |
| 1066 | pyrazole with Z, L-R[1] | —C(O)NHSO$_2$— | NO$_2$, N-ethylpiperazinyl phenyl |
| 1067 | imidazole with Z, L-R[1] | —C(O)NHSO$_2$— | 4-(benzamido)phenyl |
| 1068 | pyrazole with L-R[1], Z | —C(O)NHSO$_2$— | 4-(benzamido)phenyl |
| 1069 | imidazole with Z, Z, L-R[1] | —C(O)NHSO$_2$— | 4-(benzamido)phenyl |
| 1070 | pyrrole with Z, Z, L-R[1] | —C(O)NHSO$_2$— | 4-(benzamido)phenyl |
| 1071 | pyrimidine with Z, L-R[1] | —C(O)NHSO$_2$— | 4-(benzamido)phenyl |

TABLE 1-continued

| Compound # | A | L | R¹ |
|---|---|---|---|
| 1072 | pyrazole with Z, L-R¹ substituents | —C(O)NHSO₂— | phenyl-NH-C(O)-phenyl |
| 1073 | imidazole with Z, L-R¹ substituents | —C(O)NHSO₂— | 3-NO₂-4-(furan-2-ylamino)phenyl |
| 1074 | pyrazole with L-R¹, Z substituents | —C(O)NHSO₂— | 3-NO₂-4-(furan-2-ylamino)phenyl |
| 1075 | imidazole with Z, L-R¹ substituents | —C(O)NHSO₂— | 3-NO₂-4-(furan-2-ylamino)phenyl |
| 1076 | pyrrole with Z, L-R¹, Z substituents | —C(O)NHSO₂— | 3-NO₂-4-(furan-2-ylamino)phenyl |
| 1077 | pyrimidine with Z, L-R¹ substituents | —C(O)NHSO₂— | 3-NO₂-4-(furan-2-ylamino)phenyl |
| 1078 | pyrazole with Z, L-R¹ substituents | —C(O)NHSO₂— | 3-NO₂-4-(furan-2-ylamino)phenyl |
| 1079 | imidazole with Z, L-R¹ substituents | —C(O)NHSO₂— | 3-NO₂-4-((tetrahydrofuran-2-yl)methylamino)phenyl |

TABLE 1-continued

| Compound # | A | L | R¹ |
|---|---|---|---|
| 1080 | (pyrazole with L-R¹ at 3-position, Z at N1) | —C(O)NHSO$_2$— | (4-substituted phenyl with 2-NO$_2$ and NH-CH$_2$-tetrahydrofuran-2-yl) |
| 1081 | (imidazole with L-R¹ at 2-position, Z at N1) | —C(O)NHSO$_2$— | (4-substituted phenyl with 2-NO$_2$ and NH-CH$_2$-tetrahydrofuran-2-yl) |
| 1082 | (pyrrole with Z at N1, L-R¹ at 3-position, Z at 5-position) | —C(O)NHSO$_2$— | (4-substituted phenyl with 2-NO$_2$ and NH-CH$_2$-tetrahydrofuran-2-yl) |
| 1083 | (pyrimidine with Z at 4-position, L-R¹ at 2-position) | —C(O)NHSO$_2$— | (4-substituted phenyl with 2-NO$_2$ and NH-CH$_2$-tetrahydrofuran-2-yl) |
| 1084 | (pyrazole with Z at 4-position, L-R¹ at 3-position) | —C(O)NHSO$_2$— | (4-substituted phenyl with 2-NO$_2$ and NH-CH$_2$-tetrahydrofuran-2-yl) |
| 1085 | (imidazole with Z at 5-position, L-R¹ at 4-position) | —C(O)NHSO$_2$— | (4-substituted phenyl with 2-NO$_2$ and piperazinyl) |
| 1086 | (pyrazole with L-R¹ at 3-position, Z at N1) | —C(O)NHSO$_2$— | (4-substituted phenyl with 2-NO$_2$ and piperazinyl) |

TABLE 1-continued

| Compound # | A | L | R¹ |
|---|---|---|---|
| 1087 | (imidazole with L-R¹ and Z) | —C(O)NHSO₂— | 4-(piperazin-1-yl)-3-nitrophenyl |
| 1088 | (pyrrole with Z, L-R¹, Z) | —C(O)NHSO₂— | 4-(piperazin-1-yl)-3-nitrophenyl |
| 1089 | (pyrimidine with Z and L-R¹) | —C(O)NHSO₂— | 4-(piperazin-1-yl)-3-nitrophenyl |
| 1090 | (pyrazole with Z, L-R¹) | —C(O)NHSO₂— | 4-(piperazin-1-yl)-3-nitrophenyl |
| 1091 | (imidazole with Z, L-R¹) | —C(O)NHSO₂— | 4-(methylamino)-3-nitrophenyl |
| 1092 | (pyrazole with L-R¹, Z) | —C(O)NHSO₂— | 4-(methylamino)-3-nitrophenyl |
| 1093 | (imidazole with L-R¹, Z) | —C(O)NHSO₂— | 4-(methylamino)-3-nitrophenyl |

TABLE 1-continued

| Compound # | A | L | R¹ |
|---|---|---|---|
| 1094 | pyrrole (N-linked, Z,Z substituted, L-R¹) | —C(O)NHSO₂— | 4-(methylamino)-3-nitrophenyl |
| 1095 | pyrimidine (Z, L-R¹ substituted) | —C(O)NHSO₂— | 4-(methylamino)-3-nitrophenyl |
| 1096 | pyrazole (N-linked, Z, L-R¹ substituted) | —C(O)NHSO₂— | 4-(methylamino)-3-nitrophenyl |
| 1097 | pyrrole (N-linked, Z,Z, L-R¹ substituted) | —C(O)O— | H |
| 1098 | pyrrole (N-linked, Z,Z, L-R¹ substituted) | —C(O)NHSO₂— | 4-chlorophenyl |
| 1099 | pyrrole (N-linked, Z,Z, L-R¹ substituted) | —C(O)NHSO₂— | 4-morpholino-3-nitrophenyl |
| 1100 | pyrrole (N-linked, Z,Z, L-R¹ substituted) | —C(O)NHSO₂— | 3-nitro-4-((pyridin-3-ylmethyl)amino)phenyl |
| 1101 | pyrrole (N-linked, Z,Z, L-R¹ substituted) | —C(O)NHSO₂— | 4-((2-morpholinoethyl)amino)-3-nitrophenyl |

TABLE 1-continued

| Compound # | A | L | R¹ |
|---|---|---|---|
| 1102 | pyrrole(Z,Z,N,L,R¹) | —C(O)NHSO₂— | 4-(furan-2-ylmethylamino)-3-nitrophenyl |
| 1103 | pyrrole(Z,Z,N,L,R¹) | —C(O)NHSO₂— | 3-morpholino-4-nitrophenyl |
| 1104 | pyrrole(Z,Z,N,L,R¹) | —C(O)NHSO₂— | 4-nitro-3-((pyridin-3-ylmethyl)amino)phenyl |
| 1105 | pyrrole(Z,Z,N,L,R¹) | —C(O)NHSO₂— | 3-((furan-2-ylmethyl)amino)-4-nitrophenyl |
| 1106 | pyrrole(Z,Z,N,L,R¹) | —C(O)NHSO₂— | 3-((2-morpholinoethyl)amino)-4-nitrophenyl |
| 1107 | pyrrole(Z,Z,N,L,R¹) | —C(O)NHSO₂— | 3-(4-ethylpiperazin-1-yl)-4-nitrophenyl |
| 1108 | pyrrole(Z,Z,N,L,R¹) | —C(O)NHSO₂— | 4-benzamidophenyl |
| 1109 | pyrrole(Z,Z,N,L,R¹) | —C(O)NHSO₂— | 4-(furan-2-ylamino)-3-nitrophenyl |

TABLE 1-continued

| Compound # | A | L | R¹ |
|---|---|---|---|
| 1110 | pyrrole (N-Z, with Z substituents) | —C(O)NHSO₂— | 4-(tetrahydrofuran-2-ylmethylamino)-3-nitrophenyl |
| 1111 | pyrrole (N-Z, with Z substituents) | —C(O)NHSO₂— | 4-(piperazin-1-yl)-3-nitrophenyl |
| 1112 | pyrrole (N-Z, with Z substituents) | —C(O)NHSO₂— | 4-(methylamino)-3-nitrophenyl |
| 1113 | imidazole (N-Z) | —C(O)O— | —CH₃ |
| 1114 | pyrazole (N-Z) | —C(O)O— | —CH₃ |
| 1115 | imidazole (N-Z) | —C(O)O— | —CH₃ |
| 1116 | pyrrole (N-Z, with Z substituents) | —C(O)O— | —CH₃ |
| 1117 | pyrimidine | —C(O)O— | —CH₃ |

TABLE 1-continued

| Compound # | A | L | R[1] |
|---|---|---|---|
| 1118 | pyrazole with Z, L-R[1] | —C(O)O— | —CH$_3$ |
| 1119 | pyrrole with Z, Z, Z, L-R[1] | —C(O)O— | —CH$_3$ |
| 1120 | pyrazole with L-R[1], N-Z | —C(O)O— | H |
| 1121 | pyrazole with L-R[1], N-Z | —C(O)NHSO$_2$— | 4-chlorophenyl |
| 1122 | pyrazole with L-R[1], N-Z | —C(O)NHSO$_2$— | 3-nitro-4-morpholinophenyl |
| 1123 | pyrazole with L-R[1], N-Z | —C(O)NHSO$_2$— | 3-nitro-4-((pyridin-3-ylmethyl)amino)phenyl |
| 1124 | pyrazole with L-R[1], N-Z | —C(O)NHSO$_2$— | 3-nitro-4-((2-morpholinoethyl)amino)phenyl |
| 1125 | pyrazole with L-R[1], N-Z | —C(O)NHSO$_2$— | 3-nitro-4-((furan-2-ylmethyl)amino)phenyl |

TABLE 1-continued

| Compound # | A | L | R¹ |
| --- | --- | --- | --- |
| 1126 | pyrazole-L-R¹, N-Z | —C(O)NHSO₂— | phenyl with NO₂ and morpholine |
| 1127 | pyrazole-L-R¹, N-Z | —C(O)NHSO₂— | phenyl with NO₂ and NH-CH₂-pyridin-3-yl |
| 1128 | pyrazole-L-R¹, N-Z | —C(O)NHSO₂— | phenyl with NO₂ and NH-CH₂-furan-2-yl |
| 1129 | pyrazole-L-R¹, N-Z | —C(O)NHSO₂— | phenyl with NO₂ and NH-CH₂CH₂-morpholine |
| 1130 | pyrazole-L-R¹, N-Z | —C(O)NHSO₂— | phenyl with NO₂ and 4-ethylpiperazin-1-yl |
| 1131 | pyrazole-L-R¹, N-Z | —C(O)NHSO₂— | phenyl with NHC(O)phenyl |
| 1132 | pyrazole-L-R¹, N-Z | —C(O)NHSO₂— | phenyl with NO₂ and NH-furan-2-yl |

TABLE 1-continued

| Compound # | A | L | R¹ |
|---|---|---|---|
| 1133 | pyrazole(L-R¹, N-Z) | —C(O)NHSO₂— | 2-NO₂-4-(NH-CH₂-tetrahydrofuran-2-yl)phenyl |
| 1134 | pyrazole(L-R¹, N-Z) | —C(O)NHSO₂— | 2-NO₂-4-(piperazin-1-yl)phenyl |
| 1135 | pyrazole(L-R¹, N-Z) | —C(O)NHSO₂— | 2-NO₂-4-(NHMe)phenyl |
| 1136 | pyrazole(L-R¹, N-Z) | —C(O)O— | —CH₃ |
| 1137 | pyrazole(L-R¹, N-Z) | —C(O)O— | H |
| 1138 | pyrazole(L-R¹, N-Z) | —C(O)NHSO₂— | 4-Cl-phenyl |
| 1139 | pyrazole(L-R¹, N-Z) | —C(O)NHSO₂— | 2-NO₂-4-(morpholin-4-yl)phenyl |

TABLE 1-continued

| Compound # | A | L | R¹ |
|---|---|---|---|
| 1140 | pyrazole-L-R¹ with Z | —C(O)NHSO₂— | phenyl with NO₂ and NH-CH₂-(pyridin-3-yl) |
| 1141 | pyrazole-L-R¹ with Z | —C(O)NHSO₂— | phenyl with NO₂ and NH-CH₂CH₂-morpholine |
| 1142 | pyrazole-L-R¹ with Z | —C(O)NHSO₂— | phenyl with NO₂ and NH-CH₂-(furan-2-yl) |
| 1143 | pyrazole-L-R¹ with Z | —C(O)NHSO₂— | phenyl with NO₂ and morpholine |
| 1144 | pyrazole-L-R¹ with Z | —C(O)NHSO₂— | phenyl with NO₂ and NH-CH₂-(pyridin-3-yl) |
| 1145 | pyrazole-L-R¹ with Z | —C(O)NHSO₂— | phenyl with NO₂ and NH-CH₂-(furan-2-yl) |
| 1146 | pyrazole-L-R¹ with Z | —C(O)NHSO₂— | phenyl with NO₂ and NH-CH₂CH₂-morpholine |

TABLE 1-continued

| Compound # | A | L | R¹ |
|---|---|---|---|
| 1147 | pyrazole-L-R¹ | —C(O)NHSO₂— | 4-(4-ethylpiperazin-1-yl)-3-nitrophenyl |
| 1148 | pyrazole-L-R¹ | —C(O)NHSO₂— | 4-benzamidophenyl |
| 1149 | pyrazole-L-R¹ | —C(O)NHSO₂— | 4-((furan-2-yl)amino)-3-nitrophenyl |
| 1150 | pyrazole-L-R¹ | —C(O)NHSO₂— | 3-nitro-4-(((tetrahydrofuran-2-yl)methyl)amino)phenyl |
| 1151 | pyrazole-L-R¹ | —C(O)NHSO₂— | 3-nitro-4-(piperazin-1-yl)phenyl |
| 1152 | pyrazole-L-R¹ | —C(O)NHSO₂— | 4-(methylamino)-3-nitrophenyl |
| 1153 | pyrazole-L-R¹ | —C(O)O— | —CH₃ |

In some embodiments, the compound of formula (I), formula (II), formula (III), formula (IV), formula (V), formula (VI), or formula (VII), or a pharmaceutically acceptable salt, solvate, hydrate, cocrystal, or prodrug thereof is selected from Table 1 and R is independently selected from H, a halogen, and —COCH₃. In some embodiments, the compound of formula (I), formula (II), formula (III), formula (IV), formula (V), formula (VI), or formula (VII), or a pharmaceutically acceptable salt, solvate, hydrate, cocrystal, or prodrug thereof, is selected from Table 1 and Z is independently selected from H, halogen, optionally substituted alkyl, optionally substituted cycloalkyl, optionally substituted aralkyl, and optionally substituted heteroaryl. In some embodiments, the compound of formula (I), formula (II), formula (III), formula (IV), formula (V), formula (VI), or formula (VII), or a pharmaceutically acceptable salt, solvate, hydrate, cocrystal, or prodrug thereof, is selected from Table 1 and Z is independently selected from:

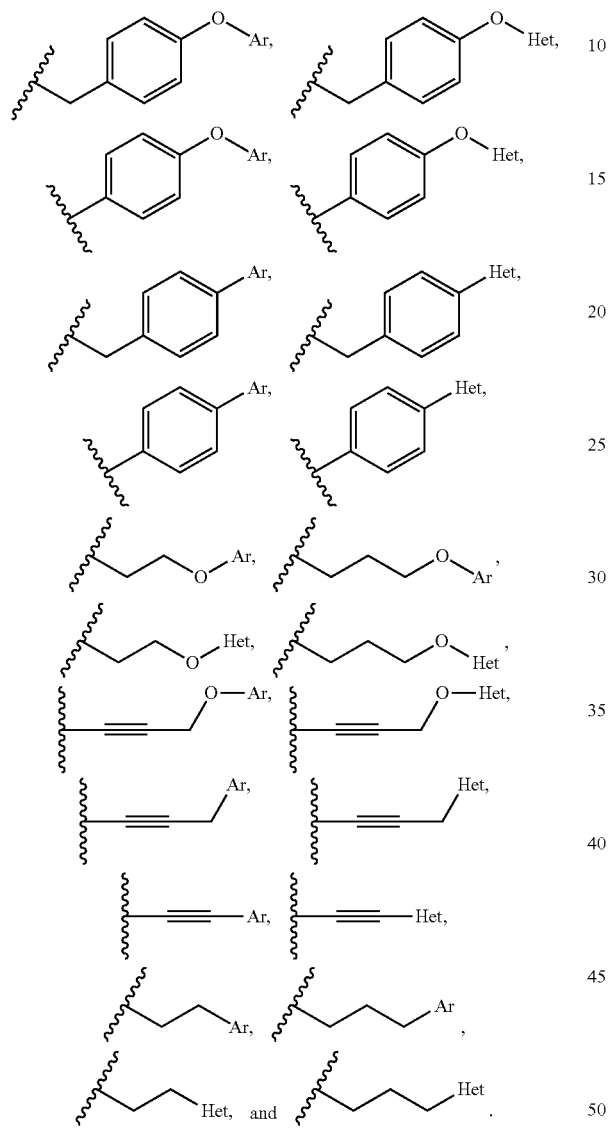

In some embodiments, Ar is an optionally substituted phenyl group, and Het is an optionally substituted heterocycle. In some embodiments, Ar is

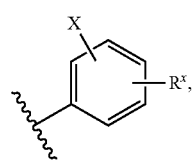

wherein X is one or more halogens, and $R^x$ is one or more optionally substituted alkyl groups. In some embodiments, Ar is selected from

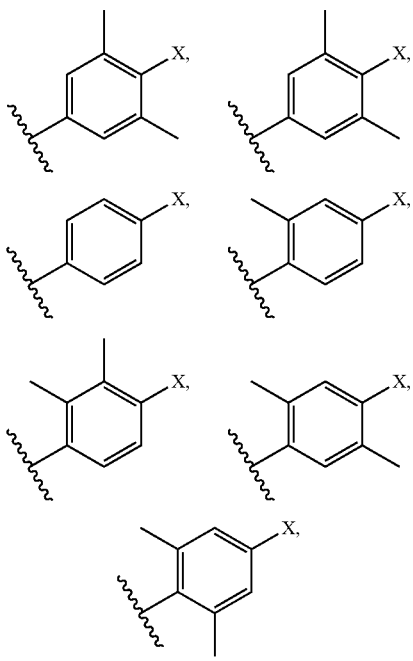

wherein X is a halogen. In some embodiments, X is Cl. In some embodiments, a halogen is Cl. In some embodiments, Het is N-morpholinyl.

In some embodiments, Z is selected from:

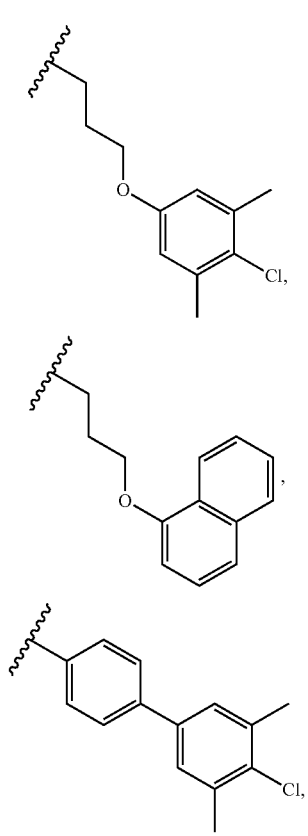

-continued
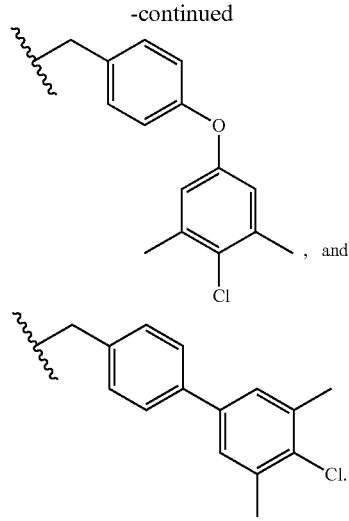
, and
In some embodiments, the compound of formula (I) is selected from Table 2:
TABLE 2
NB-1-070
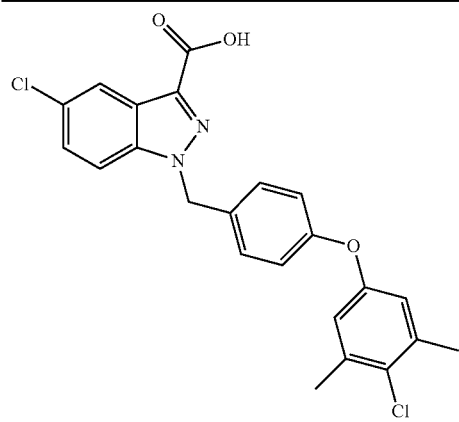
NB-1-084
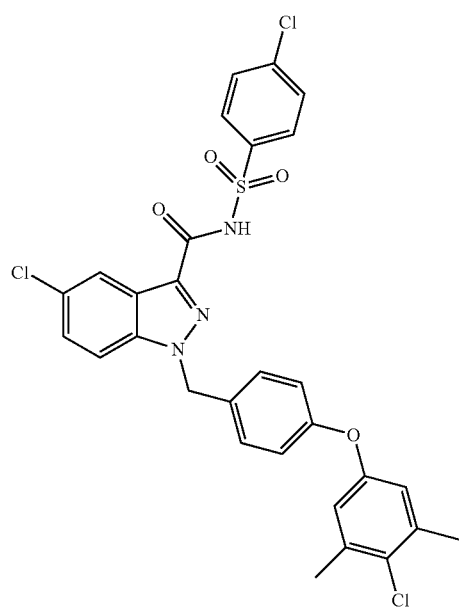 [SMILES: Cc1cc(Oc2ccc(Cn3nc(C(=O)NS(=O)(=O)c4ccc(Cl)cc4)c4cc(Cl)ccc43)cc2)cc(C)c1Cl]
TABLE 2-continued
NB-1-086
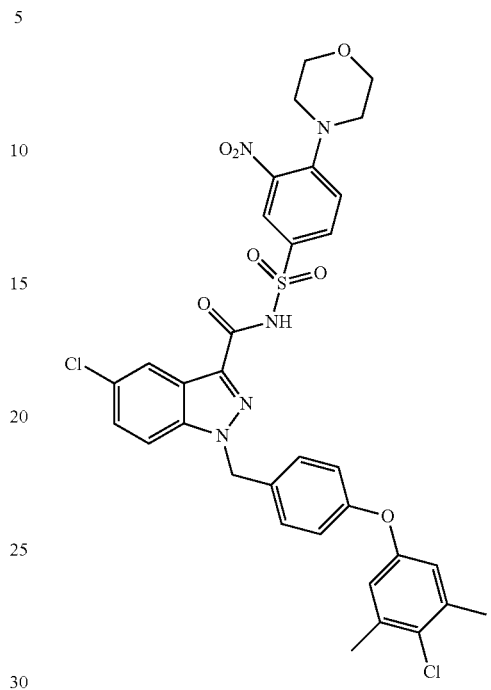
NB-1-087

TABLE 2-continued
NB-1-088
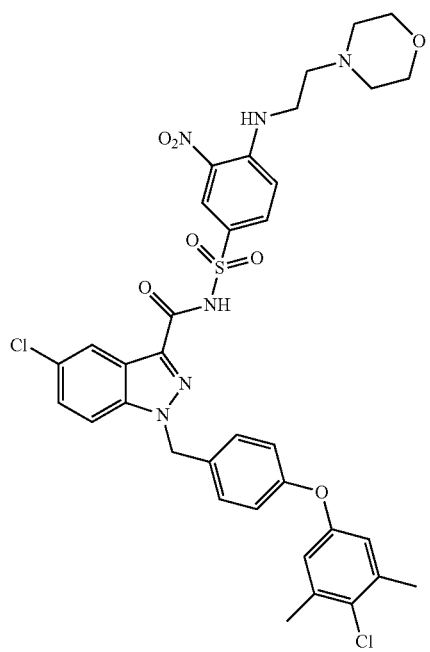 [SMILES: Cc1cc(Oc2ccc(Cn3nc(C(=O)NS(=O)(=O)c4ccc(NCCN5CCOCC5)c([N+](=O)[O-])c4)c4cc(Cl)ccc43)cc2)cc(C)c1Cl]
CG-1-016
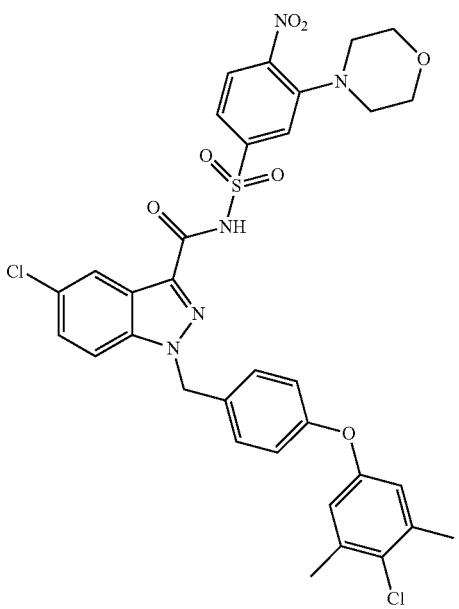
NB-1-089
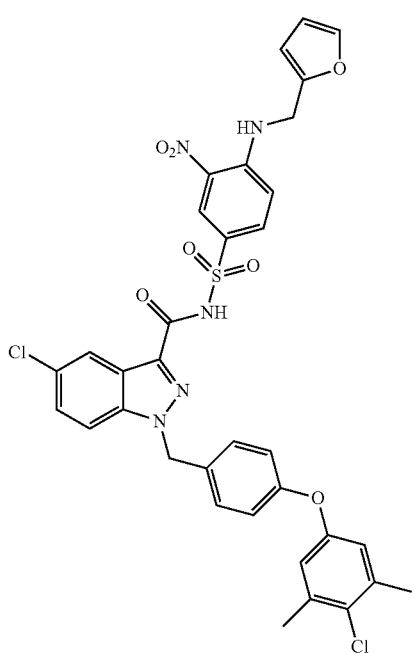 [SMILES: Cc1cc(Oc2ccc(Cn3nc(C(=O)NS(=O)(=O)c4ccc(NCc5ccco5)c([N+](=O)[O-])c4)c4cc(Cl)ccc43)cc2)cc(C)c1Cl]
CG-1-018

TABLE 2-continued
CG-1-019
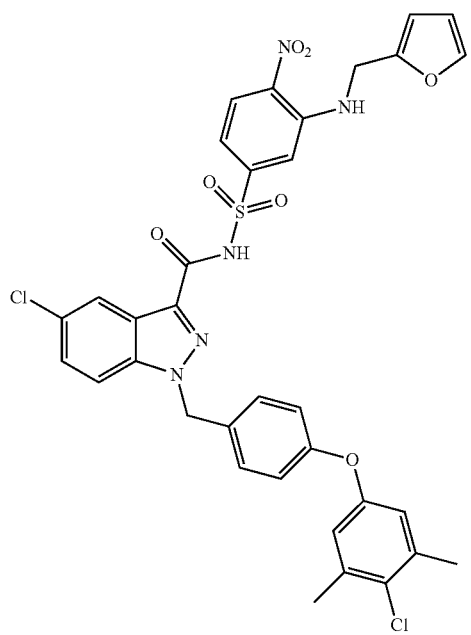 [SMILES: Cc1cc(Oc2ccc(Cn3nc(C(=O)NS(=O)(=O)c4ccc([N+](=O)[O-])c(NCc5ccco5)c4)c4cc(Cl)ccc43)cc2)cc(C)c1Cl]
CG-1-022
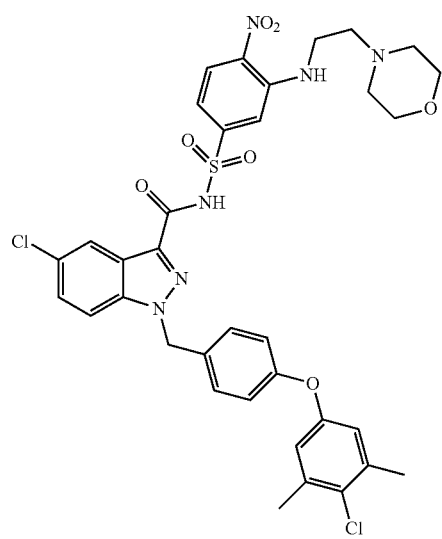 [SMILES: Cc1cc(Oc2ccc(Cn3nc(C(=O)NS(=O)(=O)c4ccc([N+](=O)[O-])c(NCCN5CCOCC5)c4)c4cc(Cl)ccc43)cc2)cc(C)c1Cl]
TABLE 2-continued
CG-1-023
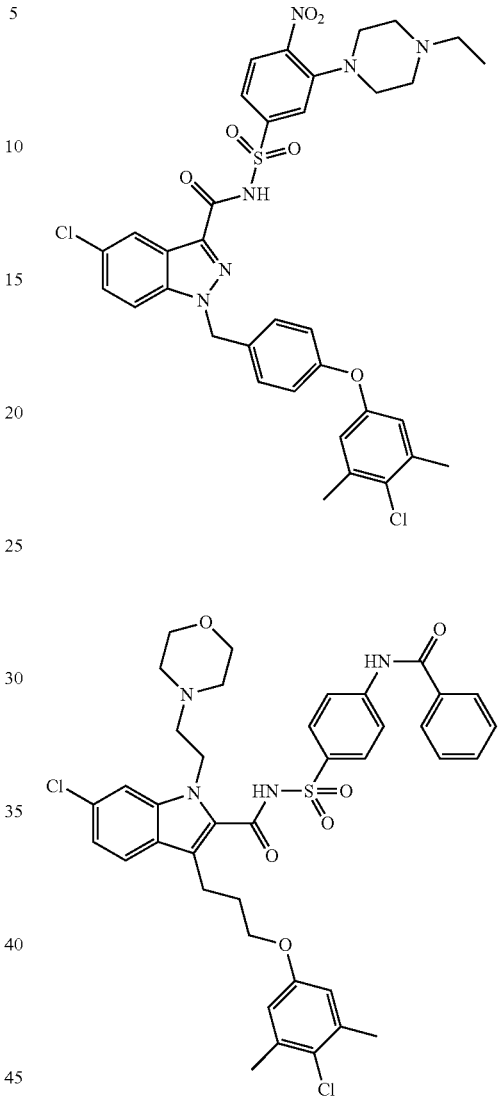
GV-1-028
BD-3-173
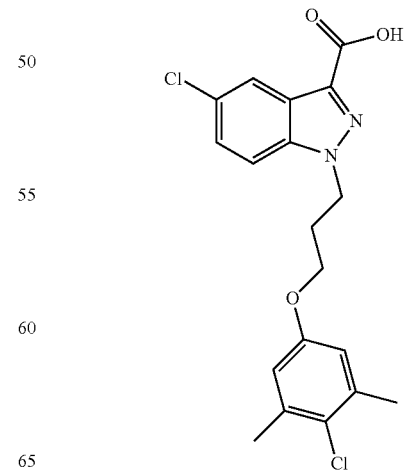

TABLE 2-continued
BD-3-180
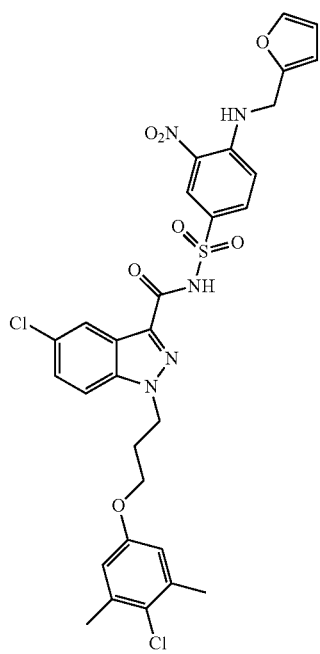 [SMILES: Cc1cc(OCCCn2nc(C(=O)NS(=O)(=O)c3ccc(NCc4ccco4)c([N+](=O)[O-])c3)c3cc(Cl)ccc32)cc(C)c1Cl]
BD-3-181
BD-3-183
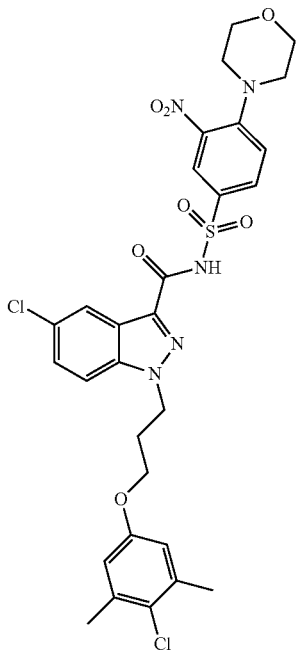 [SMILES: Cc1cc(OCCCn2nc(C(=O)NS(=O)(=O)c3ccc(N4CCOCC4)c([N+](=O)[O-])c3)c3cc(Cl)ccc32)cc(C)c1Cl]
BD-3-184

TABLE 2-continued
BD-3-187
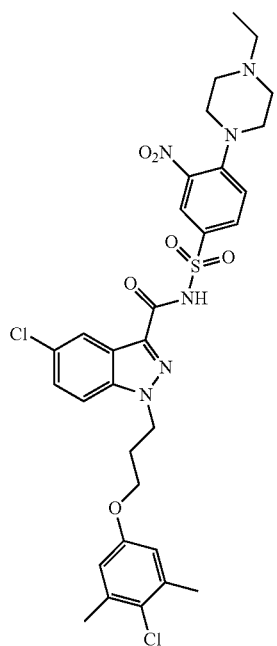 [SMILES: CCN1CCN(c2ccc(S(=O)(=O)NC(=O)c3nn(CCCOc4cc(C)c(Cl)c(C)c4)c4ccc(Cl)cc34)cc2[N+](=O)[O-])CC1]
BD-3-190
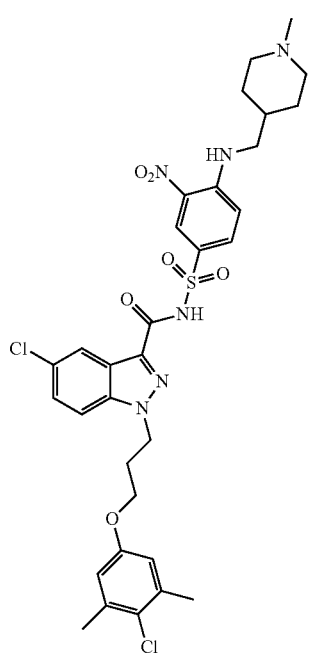 [SMILES: Cc1cc(OCCCn2nc(C(=O)NS(=O)(=O)c3ccc(NCC4CCN(C)CC4)c([N+](=O)[O-])c3)c3cc(Cl)ccc32)cc(C)c1Cl]
TABLE 2-continued
BD-3-190-b
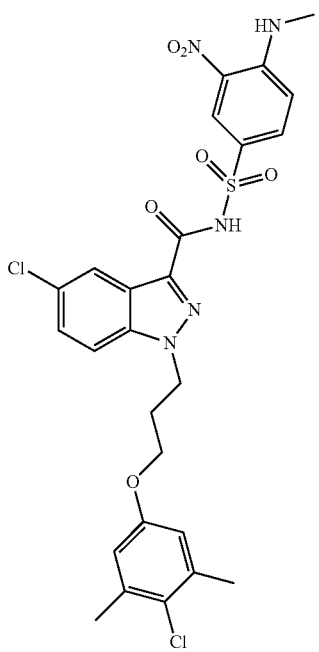 [SMILES: CNc1ccc(S(=O)(=O)NC(=O)c2nn(CCCOc3cc(C)c(Cl)c(C)c3)c3ccc(Cl)cc23)cc1[N+](=O)[O-]]
BD-3-187-b
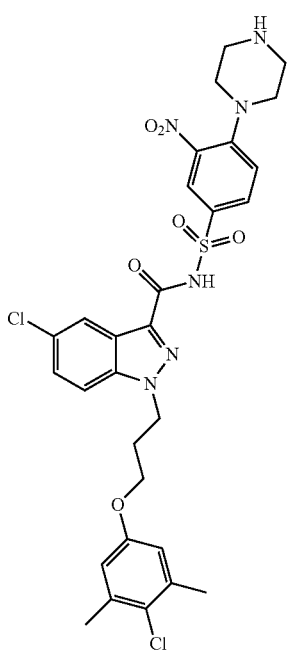 [SMILES: Cc1cc(OCCCn2nc(C(=O)NS(=O)(=O)c3ccc(N4CCNCC4)c([N+](=O)[O-])c3)c3cc(Cl)ccc32)cc(C)c1Cl]

TABLE 2-continued
BD-3-001
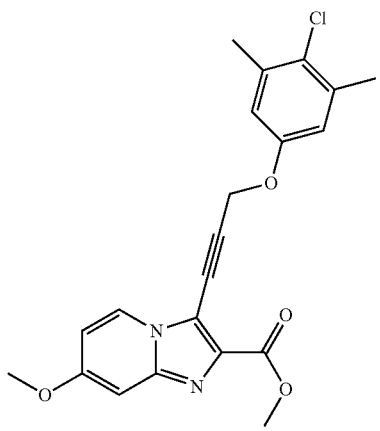
BD-3-180-b
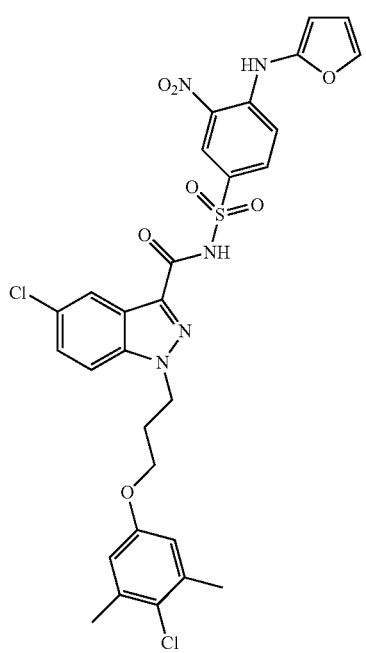 [SMILES: Cc1cc(OCCCn2nc(C(=O)NS(=O)(=O)c3ccc(Nc4ccco4)c([N+](=O)[O-])c3)c3cc(Cl)ccc32)cc(C)c1Cl]
2001
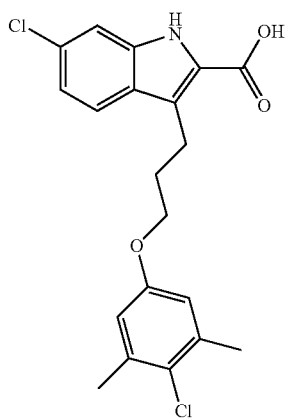 [SMILES: Cc1cc(OCCCc2c(C(=O)O)[nH]c3cc(Cl)ccc23)cc(C)c1Cl]
TABLE 2-continued
2002
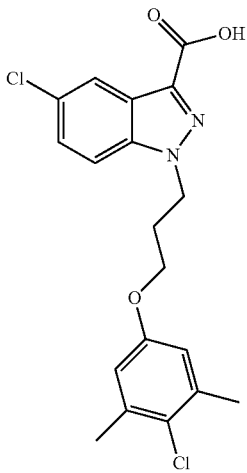 [SMILES: Cc1cc(OCCCn2nc(C(=O)O)c3cc(Cl)ccc32)cc(C)c1Cl]
2003
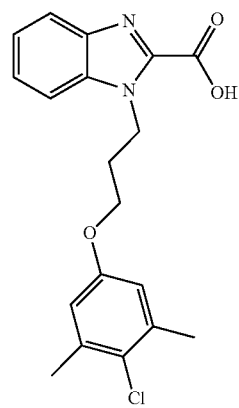 [SMILES: Cc1cc(OCCCn2c(C(=O)O)nc3ccccc32)cc(C)c1Cl]
2004
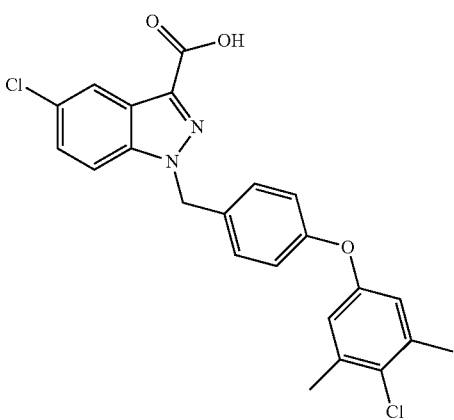 [SMILES: Cc1cc(Oc2ccc(Cn3nc(C(=O)O)c4cc(Cl)ccc43)cc2)cc(C)c1Cl]

TABLE 2-continued
2005
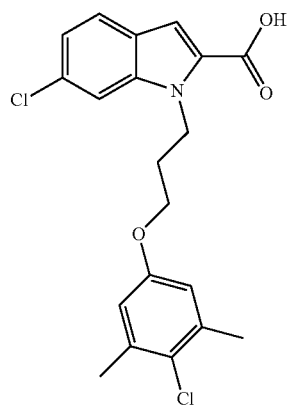 [SMILES: Cc1cc(OCCCn2c(C(=O)O)cc3ccc(Cl)cc32)cc(C)c1Cl]
2006
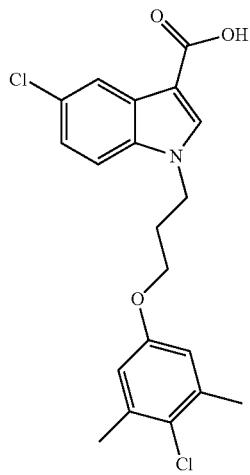 [SMILES: Cc1cc(OCCCn2cc(C(=O)O)c3cc(Cl)ccc32)cc(C)c1Cl]
2007
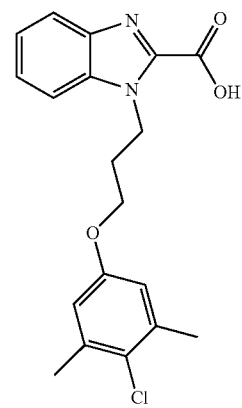 [SMILES: Cc1cc(OCCCn2c(C(=O)O)nc3ccccc32)cc(C)c1Cl]
2008
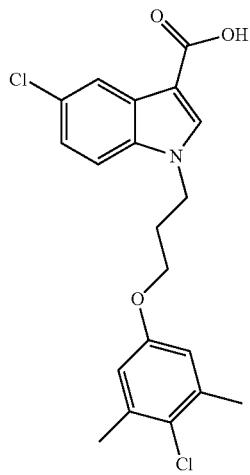 [SMILES: Cc1cc(OCCCn2cc(C(=O)O)c3cc(Cl)ccc32)cc(C)c1Cl]
5
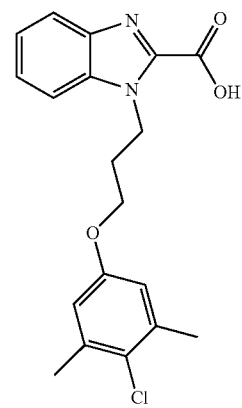 [SMILES: Cc1cc(OCCCn2c(C(=O)O)nc3ccccc32)cc(C)c1Cl]
10
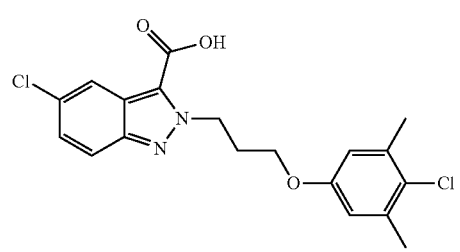 [SMILES: Cc1cc(OCCCn2nc3ccc(Cl)cc3c2C(=O)O)cc(C)c1Cl]
11
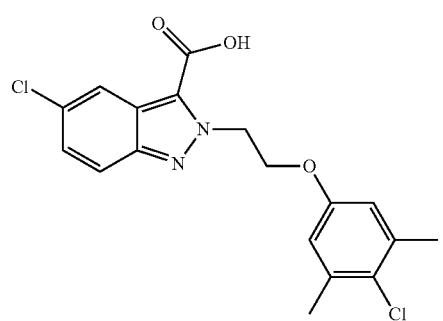 [SMILES: Cc1cc(OCCn2nc3ccc(Cl)cc3c2C(=O)O)cc(C)c1Cl]

TABLE 2-continued

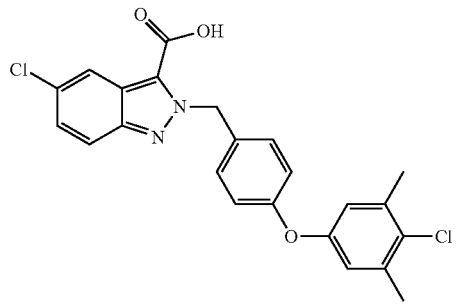 [SMILES: Cc1cc(Oc2ccc(Cn3nc4ccc(Cl)cc4c3C(=O)O)cc2)cc(C)c1Cl]

12

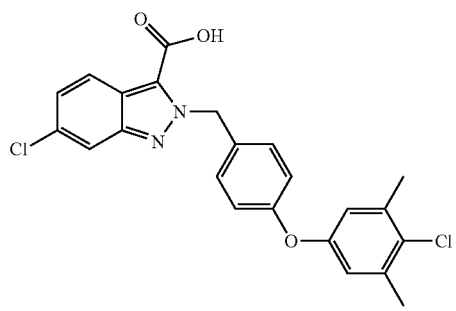 [SMILES: Cc1cc(Oc2ccc(Cn3nc4cc(Cl)ccc4c3C(=O)O)cc2)cc(C)c1Cl]

49

Methods of Treating Cancers and Other Diseases

The compounds and compositions described herein can be used in methods for treating diseases. In some embodiments, the compounds and compositions described herein can be used in methods for treating diseases associated with the upregulation of myeloid cell leukemia-1 (Mcl-1) oncoprotein and/or the upregulation of B-cell lymphoma-2 (Bcl-2). In some embodiments, the compounds and compositions described herein can be used for the treatment of hyperproliferative disorders, including those hyperproliferative disorders associated with the upregulation of Mcl-1 and/or Bcl-2. The compounds and compositions described herein may also be used in treating other disorders as described herein and in the following paragraphs.

In some embodiments, the compounds and compositions described herein (e.g., selective Mcl-1 inhibitors, selective Bcl-2 inhibitors, and/or dual Mcl-1/Bcl-2) may include both an Mcl-1 binding portion (i.e., a p2 binding moiety as described herein) and a Bcl-2 binding portion (i.e., a p4 binding moiety). In some embodiments, the compounds described herein are dual Mcl-1/Bcl-2 inhibitors that include both an Mcl-1 binding portion and a Bcl-2 binding portion. Compounds described herein include, but are not limited to: compounds of formula (I), formula (II), formula (III), formula (IV), formula (V), formula (VI), or formula (VII), and their features and limitations as described herein; compounds of formulas 5, 9-12, 31-52, 1001-1153, and 2001-2008, and their features and limitations as described herein; and compounds NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, and their features and limitations as described herein.

In some embodiments, the hyperproliferative disorder described herein is cancer. In some embodiments, the cancer is selected from the group consisting of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like.

In some embodiments, the hyperproliferative disorder treated by the compounds and compositions described herein includes cells having Mcl-1 protein and/or Mcl-1 related protein expression. In some embodiments, the hyperproliferative disorder treated by the compounds and compositions described herein includes cells having Bcl-2 protein and/or Bcl-2 related protein expression. In some embodiments, the hyperproliferative disorder treated by the compounds and compositions described herein includes cells having both Mcl-1 and Bcl-2 protein and/or Mcl-1 and Bcl-2 related protein expression. In some embodiments, the disease treated by the compounds and compositions described herein is selected from the group consisting of myeloid leukemia, acute myeloid leukemia, multiple myeloma, non-small cell lung cancer, pancreatic cancer, prostate cancer, and ovarian cancer.

In some embodiments, the methods include inhibiting Mcl-1 and/or Bcl-2 protein activity, comprising contacting Mcl-1 and/or Bcl-2 protein with a therapeutically effective amount of a compound of formula (I), formula (II), formula (III), formula (IV), formula (V), formula (VI), or formula (VII), and their features and limitations as described herein; or formula 5, 9-12, 31-52, 1001-1153, or 2001-2008, and their features and limitations as described herein; or formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, or BD-3-180-b, and their features and limitations as described herein, or pharmaceutically acceptable salt thereof.

In some embodiments, the methods include treating a disease by inhibiting Mcl-1 and/or Bcl-2 protein activity in a patient in need of such treatment, the method comprising administering a therapeutically effective amount of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof.

Efficacy of the methods, compounds, and combinations of compounds described herein in treating, preventing and/or managing the indicated diseases or disorders can be tested using various animal models known in the art. For example, methods for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development*, 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32. Models for determining efficacy of treatments for colorectal cancer, including the CT26 model, are described in Castle, et al., *BMC Genomics*, 2013, 15, 190; Endo, et al., *Cancer Gene Therapy*, 2002, 9, 142-148; Roth et al., *Adv. Immunol.* 1994, 57, 281-351; Fearon, et al., *Cancer Res.* 1988, 48, 2975-2980.

Pharmaceutical Compositions

In an embodiment, the invention provides a pharmaceutical composition for use in the treatment of the diseases and conditions described herein.

The pharmaceutical compositions are typically formulated to provide a therapeutically effective amount of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, as described herein, or a pharmaceutically acceptable salt, solvate, or hydrate thereof, as the active ingredient. Typically, the pharmaceutical compositions also comprise one or more pharmaceutically acceptable excipients, carriers, including inert solid diluents and fillers, diluents, including sterile aqueous solution and various organic solvents, permeation enhancers, solubilizers and adjuvants.

The pharmaceutical compositions described above are preferably for use in the treatment of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma.

In some embodiments, the concentration of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-

019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of: a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

Each of the compounds provided according to the invention is effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting pharmaceutical compositions and methods for preparing the same.

Pharmaceutical Compositions for Oral Administration

In preferred embodiments, the invention provides a pharmaceutical composition for oral administration containing: a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, and a pharmaceutical excipient suitable for administration.

In preferred embodiments, the invention provides a solid pharmaceutical composition for oral administration containing: (i) an effective amount of: a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, and (ii) a pharmaceutical excipient suitable for administration. In some embodiments, the composition further contains (iii) an effective amount of an additional active pharmaceutical ingredient. For example, additional active pharmaceutical ingredients, as used herein, may include one or more compounds that induce cell cycle arrest and/or apoptosis in cells containing functional Mcl-1 and/or Bcl-2 proteins. Such additional active pharmaceutical ingredients may also include those compounds used for sensitizing cells to additional agent(s), such as inducers of apoptosis and/or cell cycle arrest, and chemoprotection of normal cells through the induction of cell cycle arrest prior to treatment with chemotherapeutic agents.

In some embodiments, the pharmaceutical composition may be a liquid pharmaceutical composition suitable for oral consumption.

Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Active pharmaceutical ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyllactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyllactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In preferred embodiments, the invention provides a pharmaceutical composition for injection containing: a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-

190, BD-3-190-b, BD-3-187-b, BD-3-001, and BD-3-180-b, or pharmaceutically acceptable salt thereof, described herein, and a pharmaceutical excipient suitable for injection. Components and amounts of compounds in the compositions are as described herein.

The forms in which the compositions of the invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating: a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In preferred embodiments, the invention provides a pharmaceutical composition for transdermal delivery containing: a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of: a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of: a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, or a pharmaceutical composition of these compounds can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The compound of formula (I), formula (II), formula (III), formula (IV), formula (V), formula (VI), or formula (VII), and their features and limitations as described herein; compound of formulas 5, 9-12, 31-52, 1001-1153, or 2001-2008, and their features and limitations as described herein; and/or compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, can also be administered intraadiposally or intrathecally.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. A compound of formula (I), formula (II), formula (III), formula (IV), formula (V), formula (VI), or formula (VII), and their features and limitations as described herein; compound of formulas 5, 9-12, 31-52, 1001-1153, or 2001-2008, and their features and limitations as described herein; and/or compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. A compound of formula (I), formula (II), formula (III), formula (IV), formula (V), formula (VI), or formula (VII), and their features and limitations as described herein; compound of formulas 5, 9-12, 31-52, 1001-1153, or 2001-2008, and their features and limitations as described herein; and/or compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, may additionally be administered intravascularly from a balloon used during angioplasty. Extravascular administration of a compound of formula (I), formula (II), formula (III), formula (IV), formula (V), formula (VI), or formula (VII), and their features and limitations as described herein; compound of formulas 5, 9-12, 31-52, 1001-1153, or 2001-2008, and their features and limitations as described herein; and/or compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, via the pericard or via advential application of formulations of the invention may also be performed to decrease restenosis.

Exemplary parenteral administration forms include solutions or suspensions of a compound of formula (I), formula (II), formula (III), formula (IV), formula (V), formula (VI), or formula (VII), and their features and limitations as described herein; compound of formulas 5, 9-12, 31-52, 1001-1153, or 2001-2008, and their features and limitations as described herein; and/or compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, in sterile aqueous solutions, for example, aqueous propylene glycol or dextrose solutions. Such dosage forms can be suitably buffered, if desired.

The invention also provides kits. The kits include a compound of formula (I), formula (II), formula (III), formula (IV), formula (V), formula (VI), or formula (VII), and their features and limitations as described herein; compound of formulas 5, 9-12, 31-52, 1001-1153, or 2001-2008, and their features and limitations as described herein; and/or compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In some embodiments, the compound of formula (I), formula (II), formula (III), formula (IV), formula (V), formula (VI), or formula (VII), and their features and limitations as described herein; compound of formulas 5, 9-12, 31-52, 1001-1153, or 2001-2008, and their features and limitations as described herein; and/or compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, and another active pharmaceutical ingredient are provided as separate compositions in separate containers within the kit. In some embodiments, the compound of formula (I), formula (II), formula (III), formula (IV), formula (V), formula (VI), or formula (VII), and their features and limitations as described herein; compound of formulas 5, 9-12, 31-52, 1001-1153, or 2001-2008, and their features and limitations as described herein; and/or compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The kits described above are preferably for use in the treatment of the diseases and conditions described herein. In a preferred embodiment, the kits are for use in the treatment of cancer or hyperproliferative disorders.

In a particular embodiment, the kits described herein are for use in the treatment of cancer. In some embodiments, the kits described herein are for use in the treatment of a cancer selected from the group consisting of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

Dosages and Dosing Regimens

The amounts of: a compound of formula (I), formula (II), formula (III), formula (IV), formula (V), formula (VI), or formula (VII), and their features and limitations as described herein; A compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, administered will be dependent on the human or mammal being treated, the severity of the disorder or condition, the rate of administration, the disposition of the compounds and the discretion of the prescribing physician. However, an effective dosage of each is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or A compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, may be provided in units of mg/kg of body mass or in mg/m$^2$ of body surface area.

In some embodiments, a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein is administered in multiple doses. In a preferred embodiment, a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or A compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein is administered in multiple doses. Dosing may be once, twice, three times, four times, five times, six times, or more than six times per day. Dosing may be once a month, once every two weeks, once a week, or once every other day. In other embodiments, a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, is administered about once per day to about 6 times per day. In some embodiments, a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, is administered once daily, while in other embodiments, a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein is administered twice daily, and in other embodiments a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, is administered three times daily.

Administration a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, may continue as long as necessary. In some embodiments, a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, is administered for more than 1, 2, 3, 4, 5, 6, 7, 14, or 28 days. In some embodiments, a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein is administered for less than 28, 14, 7, 6, 5, 4, 3, 2, or 1 day. In some embodiments, a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein is administered chronically on an ongoing basis—e.g., for the treatment of chronic effects. In another embodiment, the administration of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, continues for less than about 7 days. In yet another embodiment, the administration continues for more than about 6, 10, 14, 28 days, two months, six months, or one year. In some cases, continuous dosing is achieved and maintained as long as necessary.

In some embodiments, an effective dosage of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg.

In some embodiments, an effective dosage of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some instances, dosage levels below the lower limit of the aforesaid ranges may be more than adequate, while in other cases still larger doses may be employed without causing any harmful side effect—e.g., by dividing such larger doses into several small doses for administration throughout the day.

An effective amount of a compound of formula (I), formula (II), formula (III), formula (IV), formula (V), formula (VI), or formula (VII), and their features and limitations as described herein; a compound of formulas 5, 9-12, 31-52, 1001-1153, or 2001-2008, and their features and limitations as described herein; and/or a compound of formula NB-1-070, NB-1-084, NB-1-086, NB-1-087, NB-1-088, NB-1-089, CG-1-016, CG-1-018, CG-1-019, CG-1-022, CG-1-023, GV-1-028, BD-3-173, BD-3-180, BD-3-181, BD-3-183, BD-3-184, BD-3-187, BD-3-190, BD-3-190-b, BD-3-187-b, BD-3-001, and BD-3-180-b, or pharmaceutically acceptable salt thereof, described herein, may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Synthetic Scheme

Scheme 1 illustrates the functionalization and creation of certain indazole derivatives described herein; 5-chloroisatin is used as the starting material, but the synthetic approach is equally applicable to other starting materials, including, but not limited to, 6-chloroisatin, 7-chloroisatin, and 4-chloroisatin, along with their bromine derivatives 5-bromoisatin, 6-bromoisatin, 7-bromoisatin, 4-bromoisatin, and the like (eqs=equivalents or stoichiometric amount).

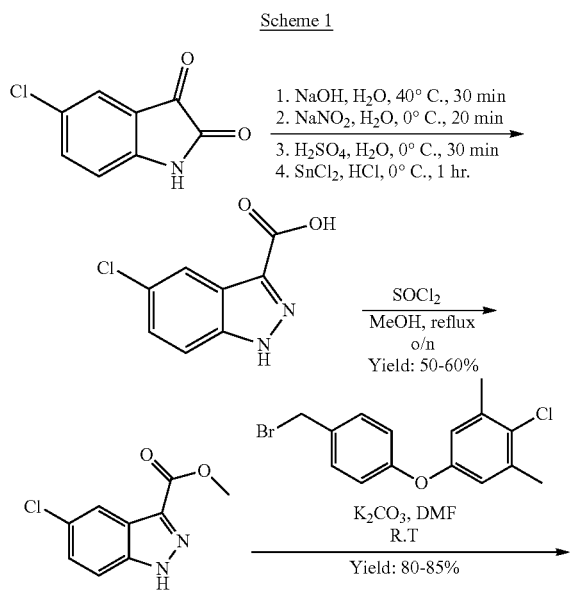

Scheme 1

-continued

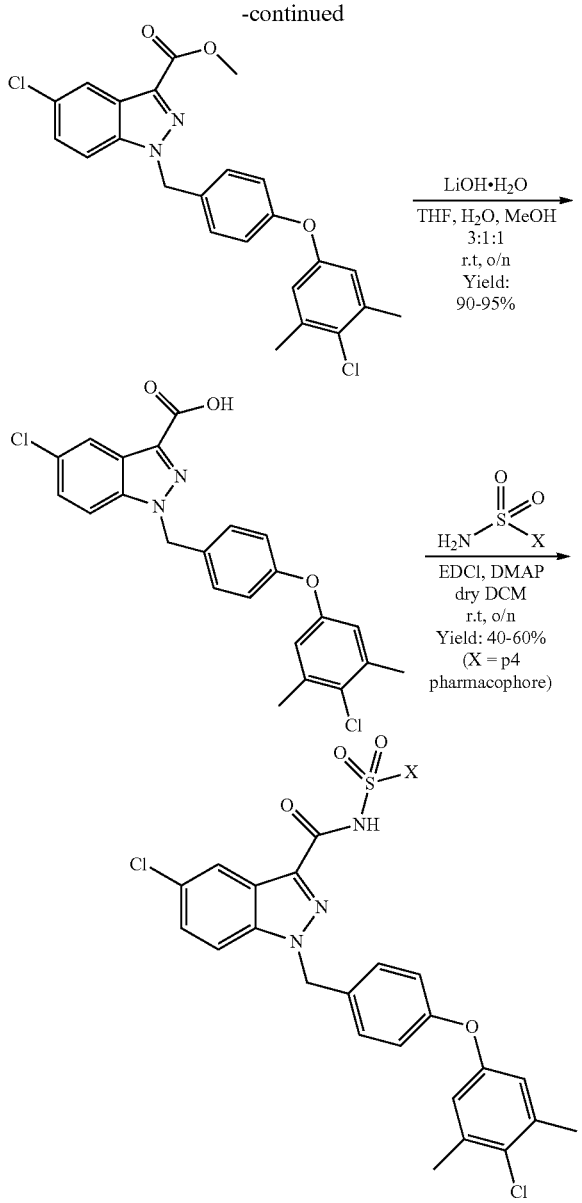

Step 1: Synthesis of the indazole core: 5-chloroisatin was added to a reaction flask followed by addition of H₂O to a concentration of 0.4 M. NaOH (1.1 eqs) was then added and the reaction mixture was heated at 40° C. for 15 mins or until all material was solubilized. The reaction mixture was then placed on ice and cooled for 5 mins at 0° C. NaNO$_2$ (1.2 eqs) in H$_2$O was then added dropwise to the reaction vessel via a dripping funnel. Next, H$_2$SO$_4$ (2.0 eqs) in H$_2$O was added dropwise via a dripping funnel and the reaction mixture was stirred at 0° C. for 30 mins. After 30 mins SnCl$_2$ (2.5 eqs) in 12 M HCl was added dropwise via a dripping funnel and the reaction mixture was stirred for 1 hr at 0° C. The reaction mixture was then filtered and the precipitate was washed with H$_2$O. The crude precipitate was carried onto the next step without further purification.

Step 2: Methyl esterification of the carboxylic acid: the crude precipitate was dissolved in MeOH (0.1 M) and SOCl$_2$ (3.0 eqs) was added slowly to the reaction mixture, then refluxed overnight. Upon completion, the solvent was evaporated and the crude material was dry loaded onto silica gel to undergo flash column chromatography for purification (2:1 Hexanes/Ethyl Acetate). The collected product fractions were combined, concentrated down and azeotroped with CHCl$_3$.

Step 3: Alkylation of the indazole core: the methyl ester indazole from the previous step was dissolved in DMF (0.1 M) in a reaction vessel and K$_2$CO$_3$ (2.0 eqs) was added. The alkylbromide (1.1 eqs) was then added and the reaction mixture was stirred overnight at 25° C.; depending on the alkylbromide, the reaction was heated at 80-90° C. overnight. The reaction was then partitioned between sat. NaHCO$_3$ and Ethyl Acetate. The organic layer was collected, dried with Na$_2$SO$_4$, filtered, concentrated down and azeotroped with CHCl$_3$ to afford the desired product.

Step 4: Saponification of the ester to the carboxylic acid: the alkylated indazole methyl ester was placed in a reaction vessel and solubilized in a mixture of THF/H$_2$O/MeOH (0.1 M) at a 3:1:1 ratio. LiOH monohydrate (3.0 eqs) was then added and the reaction mixture was stirred overnight at 25° C. The reaction was then partitioned between 1 M HCl and Ethyl Acetate. The organic layer was collected, dried with Na$_2$SO$_4$, filtered, concentrated down and azeotroped with CHCl$_3$ to afford the desired product.

Step 5: Sulfonamide couplings to afford the desired acylsulfonamides: the carboxylic acid from the previous step was placed in a reaction vessel and anhydrous DCM (0.1 M) was added. Next DMAP (0.3 eqs) and EDCI (1.5 eqs) were added followed by the desired sulfonamide (1.2 eqs). The reaction mixture was stirred overnight at 25° C. Upon completion, the solvent was evaporated off and the crude material was dry loaded onto silica gel for flash column chromatography purification (solvent used was mixture of DCM/MeOH/H$_2$O at a ratio of 92:7:1). The collected product fractions were combined, concentrated down and azeotroped with CHCl$_3$ to afford the functionalized indazole final products.

Example 2: Fluorescence Polarization Competition Assay

Table 3 lists inhibition constants of certain synthesized indazoles described herein against different members of the Bcl-2 anti-apoptotic proteins. These values were determined from a fluorescence polarization competition assay involving a fluorescently labeled peptide (BAK) bound to the desired Bcl-2 anti-apoptotic protein. In cancerous cells, BAK is bound to the anti-apoptotic proteins significantly more often, overall allowing the cells to evade apoptosis and progress further into tumorigenesis. Thus, freeing BAK from the anti-apoptotic proteins will allow the cells to restore apoptosis and die before further tumor progression can occur. These inhibition constants are the concentrations at which the indazole derivatives can displace 50% of BAK from the indicated Bcl-2 anti-apoptotic proteins. Overall the lower the K$_i$ the more potent the inhibitor.

TABLE 3

| Compound # | MCL-1 Affinity K$_i$ (µM) | BCL-2 Affinity K$_i$ (µM) | BCL-X$_L$ Affinity K$_i$ (µM) |
| --- | --- | --- | --- |
| BD-3-173 | 5.800 ± 0.36 | 5.7915 ± 0.62 | NA |
| BD-3-180 | 0.480 ± 0.03 | 0.5724 ± 0.05 | 0.597 ± 0.18 |
| BD-3-181 | 0.840 ± 0.05 | 0.6944 ± 0.09 | 0.574 ± 0.11 |
| BD-3-183 | 0.920 ±0.03 | 0.8683 ± 0.13 | 1.0595 ± 0.34 |
| BD-3-184 | 0.690 ± 0.03 | 1.1680 ± 0.16 | 0.8396 ± 0.14 |
| BD-3-190 | NA | 8.9306 ± 0.29 | NA |
| NB-1-070 | 0.910 ± 0.05 | 1.0399 ± 0.19 | 2.0129 ± 0.35 |

TABLE 3-continued

| Compound # | MCL-1 Affinity $K_i$ (µM) | BCL-2 Affinity $K_i$ (µM) | BCL-$X_L$ Affinity $K_i$ (µM) |
|---|---|---|---|
| NB-1-084 | 0.280 ± 0.01 | 1.0854 ± 0.45 | 0.8398 ± 0.2281 |
| NB-1-086 | 0.320 ± 0.01 | 0.5686 ± 0.04 | 0.8398 ± 0.2281 |
| NB-1-087 | 0.520 ± 0.03 | 0.6113 ± 0.20 | 0.5573 ± 0.08 |
| NB-1-088 | 0.750 ± 0.06 | 0.7382 ± 0.19 | NA |
| NB-1-089 | 0.260 ± 0.01 | 0.2658 ± 0.02 | 0.5512 ± 0.07 |
| CG-1-016 | 0.370 ± 0.02 | 0.4511 ± 0.04 | 0.436 ± 0.07 |
| CG-1-018 | 0.480 ± 0.03 | 0.3841 ± 0.03 | 0.436 ± 0.07 |
| CG-1-019 | 1.140 ± 0.05 | 0.3841 ± 0.03 | 0.325 ± 0.05 |
| CG-1-023 | 12.380 ± 0.37 | 74.2533 ± 11.48 | NA |

Example 3: A Polypharmacology Approach Towards the Design and Synthesis of Dual MCL-1 and BCL-2 Inhibitors The role of the Bcl-2 protein family in the development of tumorigenesis has been characterized by previous scientific studies. To review, the members of the Bcl-2 protein family, which are characterized as either pro-apoptotic or anti-apoptotic, are key regulators of the intrinsic apoptosis pathway. Under normal cellular conditions, the pro-apoptotic protein members (BAK, BAX) are sequestered by the anti-apoptotic protein members (MCL-1, BCL-2, BCL-$X_L$, BFL-1) through an alpha-helix mediated protein-protein interaction (PPI), thus halting the initiation of apoptosis. Specifically, the pro-apoptotic proteins' alpha-helical BH3 domains bind into hydrophobic binding grooves on the surface of the anti-apoptotic proteins. These hydrophobic binding grooves are composed of binding sub-pockets (p1-p4) which can accommodate conserved residues on the BH3 domains. Additionally, the BH3 domains possess an aspartate residue that form salt bridge interactions with conserved arginine residues located around the hydrophobic grooves, further strengthening the PPI. Under apoptotic conditions, BH3-only activator proteins (BIM, BAD, NOXA, PUMA) are expressed and promote the release of the pro-apoptotic proteins, via competitively binding to the anti-apoptotic proteins, to initiate apoptosis. The overexpression of the Bcl-2 anti-apoptotic proteins may block in cancer cell populations the release of the pro-apoptotic proteins once cells encounter apoptotic stimuli, thus promoting further tumorigenesis.

A strategy for overcoming this tumorigenic overexpression is BH3 mimicry, the design of small molecule inhibitors that can mimic the binding interactions of the BH3 domain within the hydrophobic binding grooves to promote the release of the pro-apoptotic proteins and restore apoptosis. Navitoclax was among the first potent BH3 mimetics to enter clinical trials due to its pan-inhibitor properties against the various anti-apoptotic proteins. Navitoclax was shown to produce a toxic side effect, thrombocytopenia, that involved the pre-mature death of platelet cells in animals and patients due to the inhibition of BCL-$X_L$. The development of Venetoclax, a BCL-2 selective inhibitor, overcame the toxicity of Navitoclax and has been FDA approved for chronic lymphocytic leukemia. Venetoclax's efficacy has been shown to weaken when administered as a mono-therapy since cancer cells can develop resistance to the treatment through the overexpression of MCL-1, thus igniting the pursuit towards the development of MCL-1 selective inhibitors. Presently, there are a wide array of MCL-1 selective inhibitors within the literature and others, such as AZD5991, undergoing clinical trials.

Combination therapies employing both MCL-1 and BCL-2 selective inhibitors have also demonstrated promising results since this treatment strategy simultaneously targets multiple signaling pathways involved in the pathogenesis of a disease, such as cancer, to overcome resistance mechanisms that monotherapies are inefficient at combating. This treatment strategy has also been shown to reduce the cytotoxic effects of the active drug via inflammation reduction or neuroprotection. Though combination therapies possess significant advantages over monotherapies, they still possess drawbacks that can hinder treatment. Combination therapies possess a higher chance of inducing acute and delayed toxicities due to potential drug-drug interactions within the body, hence leading to more complex dosing regimens that are not optimal for patient administration. Chemotherapies that involve the administration of multiple single-target drugs also have the chance at becoming ineffective due to the development of resistance mechanisms against one of the drugs, thus lowering the efficacy of the treatment. Another caveat of combination therapies is that their efficacy relies upon all the drugs to be evenly distributed within the body and enter into the cell simultaneously, which is a challenging task if not all the drugs possess similar administration routes, metabolic profiles, cellular permeabilities or half-lives. Properly demonstrating drug safety in combination therapies is also problematic since the drugs within the treatment must be shown to be safe on their own and then in combination with others, thus hindering the advancement of the therapy into the clinic.

The use of polypharmacology, the design of a single molecule that selectively targets multiple proteins or signaling pathways, has been implemented in drug design to overcome the drawbacks of combination therapies. Compounds possessing selectivity for multiple targets are more difficult to acquire resistance towards due to the need to modify multiple pathways or proteins. Additionally, molecules that are polypharmacological tend to display more favorable pharmacokinetic and safety profiles when compared to combination therapies since only a single molecule is administered instead of multiple compounds that can form complex interactions with each other. The development of dosing schedules for a single molecule is also less complex than preparing dosing schedules for combination therapies and overall leads to more patient-friendly dosing regimens. The administration of a single agent also removes the concerns of unequal distribution within the body and potential drug-drug interactions that are present within combination therapies. Regulatory requirements are also less challenging to address for a single agent than with combination therapies, thus promoting quick assessment of the agent's therapeutic potential and advancement to the clinic.

In order to combat the oncogenic overexpression of both BCL-2 and MCL-1 in cancer cells, a polypharmacological design approach to synthesize potent dual inhibitors against certain proteins of interest was used. In some embodiments, such inhibitors would possess dual affinity for MCL-1 and BCL-2, and/or also possess a lower chance of inducing thrombocytopenia in in vivo studies due to their low BCL-$X_L$ affinities. Additionally, such inhibitors will possess the advantages associated with polypharmacology to provide novel compounds that are not dependent on other drugs to elicit their chemotherapeutic effects. The design, synthesis and results of our indazole-based dual MCL-1 and BCL-2 inhibitors is discussed herein.

The overall design for dual-selective BCL-2 and MCL-1 inhibitors was adapted from previously identified selective inhibitors (FIG. 1). To achieve potent MCL-1 affinity within the dual inhibitors, design elements present within Fesik et al's indole-based MCL-1 selective inhibitors were implemented. These inhibitors achieved potent MCL-1 affinity through their ability to bind deep into MCL-1's p2 pocket with their 4-chloro-3,5-dimethylphenyl motif at the 3-position. Additional functional groups that were shown to further improve their binding affinities were a carboxylic acid motif at the 2-position, which engaged in hydrogen bonding interactions with MCL-1's Arg263 residue, and a chlorine at the 6-position that was able to occupy a small hydrophobic space between the p2/p3 pockets. Hence, these pharmacophores were implemented onto heterocyclic cores that were structurally similar to an indole since they will provide a degree of novelty to our designs and an indole core is well accommodated in MCL-1's binding groove. Dual inhibitors from both a benzimidazole and indazole core since both heterocycles not only resemble an indole in structure, but can also potentially participate in additional hydrogen bonding interactions with arginine residues through their unalkylated core nitrogens, further improve binding affinity. The 4-chloro-3,5-dimethylphenyl motif was installed onto the N-2 nitrogen of the indazole core to maintain the "neighboring" relationship between the 4-chloro-3,5-dimethylphenyl motif and the acidic group seen in the MCL-1 indole inhibitors (FIG. 1). A chlorine was attached at the 5-position of the indazole core to mimic the anti-relationship between the chlorine and p2 pharmacophore in the indole inhibitors. The benzimidazole ring was not chlorinated due to the challenges it would have introduced in the purification of the isomers after the installation of the 4-chloro-3,5-dimethyl group. Computational docking simulations were performed with both the N-2 alkylated indazole and the alkylated benzimidazole acids. Both compounds were predicted to have favorable binding energies in both the MCL-1 and BCL-2 hydrophobic grooves.

Venetoclax achieved its BCL-2 selectivity through its azaindole motif, which participated in hydrogen bonding interactions with residues Asp103 and Arg107 in BCL-2. The BCL-$X_L$ affinity of venetoclax was more than 100-fold lower since it possessed a Glu96 residue at the location of BCL-2's Asp103 residue, which the azaindole core cannot reach to engage in hydrogen bonding. The X-ray crystal structure of venetoclax bound into BCL-2 further revealed that the azaindole motif captured hydrogen bonding interactions with Asp103 and Arg107 in BCL-2's p4 binding pocket. In addition to the azaindole motif, venetoclax also possessed an acylsulfonamide linkage that allowed its nitroaryl ring to project and bind into BCL-2's p4 pocket, thus further improving BCL-2 binding affinity. Thus, it was decided to replace the carboxylic acid group on heterocyclic cores with an acylsulfonamide since it will allow the inhibitors to reach into BCL-2's p4 pocket to improve BCL-2 binding affinity. An acylsulfonamide is also a bioisostere of a carboxylic acid, thus the designs herein will still maintain an acidic functional group that is capable of engaging in hydrogen bonding interactions with conserved arginine residues. Instead of attaching the azaindole motif to the cores of the dual inhibitors, as seen in venetoclax, it was chosen to link functional groups that could mimic the hydrogen bonding interactions of the azaindole motif to the nitroaryl ring of the sulfonamide. The attachment of these groups onto at this position enhances their ability to bind into BCL-2's p4 pocket and potentially engage in hydrogen bonding interactions with Asp103 and Arg107.

The dual MCL-1/BCL-2 inhibitor designs described herein contain both an indazole and benzimidazole core that have been functionalized to possess a chlorine, 4-chloro-3, 5-dimethylphenyl motif and an acidic functional group to increase their MCL-1 binding affinities. Analogues of these cores will also possess acylsulfonamide linkers between the heterocyclic cores and functionalized nitroaryl rings to promote occupation of BCL-2's p4 pocket to further enhance their BCL-2 binding affinities.

Synthesis of the Indazole and Benzimidazole Cores: the synthesis of the functionalized benzimidazole core is outlined in Scheme 2. The synthesis consists of three steps: first 1H-benzimidazole-2-carboxylic acid (1) underwent an esterification with thionyl chloride in methanol to create the methyl ester (2), then the methyl ester was subjected to an $SN_2$ reaction with 5-(3-bromopropoxy)-2-chloro-1,3-dimethylbenzene (3) to create the N-alkylated benzimidazole (4), which then underwent a saponification with NaOH to produce the N-alkylated-benzimidazole-2-carboxylic acid final molecule (5).

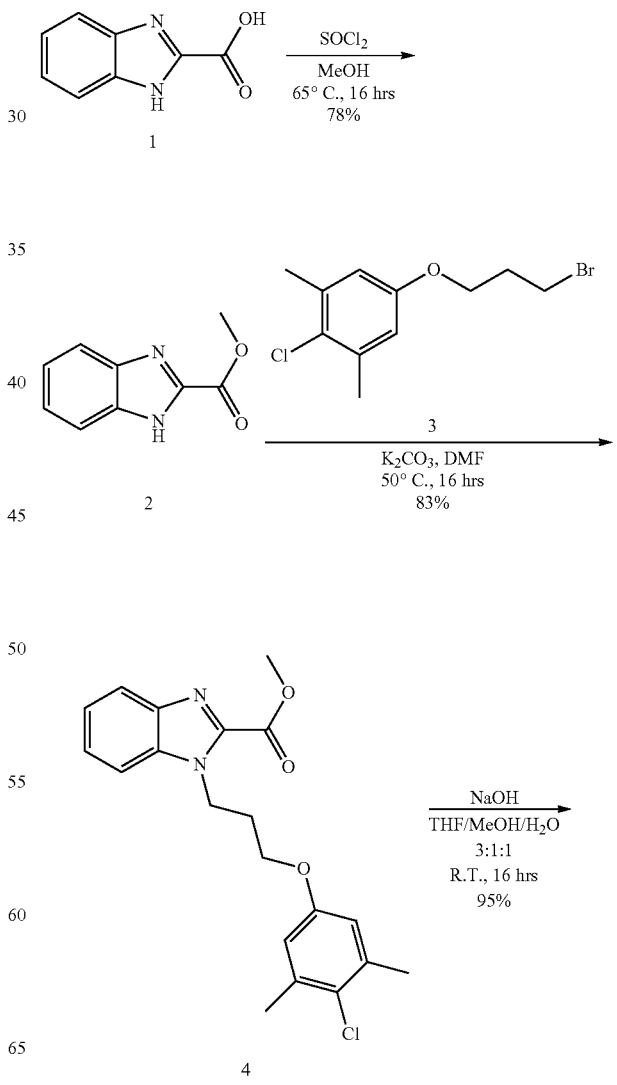

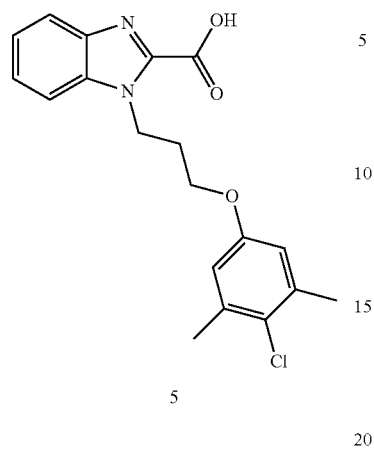

5

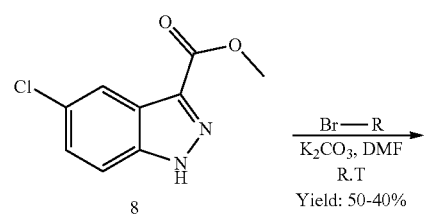

8

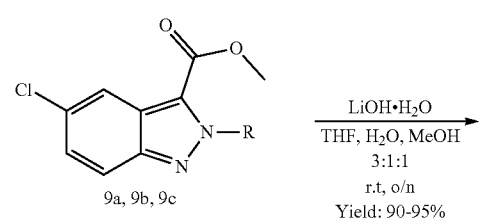

9a, 9b, 9c

The synthesis of the functionalized indazoles is outlined in Scheme 3. 5-chloroisatin (6) was hydrolyzed open, subjected to a diazotization and then reduced with tin (II) chloride to form the hydrazine, which then intramolecularly attacked the aryl ketone to afford the indazole carboxylic acid (7). The indazole carboxylic acid then underwent a methyl esterification with thionyl chloride to create the ester 8, which was subjected to an $SN_2$ reaction with alkyl bromides to produce the N2-alkylated products (9a, 9b, 9c). The esters were then hydrolyzed to create the carboxylic acids (10, 11, 12), which were then subjected to coupling reactions with various sulfonamides (13-30) to produce the fully functionalized indazoles (31-48).

Alkylating an indazole core under the conditions presented within Scheme 3 produced two indazole isomers: the N1-alkylated and the desired N2-alkylated molecules. The isomers were able to be separated via column chromatography and were identified by their NMR spectra. It has been shown that when an indazole is alkylated under these conditions, the isomers can be distinguished from each other by their N—CH$_2$—R peaks since the N1-alkylated isomer's N—CH$_2$—R peak is 0.5 ppm more upfield than the N2-isomer's peak. The same chemical shift differences between the two isomers collected were observed, and were able to accurately identify the N2-alkylated isomer.

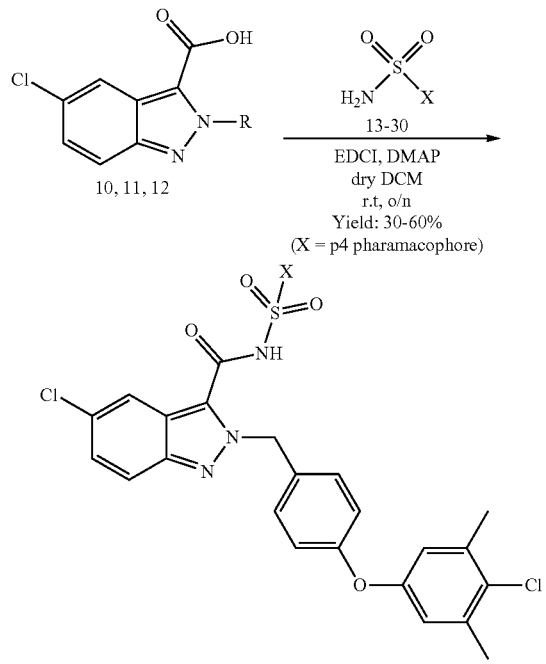

10, 11, 12

31-48

Scheme 3: Synthesis of the N2-alkylated indazole core

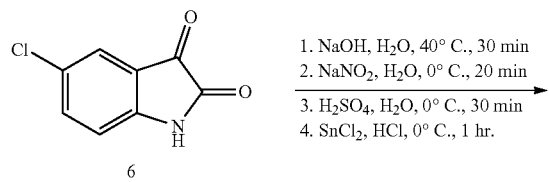

1. NaOH, H$_2$O, 40° C., 30 min
2. NaNO$_2$, H$_2$O, 0° C., 20 min
3. H$_2$SO$_4$, H$_2$O, 0° C., 30 min
4. SnCl$_2$, HCl, 0° C., 1 hr.

6

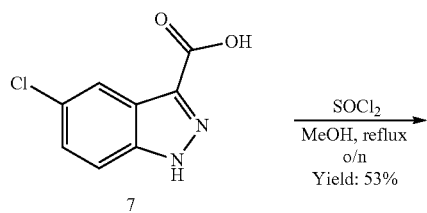

7

SOCl$_2$
MeOH, reflux
o/n
Yield: 53% a: R = 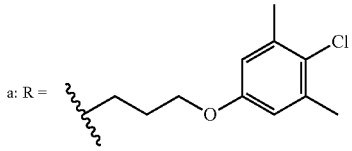

b: R = 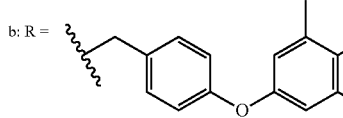

c: R = 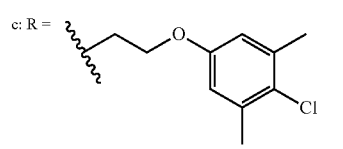

115
-continued
p4 pharmacophores:
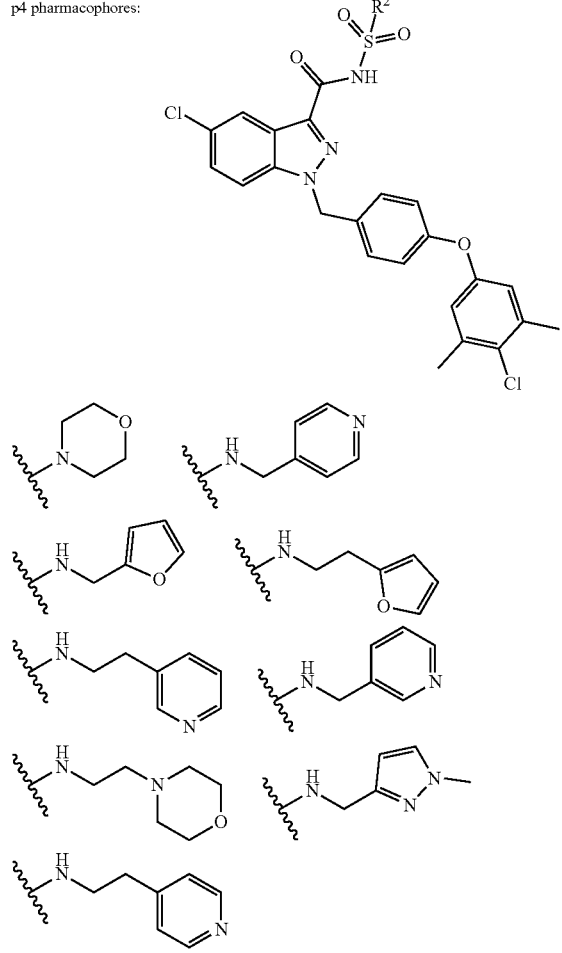
p2 pharmacophores:
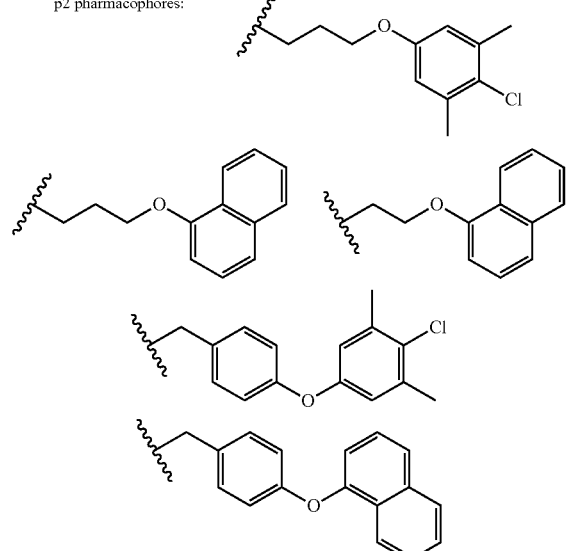
para pharmacophores:
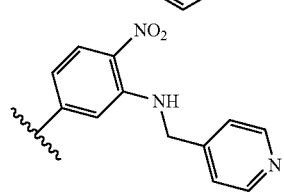
116
-continued
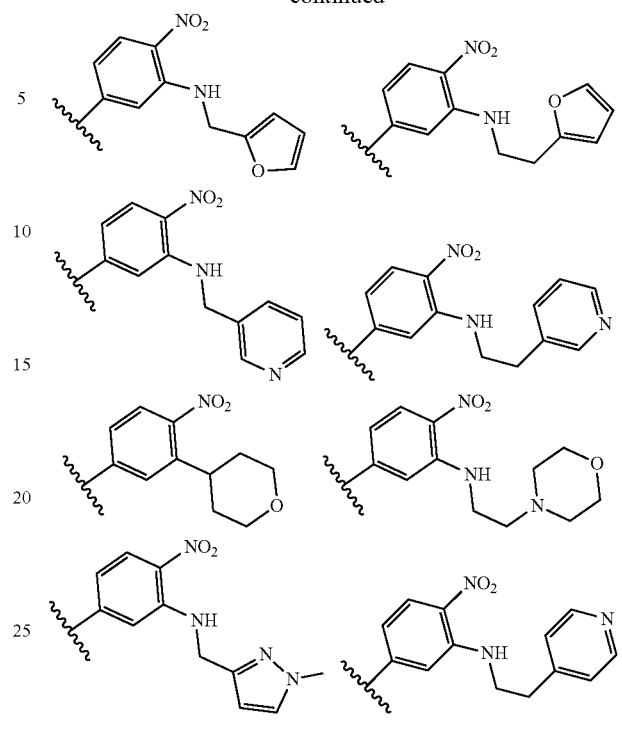
Scheme 4: Synthesis of benzimidazole compounds
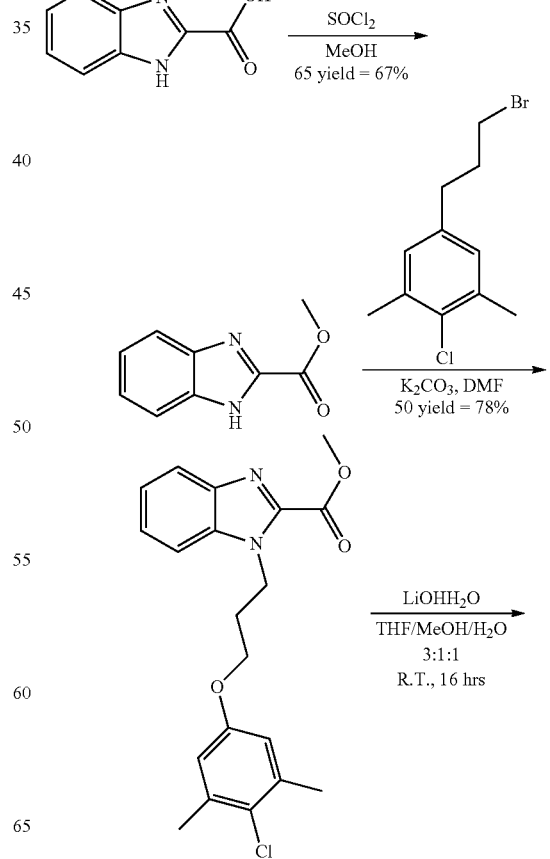

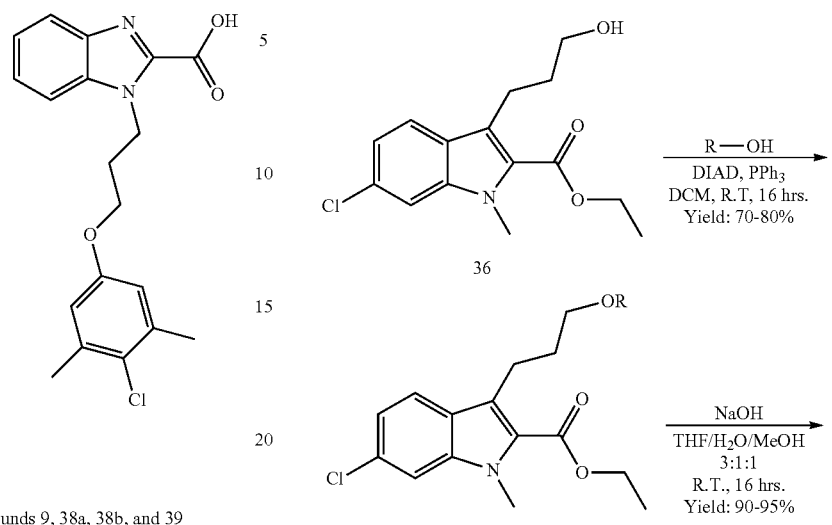
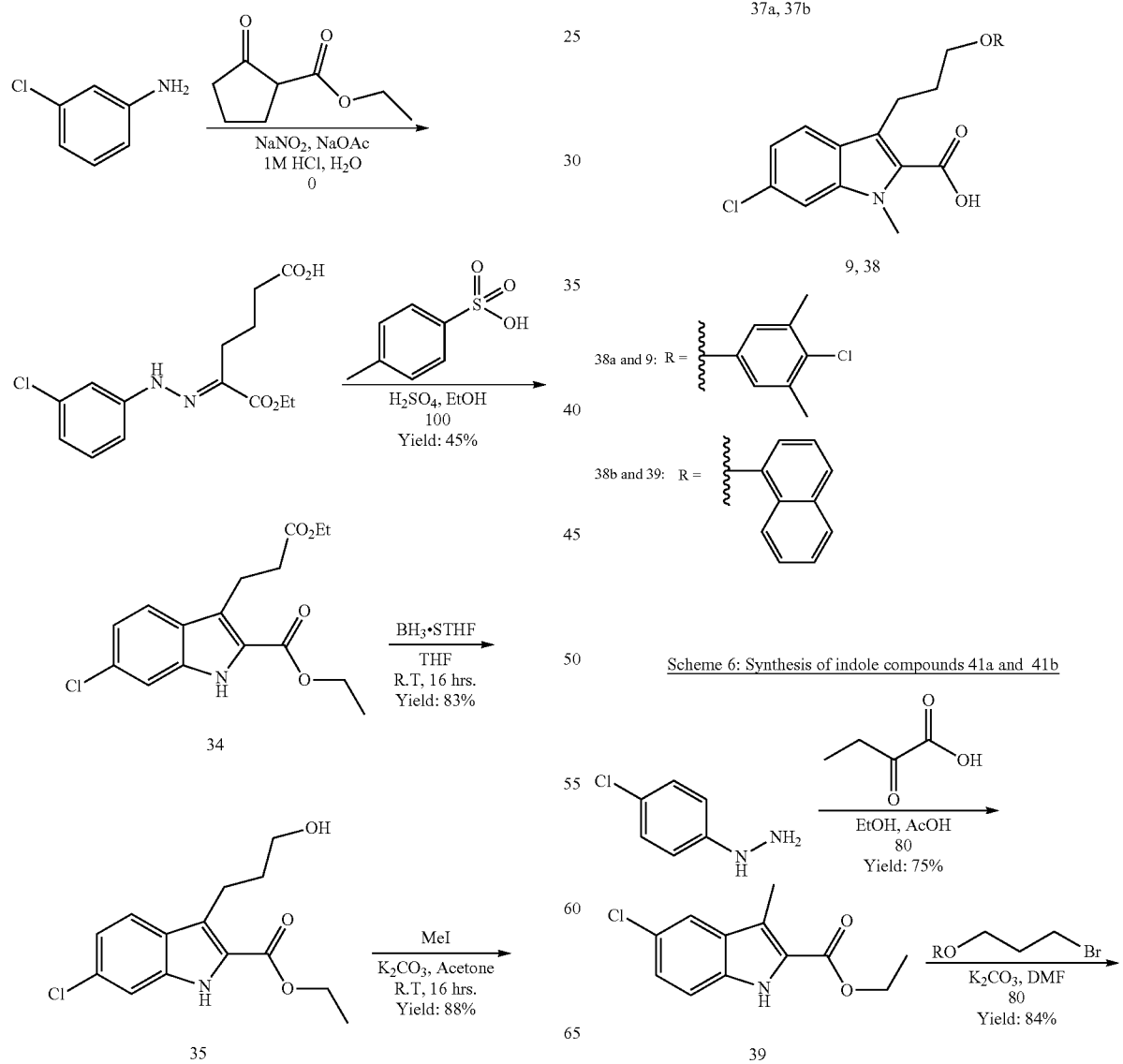

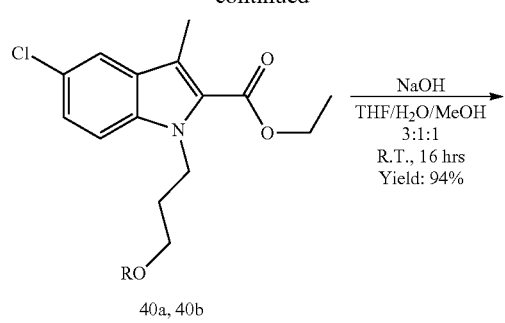
40a, 40b
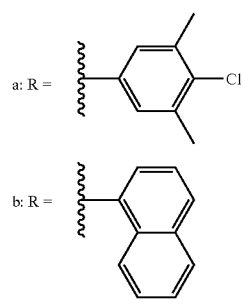
41a, 41b
a: R = 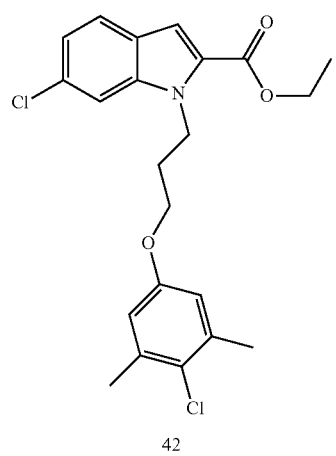
b: R = (naphthalen-1-yl)
Scheme 7: Synthesis of indole compound 43
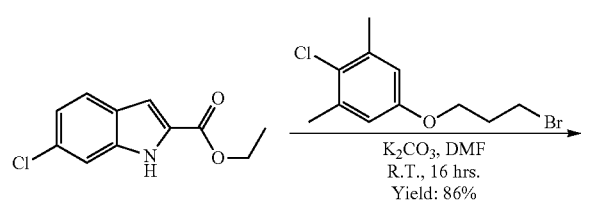
42
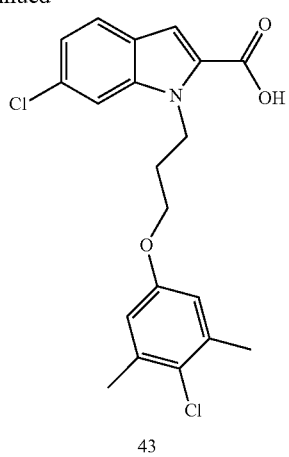
43
Scheme 8: Synthesis of generic indole compounds
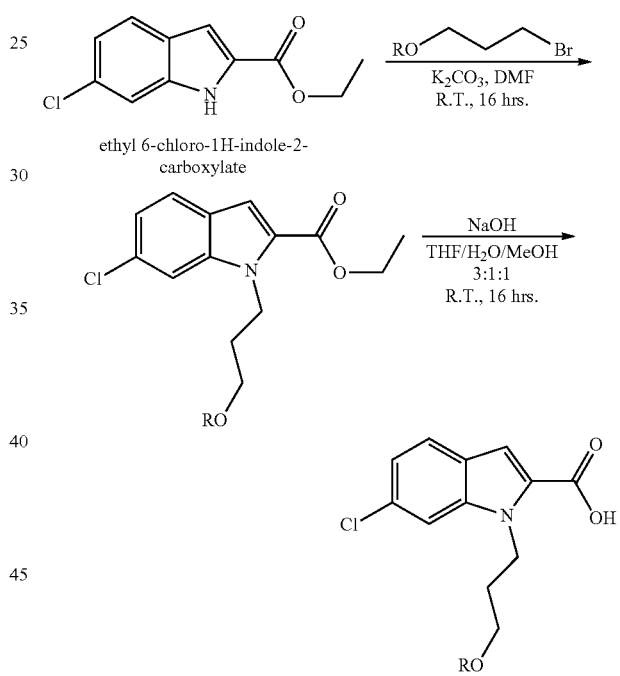
Scheme 9: Synthesis of indole compound 46
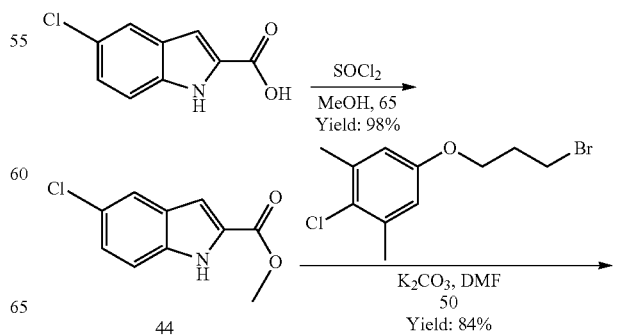
44

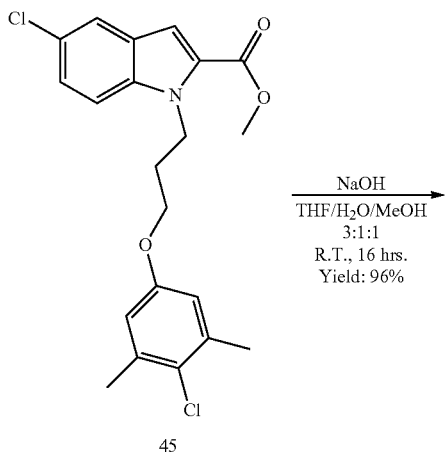
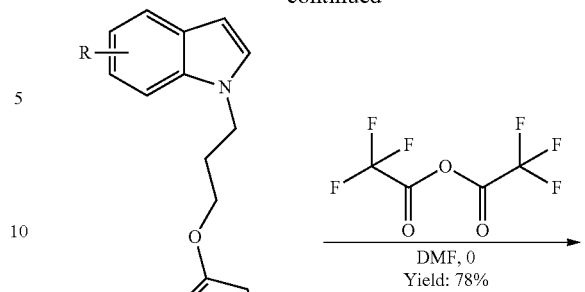
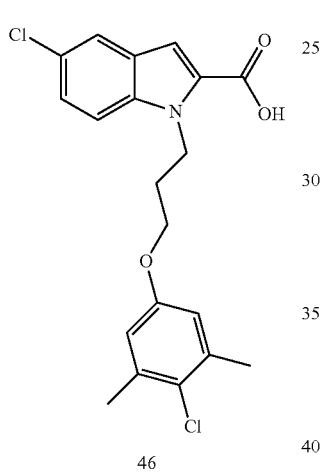
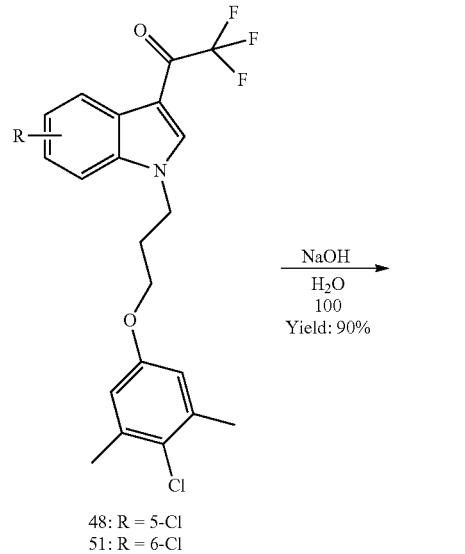
Scheme 10: Synthesis of indole compounds 49 and 52
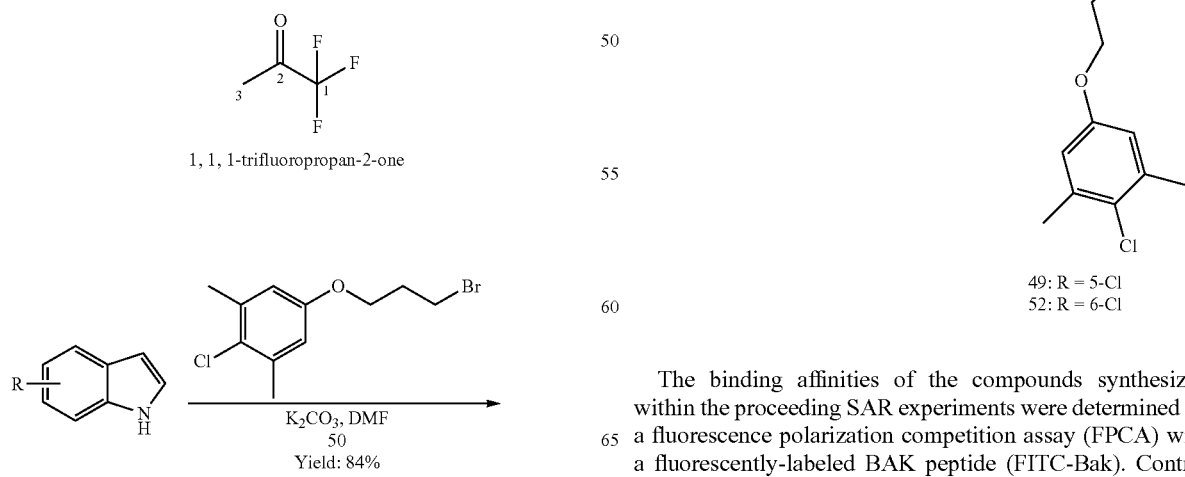
The binding affinities of the compounds synthesized within the proceeding SAR experiments were determined by a fluorescence polarization competition assay (FPCA) with a fluorescently-labeled BAK peptide (FITC-Bak). Control compounds S-63845, ABT-737 and one of Fesik et al's indoles were used to validate the FPCA conditions, all of which displayed binding affinities consistent with the literature (Table 4).

TABLE 4

FPCA Data for Control Compounds

| Compound | MCL-1 $K_i$ (μM) | BCL-2 $K_i$ (μM) | BCL-$X_L$ $K_i$ (μM) |
|---|---|---|---|
| S-63845 | 0.039 ± 0.01 | NA | NA |
| ABT-737 | NA | <0.04 | <0.04 |
| Fesik Indole | 0.247 ± 0.03 | >10.00 | 1.202 ± 0.16 |

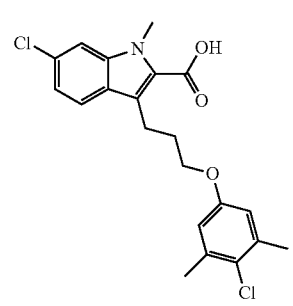

Initial SAR experiments focused on determining whether the heterocyclic cores within our designs displayed either improved or similar MCL-1 binding affinities when compared to Fesik et al's indoles (Table 5). MCL-1 binding affinity was chosen to be the focus within these initial studies since it requires more potent inhibitors than the other Bcl-2 anti-apoptotic proteins to elicit a cytotoxic response in cancer cells. Additional SAR experiments are illustrated in FIG. 11.

TABLE 5

| I.D. | Structure | MCL-1 $K_i$ (μM) |
|---|---|---|
| Fesik Indole | 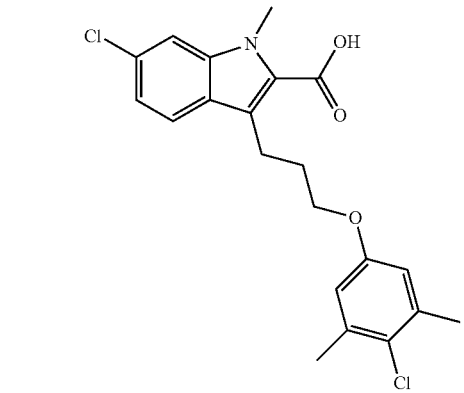 [SMILES: Cc1cc(OCCCc2c(C(=O)O)n(C)c3cc(Cl)ccc23)cc(C)c1Cl] | 0.247 ± 0.03 |

TABLE 5-continued

| I.D. | Structure | MCL-1 $K_i$ (μM) |
|---|---|---|
| 5 | 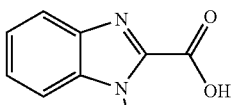 | >10.00 |
| 10 | 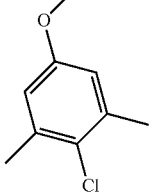 | >10.00 |
| 11 | 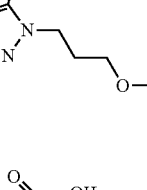 | >10.00 |
| 12 | 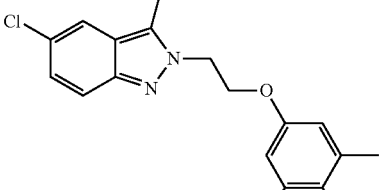 | 2.36 ± 0.29 |
| 49 | 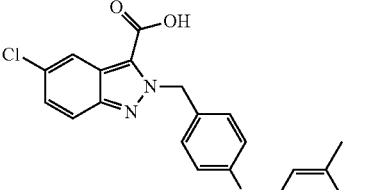 | 1.755 ± 0.55 |

The binding affinity of the benzimidazole core was examined. The benzimidazole carboxylic acid (5) was shown to possess poor affinity for MCL-1 ($K_i$>10.00 μM) according to our FPCA conditions. We then examined the potency of the N-2 alkylated indazole core (10). The FPCA also concluded that 10 also displayed poor MCL-1 binding affinity ($K_i$>10.00 µM). Given the poor affinities of both the N-2 alkylated indazole and benzimidazole core, linkers other than a propyl chain were explored to improve MCL-1 binding affinity. The N-2 alkylated indazole core was chosen for these linker studies due to its accessible synthesis and easier purification, when chlorinated, over the benzimidazole. First, the alkyl linker was replaced with an ethyl chain (11) to determine if MCL-1 affinity could be improved with a shortened alkyl linker. Similar to the propyl analogue, 11 also possessed poor affinity for MCL-1 ($K_i$>10.00 µM). The incorporation of phenyl linkers onto p2 pharmacophores have been shown to be successful in the promotion of potent MCL-1 binding affinities, hence they are explored within SAR studies. Once a benzyl linker was incorporated (12), MCL-1 affinity was improved to the low-micromolar range ($K_i$,32 2.36±0.29 µM). In order to rationalize how a benzyl linker improved MCL-1 affinity, a docking model of 12 bound into the hydrophobic groove of MCL-1 was developed (FIG. 2). The docking model predicted that 12's core bound into the shallow region of MCL-1's p2 pocket while the benzyl pharmacophore reached deep into the p2 pocket. The carboxylic acid was predicted to project towards the p4 pocket, while the chlorine at the 5-position was bound into a small hydrophobic pocket within the groove. Similar to a previous docking model, the 6-position projected towards a larger pocket within the binding groove that could more readily accommodate a chlorine. It was then explored whether the placement of the chlorine in the 6-position may further enhance MCL-1 affinity. A 6-chloroindazole analogue (49) was synthesized and elicited a slight improvement in MCL-1 affinity ($K_i$=1.76±0.55 µM) when compared to the 12. Since 49 did not possess a significant improvement over 12 and suffered from lower yields during its synthesis (yield<32% after cyclization), 12 was chosen to serve as the starting material in proceeding SAR studies.

Following the design rationale, acylsulfonamides were installed at the 3-position of the N-2 alkylated indazole core to determine if the p4 pocket can be reached, as seen in venetoclax and Fesik et al's indole acylsulfonamides (Table 6). The first analogue within this study (31) was synthesized to both validate our docking models' predictions that the 3-position of the indazole core projected towards the p4 pocket and support our hypothesis that occupation of the p4 pocket would lead to enhanced BCL-2 affinity. Indeed, when compared to 12 (MCL-1 $K_i$=2.36±0.29 µM, BCL-2 $K_i$=1.448±0.075 µM), 31 possessed an improved affinity for MCL-1 ($K_i$=1.12±0.17 µM) and BCL-2 ($K_i$=0.51±0.10 µM). Analogue 31 also possessed a weaker affinity for BCL-$X_L$ ($K_i$>10.00 µM). With the improvement in BCL-2 and MCL-1 affinity from the installment of an acylsulfonamide group at the 3-position, replacement of the 4-chlorophenyl motif with various substituted-nitroaryl rings was pursued in order to capture the key binding interactions with Asp103 and Arg107 in BCL-2's p4 pocket to further enhance BCL-2 affinity. Nitroaryl rings were implemented with our p4 pharmacophore designs since they have been shown to bind into BCL-2's p4 pocket, as seen in venetoclax, when attached to acylsulfonamide linkers. Also, fluorinated nitroaryl rings readily undergo functionalization reactions under SNAr conditions when the nitro-group is either ortho orpara to the fluorine due to the nitro-group's strong electron-withdrawing property, thus allowing the quick generation of our p4 pharmacophores.

TABLE 6

FPCA binding data for the 3-acylsuylfonamide SAR studies (NA = No activity)

| I.D. | $R^1$ | MCL-1 $K_i$ (µM) | BCL-2 $K_i$ (µM) | BCL-$X_L$ $K_i$ (µM) |
|---|---|---|---|---|
| 31 | 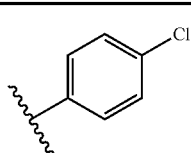 | 1.20 ± 0.17 | 0.51 ± 0.10 | >10.00 |

TABLE 6-continued

FPCA binding data for the 3-acylsuylfonamide SAR studies
(NA = No activity)

| I.D. | R¹ | MCL-1 $K_i$ (μM) | BCL-2 $K_i$ (μM) | BCL-X$_L$ $K_i$ (μM) |
|---|---|---|---|---|
| 32 | 4-morpholino-3-nitrophenyl | 1.32 ± 0.16 | 0.53 ± 0.09 | 7.99 ± 2.43 |
| 33 | 4-(2-morpholinoethylamino)-3-nitrophenyl | 1.61 ± 0.10 | 0.42 ± 0.16 | NA |
| 34 | 4-(furan-2-ylmethylamino)-3-nitrophenyl | 1.30 ± 0.11 | 0.57 ± 0.05 | >10.00 |
| 35 | 4-(2-(furan-2-yl)ethylamino)-3-nitrophenyl | 1.28 ± 0.15 | 0.62 ± 0.14 | 3.40 ± 1.19 |
| 36 | 4-((1-methyl-1H-pyrazol-3-yl)methylamino)-3-nitrophenyl | 1.57 ± 0.14 | 0.60 ± 0.11 | 3.85 ± 0.73 |

TABLE 6-continued

FPCA binding data for the 3-acylsuylfonamide SAR studies
(NA = No activity)

| I.D. | R¹ | MCL-1 $K_i$ (μM) | BCL-2 $K_i$ (μM) | BCL-$X_L$ $K_i$ (μM) |
|---|---|---|---|---|
| 37 | (2-nitro-4-linked phenyl)-NH-CH₂-(pyridin-3-yl) | 1.12 ± 0.07 | 1.18 ± 0.14 | 4.42 ± 0.53 |
| 38 | (2-nitro-4-linked phenyl)-NH-CH₂CH₂-(pyridin-3-yl) | 1.46 ± 0.13 | 0.46 ± 0.05 | >10.00 |
| 39 | (2-nitro-4-linked phenyl)-NH-CH₂-(pyridin-4-yl) | 1.65 ± 0.18 | 1.52 ± 0.31 | >10.00 |
| 40 | (2-nitro-4-linked phenyl)-NH-CH₂CH₂-(pyridin-4-yl) | 1.77 ± 0.29 | 0.66 ± 0.18 | >10.00 |

The p4 pharmacophores were first attached to the nitroaryl rings, via methyl or ethyl alkyl chains, at the para-position to determine that position's affinity and the optimal alkyl chain for binding into the p4 pocket (Table 6). Morpholine analogues 32 (MCL-1 $K_i$=1.32±0.16 μM, BCL-2 $K_i$=0.53±0.09 μM, BCL-$X_L$=7.99±2.43 μM) and 33 (MCL-1 $K_i$=1.61±0.10 μM, BCL-2 $K_i$=0.42±0.16 μM, BCL-$X_L$>10.00 μM) possessed similar degrees of MCL-1 and BCL-2 affinities in regards to 31. Furan analogues 34 and 35 also demonstrated MCL-1 and BCL-2 affinities that were seen in the previous analogues (MCL-1 $K_i$'s~1.30 μM and BCL-2 $K_i$'s~0.60 μM), with 35 possessing a greater affinity for BCL-$X_L$ ($K_i$=3.40±1.20 μM) than 34 ($K_i$>10.00 μM). A pyrazole derivative, 36, displayed binding affinities for all three proteins that were similar to 35. Pyridine analogues 37 (MCL-1 $K_i$=1.12±0.07 μM, BCL-2 $K_i$=1.18±0.14 μM) and 38 (MCL-1 $K_i$=1.46±0.13 μM, BCL-2 $K_i$=0.46±0.05 μM) were also synthesized. Though both analogues retained MCL-1 affinities that resembled the other analogues within this study, 37 displayed a 2.5-fold weaker affinity for BCL-2. Additionally, pyridine analogues where the nitrogen was in the para-position of the pyridine ring, 39 and 40, were also synthesized to examine whether the position of the nitrogen had a significant effect on BCL-2 affinity. Both compounds produced BCL-2 and MCL-1 binding affinities that were similar to their meta-pyridine counterparts.

Proceeding SAR examined how the attachment of the p4 pharmacophores at the meta-position of the nitroaryl rings effected BCL-2 binding affinity (Table 7). Overall, most of the meta-analogues possessed similar binding affinities when compared to their para-counterparts. One notable difference was that the meta-pyrazole analogue 44 demonstrated a slightly weaker affinity to BCL-$X_L$ ($K_i$=7.41±2.56 µM) when compared to its para-counterpart 36. Additionally, analogues 43, 44 and 46 possessed weaker affinities towards BCL-$X_L$ than their para-counterparts. Overall, enhanced MCL-1 and BCL-2 binding affinities were achieved through the occupation of both the p4 and p2 pockets, while BCL-$X_L$ affinity remained low or undetectable.

TABLE 7

FPCA binding data for the SAR studies with the para-nitrophenylacylsulfonamides
(NA = No activity)

| ID | R¹ | MCL-1 $K_i$ | BCL-2 $K_i$ | BCL-$X_L$ $K_i$ |
|---|---|---|---|---|
| 41 | [aryl with NO₂ and morpholine] | 2.30 ± 0.17 | 0.90 ± 0.25 | 6.66 ± 3.14 |
| 42 | [aryl with NO₂ and NH-CH₂-furan] | 1.68 ± 0.33 | 0.96 ± 0.08 | >10.00 |
| 43 | [aryl with NO₂ and NH-CH₂CH₂-furan] | 2.16 ± 0.61 | 0.84 ± 0.23 | >10.00 |
| 44 | [aryl with NO₂ and NH-CH₂-methylpyrazole] | 1.95 ± 0.18 | 0.71 ± 0.11 | 7.41 ± 2.56 |

TABLE 7-continued

FPCA binding data for the SAR studies with the para-nitrophenylacylsulfonamides
(NA = No activity)

| ID | R[1] | MCL-1 $K_i$ | BCL-2 $K_i$ | BCL-X$_L$ $K_i$ |
|---|---|---|---|---|
| 45 | (3-pyridylmethylamino-nitrophenyl) | 1.00 ± 0.10 | 1.22 ± 0.50 | >10.00 |
| 46 | (3-pyridylethylamino-nitrophenyl) | 1.46 ± 0.13 | 0.46 ± 0.05 | >10.00 |
| 47 | (4-pyridylmethylamino-nitrophenyl) | 1.36 ± 0.21 | 0.71 ± 0.25 | >10.00 |
| 48 | (4-pyridylethylamino-nitrophenyl) | 1.42 ± 0.11 | 0.77 ± 0.18 | NA |

Once the binding data for the N-2 alkylated indazoles was obtained it was decided to determine if the N-1 alkylated isomers possessed similar or improved affinities. The N1-alkylated isomers possess more potent binding affinities since the lone pair of electrons on N-2 nitrogen can coordinate with the acidic functional group to form stronger hydrogen bonding networks with conserved arginine residues along the binding groove, as seen in WEHI-539. According to a small SAR study (Table 8), the N-1 alkylated indazole acid (50) possessed an improved affinity for MCL-1 when compared to the N-2 isomer 12. However, once acylsulfonamides were grafted onto the 3-position of 50, MCL-1 affinity decreased. Although 51 possessed a slight decrease in MCL-1 affinity when compared to 32, analogue 52 suffered a substantial loss when compared to 37. The BCL-2 binding affinities for both 51 and 52 were within the nanomolar range and did not offer improvement when compared to their N-2 counterparts. Both 51 and 52 also possessed no affinity for BCL-X$_L$, thus signifying that changing the alkylation position between the two core nitrogens had no effect on BCL-X$_L$ affinity.

TABLE 8

MCL-1 FPCA data for the N-1-alkylated isomers

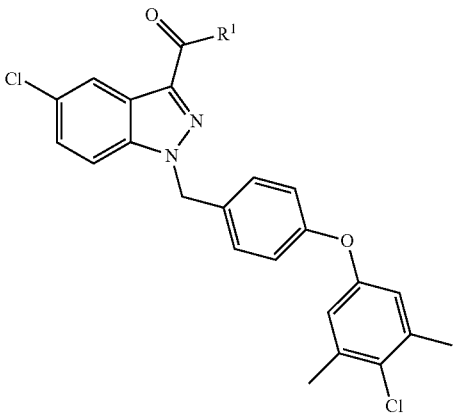

| I.D | R¹ | MCL-1 $K_i$ (μM) | BCL-2 $K_i$ (μM) | BCL-$X_L$ $K_i$ (μM) |
|---|---|---|---|---|
| 50 | OH | 1.58 ± 0.36 | — | — |
| 51 | (nitro-morpholino-aryl sulfonamide) | 2.219 ± 0.20 | 0.62 ± 0.12 | NA |
| 52 | (nitro-pyridylmethylamino-aryl sulfonamide) | >10.00 | 0.69 ± 0.11 | NA |

The results of the SAR studies with the indazole inhibitors, when compared to the indole precursors, showed that the indazoles possessed a lower binding affinity towards MCL-1 while some demonstrated a slight improvement in BCL-2 affinity. Additionally, the indazole inhibitors possessed either no affinity or a significantly lowered affinity towards BCL-$X_L$ when compared to MCL-1 and BCL-2. The improved BCL-2 affinity could arise from the p4 pharmacophores capturing key hydrogen bonding interactions within the MCL-1 and BCL-2 binding grooves. The improved MCL-1 affinity from the benzyl linker over the alkyl linkers could be due to the plasticity of MCL-1's binding groove since MCL-1's p2 pocket has been shown to tolerate large, hydrophobic groups. Also, the benzyl linker may be tolerated by both MCL-1 and BCL-2 due to its less degrees of freedom over the alkyl linkers. Additional SAR experiments examine how well the N-1 alkylated isomer of 7 (propyl linker) binds to MCL-1 since the benzyl pharmacophore further increased MCL-1 affinity when attached at the N-1 over the N-2 position. Binding mode experiments, such as X-ray crystallography or 2D NMR, are performed in order to support these binding theories.

The installation of the p4 pharmacophores further improved the indazoles' affinities for both MCL-1 and BCL-2. Among the p4 pharmacophore SAR studies, a slight increase in MCL-1 and BCL-2 binding affinity was observed among the indazole analogues that possessed the p4 pharmacophores at the para-position of the nitroaryl ring when compared to their meta-counterparts. Hence, the para-p4 pharmacophores were pursued in the N-1 alkylated indazole SAR study. The N-1 alkylated indazole acid (31) possessed a slightly increased affinity towards MCL-1 when compared to 11; however, once acylsulfonamides were introduced onto the N-1 alkylated indazoles (32,33), MCL-1 affinity was decreased below their N-2 counterparts (14,19). BCL-2 affinity did not suffer among the N-1 alkylated indazole acylsulfonamides. A possible explanation for these results is that the N-1 alkylated indazoles need to re-orientate themselves to bind into MCL-1's groove, thus shifting the p4 pharmacophores further away from the p4 pocket. Additional SAR studies with the meta-pharmacophores need to be performed to investigate this rationale since the meta-position may still be able to bind into MCL-1's p4 pocket when the p2 pharmacophore is attached to the N-1 position. The synthesis of ortho-analogues was not completed due to low or no yields and difficult purifications. BCL-$X_L$ affinity was either not observed or lower when compared to both MCL-1 and BCL-2 among all the acylsulfonamide indazole analogues. Future directions for the indazoles involve testing the efficacy in a variety of leukemia and melanoma cancer cell lines.

The indazoles were able to demonstrate enhanced MCL-1 and BCL-2 affinities over BCL-X$_L$. The potency of the indazoles is not at the necessary level to be efficacious in in vivo models since low nanomolar to picomolar MCL-1 binding affinity is required to promote significant efficacy. The need for highly potent MCL-1 inhibitors is due to not only the short half-life of MCL-1, but also due to the strong binding affinity between MCL-1 and the pro-apoptotic proteins. The successful synthesis of the indazoles further provides evidence that dual selectivity for MCL-1 and BCL-2 can be achieved. Once the binding mechanisms behind the indazoles are identified, dual inhibitors are synthesized that possess the necessary pharmacophores to enhance potency against MCL-1 and BCL-2 for in vivo testing.

Materials:

All chemical reagents are ACS grade or higher unless otherwise indicated. The D$_2$O, D$_6$-DMSO, and $^{15}$NH$_4$Cl were purchased from Cambridge Isotope Laboratories, Inc. (Andover, Mass.). All other chemicals were purchased from Sigma-Aldrich (St. Louis, Mo.). Compounds 1, 3, 6 and the alkyl bromides were all commercially available.

Protein Purification:

recombinant human Mcl-1 residues 172 to 327 (MCL1$^{172-327}$) protein in E. coli of high purity (>95% pure) is expressed and purified and milligram quantity for use in all the applications proposed including FPCA and stable isotopically labeled ($^{15}$N) protein for NMR studies. The pLM302 expression vector was constructed to produce His6-MBP (maltose binding protein) tagged recombinant human Mcl-1 residues 172 to 327 (MCL1$^{172-327}$) in HMS174 (DE3) cells (EMD Millipore) using either LB or minimal media supplemented with $^{15}$NH$_4$Cl to produce unlabeled or $^{15}$N-labeled MCL1, respectively. The tagged protein was initially purified from the crude cell lysate by IMAC chromatography (GE Healthcare Life Sciences), and after dialysis to remove the imidazole the affinity tag was cleaved using PreScission Protease (GE Healthcare Life Sciences). A Sephacryl S-200 size exclusion column was used as a final purification step before the protein was concentrated with a 10,000 MWCO centrifugal filter concentrator (EMD Millipore). The concentrations of the proteins were determined using the Bio-Rad Protein Assay (Bio-Rad Inc., Hercules, Calif.) using BSA of a known concentration as the standard (Pierce). The purity of the protein was confirmed using SDS-PAGE analysis and NMR HSQC experiments were done to confirm the protein was properly folded.

Peptides:

A 6-aminohexanoic acid linker was conjugated to the N-terminus of the Bak BH3 peptide amino acids 71 to 89 (GQVGRQLAIIGDDINR), capped with fluorescein (on the amino group of the linker), and the peptide was amidated on the C-terminus to give FITC-Ahx-GQVGRQLAIIGD-DINR-CONH$_2$, hereafter referred to as "FITC-Bak" was synthesized and purity determined to be >95% (Neo BioScience). The concentrated peptide stocks were prepared in DMSO and the concentration of the peptide was determined in water at pH 8.0 using the extinction coefficient for amide-linked FITC of $\lambda_{494}$=68,000 cm$^{-1}$M$^{-1}$.

General Procedure 1: Synthesis of Functionalized Sulfonamides (13-30)

Either 4-fluoro-3-nitrobenzenesulfonamide or 3-fluoro-4-nitrobenzenesulfonamide (1.0 eq.) was placed in a reaction flask and solubilized in DMF (0.1 M). Selected amines (1.1 eq.) and K$_2$CO$_3$ (2.0 eq.) were added to the reaction mixture. The reaction stirred at room temperature for 16 hrs. Reaction completion was monitored via TLC in a 92:7:1 DCM/MeOH/NH$_4$OH solvent system. Upon completion, the reaction was partitioned between Ethyl Acetate and Brine. The organic layer was washed five times with Brine to remove the DMF. The organic layer was then collected, dried with Na$_2$SO$_4$, filtered, concentrated down and azeotroped three times with CHCl$_3$ to produce the desired functionalized sulfonamides.

General Procedure 2: Sulfonamide Coupling of N-alkylated Indazole Carboxylic Acids An alkylated indazole (1.0 eq.) was added to a reaction flask, followed by the addition of anhydrous DMF (0.1 M). DMAP (0.5 eq.) and EDCI (1.2 eq.) were added to the reaction flask. The reaction stirred at room temperature for 10 minutes before the addition of the desired sulfonamide (1.1 eq.). The reaction was stirred at room temperature for 16 hr. Completion of the reaction was monitored via TLC. The reaction was partitioned between Brine and Ethyl Acetate. The organic layer was washed 5 times with brine, collected, dried with Na$_2$SO$_4$, filtered and concentrated down. The crude material was redistributed in DCM and dry loaded onto silica gel. Flash column chromatography was then performed to purify the desired product. The product fractions were collected, concentrated down and azeotroped with CHCl$_3$ to yield the purified product.

General Procedure 3: Methyl-Esterification of Carboxylic Acids

A carboxylic acid (1.0 eq.) was dissolved in MeOH (0.1 M) and SOCl$_2$ (3.0 eq.) was slowly added to the reaction. The reaction stirred at 65° C. for 16 hrs. Completion of the reaction was monitored via TLC with a gradient of 92:7:1 DCM/MeOH/Acetic acid. The reaction was concentrated down and then partitioned between sat. Na$_2$CO$_3$ and Ethyl Acetate. The organic layer was collected, dried with Na$_2$SO$_4$, filtered, concentrated down and azeotroped with CHCl$_3$ to yield the purified product.

General Procedure 4: N-Alkylation of the Heterocyclic Cores

A heterocyclic core (1.0 eq.) was added to a reaction flask, followed by the addition of DMF (0.1 M). A desired alkyl bromide (1.1 eq.) and K$_2$CO$_3$ (2.0 eq.) are then added to the reaction mixture. The reaction stirred for 16 hr at a given temperature. Completion of the reaction was monitored via TLC in 2:1 Hexanes/Ethyl Acetate. The reaction was partitioned between Brine and Ethyl Acetate. The organic layer was washed 5 times with Brine, collected, dried with Na$_2$SO$_4$, filtered and concentrated down. The crude material dry loaded onto silica gel and purified via flash column chromatography. The product fractions were collected, concentrated down and azeotroped with CHCl$_3$ to yield the purified product.

General Procedure 5: Saponification of Methyl and Ethyl Esters

An ester (1.0 eq.) was added to a reaction flask, followed by the addition of NaOH (3.0 eq.). A 3:1:1 mixture of THF/H$_2$O/MeOH (0.1 M) was added to the reaction flask. If the reaction did not consist of one phase then additional THF and MeOH were added. Once the reaction was one phase, it was stirred at room temperature for 16 hr. Completion of the reaction was monitored via TLC in 92:7:1 DCM/MeOH/Acetic Acid solvent system. The reaction mixture was partitioned between 1 M HCl and Ethyl Acetate. The organic layer was collected, dried with $Na_2SO_4$, filtered, concentrated down and azeotroped with $CHCl_3$ to yield the purified product.

Synthesis of methyl 1H-benzo[d]imidazole-2-carboxylate (2)

Follow General Procedure 3 with 1H-benzo[d]imidazole-2-carboxylic acid (3.08 mmols). Yield=380 mgs, 78% (white solid). $^1$H NMR (400 MHz, $d_6$-DMSO) δ=13.55 (s, 1H), 7.79 (d, J=7.6 Hz, 1H), 7.59 (d, J=8.0 Hz, 1H), 7.40 (t, J=7.8 Hz, 1H), 7.32 (t, J=7.8 Hz, 1H), 3.97 (s, 3H). $^{13}$C NMR (400 MHz, $d_6$-DMSO) δ=165.0, 146.9, 144.0, 129.1, 126.9, 126.5, 122.0, 57.8.

Synthesis of methyl 1-(3-(4-chloro-3,5-dimethylphenoxy)propyl)-1H-benzo[d]imidazole-2-carboxylate (4)

Follow General Procedure 4 with 2 (2.04 mmol) and 5-(3-bromopropoxy)-2-chloro-1,3-dimethylbenzene (3). Heat the reaction at 45° C. for 16 hr. Flash column chromatography was performed using a gradient of 1:1 Hexanes/Ethyl Acetate. Yield=655 mgs, 83% (orange oil). $^1$H NMR (400 MHz, $CDCl_3$) δ=7.90 (d, J=7.2 Hz, 1H), 7.47 (d, J=7.6 Hz, 1H), 7.36-7.34 (m, 2H), 6.58 (s, 2H), 4.85 (t, J=7.0 Hz, 4.00 (s, 3H), 3.91 (t, J=5.6, 2H), 2.35-2.33 (m, 8H). $^{13}$C NMR (400 MHz, $CDCl_3$) δ=158.7, 154.6, 140.0, 138.7, 135.5, 134.6, 124.8, 124.1, 122.2, 120.3, 112.8, 109.0, 63.0, 51.2, 40.8, 28.4, 19.3.

Synthesis of 1-(3-(4-chloro-3,5-dimethylphenoxy)propyl)-1H-benzo[d]imidazole-2-carboxylic acid (5)

Follow General Procedure 5 with 4 (1.29 mmol). Yield=438 mgs, 95% (white solid). $^1$H NMR (400 MHz, $d_6$-DMSO) δ=9.61 (s, 1H), 8.02 (m, 1H), 7.90 (m, 1H), 7.60 (m, 2H), 6.67 (s, 2H), 4.67 (t, J=6.6 Hz, 2H), 4.05 (t, J=5.6 Hz, 2H), 2.38 (t, J=5.8 Hz, 2H), 2.28 (s, 6H). $^{13}$C NMR (400 MHz, $CDCl_3$) δ=161.3, 147.1, 141.6, 137.2, 136.6, 131.1, 130.8, 130.3, 120.5, 119.8, 118.2, 70.1, 48.9, 33.4, 25.6.

Synthesis of 5-chloroindazole-3-carboxylic acid (7)

5-chloroisatin (6, 5.51 mmol) was added to a reaction flask, followed by the addition of $H_2O$ (0.1 M) and NaOH (6.06 mmol mmol). The reaction was heated to 45° C. and stirred for 30 minutes or until all the starting material was solubilized. The reaction mixture was then cooled to 0° C. $NaNO_2$ (5.51 mmol) was dissolved in $H_2O$ and slowly added to the reaction. The reaction stirred for 10 minutes and then $H_2SO_4$ (11.02 mmol) was added to the reaction. After 30 minutes of stirring, Sn(II)$Cl_2$ (13.22 mmol) was dissolved in concentrated HCl and slowly added to the reaction mixture. The reaction was stirred at 0° C. for 16 hr. The resulting precipitate was filtered from the reaction mixture and carried forwarded to the next reaction.

Synthesis of methyl 5-chloro-1H-indazole-3-carboxylate (8)

Crude 7 (5.09 mmol) was dissolved in MeOH (0.1 M) and $SOCl_2$ (15.26 mmol) was slowly added to the reaction. The reaction stirred at 65° C. for 16 hrs. Completion of the reaction was monitored via TLC in 1:1 Hexanes/Ethyl Acetate. The reaction was concentrated down and then partitioned between Brine and ethyl acetate. The organic layer was collected, dried with $Na_2SO_4$, filtered and concentrated down. The crude material was redistributed in DCM and dry loaded onto silica gel. Flash column chromatography was then performed to purify the desired product using a gradient of 1:1 Hexanes/Ethyl Acetate. The product fractions were collected, concentrated down and azeotroped with $CHCl_3$ to yield the purified product. Yield=475 mgs, 53% (yellow solid). $^1$H NMR (400 MHz, $d_6$-DMSO) δ=8.06 (s, 1H), 7.73 (d, J=9.6 Hz, 1H), 7.49 (d, J=8.8 Hz, 1H), 3.94 (s, 3H). $^{13}$C NMR (400 MHz, $d_6$-DMSO) δ=167.5, 144.6, 132.8, 132.3, 128.1, 125.1, 118.2, 57.0.

Synthesis of methyl 5-chloro-2-(3-(4-chloro-3,5-dimethylphenoxy)propyl)-2H-indazole-3-carboxylate (9a)

Follow General Procedure 4 with 8 (2.27 mmol) and 5-(3-bromopropoxy)-2-chloro-1,3-dimethylbenzene (3). Heat the reaction at 45° C. for 16 hr. Flash column chromatography was performed using a gradient of 4:1 Hexanes/Ethyl Acetate. Yield=443 mgs, 48% (yellow oil). $^1$H NMR (400 MHz, $CDCl_3$) δ=7.95 (s, 1H), 7.66 (d, J=9.2 Hz, 1H), 7.25 (d, J=8.4 Hz, 1H), 6.51 (s, 2H), 5.06 (t, J=7.2 Hz, 2H), 3.95 (m, 5H), 2.45-2.40 (m, 2H), 2.28 (s, 6H). $^{13}$C NMR (400 MHz, $CDCl_3$) δ=160.2, 156.4, 145.7, 139.9, 137.0, 131.1, 127.8, 124.0, 120.3, 119.7, 115.8, 114.4, 65.0, 52.1, 51.0, 30.3, 20.9.

Synthesis of 5-chloro-2-(2-(4-chloro-3,5-dimethylphenoxy)ethyl)-2H-indazole-3-carboxylic acid (9b)

Follow General Procedure 4 with 8 (0.76 mmol) and 5-(4-(bromomethyl)phenoxy)-2-chloro-1,3-dimethylbenzene. The reaction stirred at room temperature for 16 hr. Flash column chromatography was performed using a gradient of 4:1 Hexanes/Ethyl Acetate. Yield=215 mgs, 45% (yellow oil). $^1$H NMR (400 MHz, $CDCl_3$) δ=7.96 (s, 1H), 7.70 (d, J=8.4 Hz, 1H), 7.27 (d, J=8.8 Hz, 1H), 6.55 (s, 2H), 5.26 (t, J=5.8 Hz, 2H), 4.43 (t, J=6.0 Hz, 2H), 4.03 (s, 3H), 2.26 (s, 6H). $^{13}$C NMR (400 MHz, $CDCl_3$) δ=160.4, 155.9, 145.9, 138.7, 128.0, 120.3, 119.8, 114.6, 66.7, 52.6, 52.2, 20.9.

Synthesis of methyl 5-chloro-2-(4-(4-chloro-3,5-dimethylphenoxy)benzyl)-2H-indazole-3-carboxylate (9c)

Follow General Procedure 4 with 8 (2.37 mmol) and 5-(2-bromoethoxy)-2-chloro-1,3-dimethylbenzene. The reaction stirred at room temperature for 16 hr. Flash column chromatography was performed using a gradient of 4:1 Hexanes/Ethyl Acetate. Yield=411 mgs, 44% (yellow oil). $^1$H NMR (400 MHz, $CDCl_3$) δ=8.00 (s, 1H), 7.74 (d, J=8.8 Hz, 1H), 7.36 (d, J=8.8 Hz, 2H), 7.30-7.26 (m, 1H), 6.90 (d, J=8.8 Hz, 2H), 6.70 (s, 2H), 6.05 (s, 2H), 4.03 (s, 3H), 2.31 (s, 6H). $^{13}$C NMR (400 MHz, $CDCl_3$) δ=160.3, 157.3, 154.4, 145.9, 137.7, 131.2, 130.7, 129.7, 127.9, 124.0, 120.4, 119.9, 119.0, 118.5, 56.1, 52.2, 20.8.

Synthesis of 5-chloro-2-(3-(4-chloro-3,5-dimethylphenoxy)propyl)-2H-indazole-3-carboxylic acid (10)

Follow General Procedure 5 with 9a (1.35 mmol). Yield=504 mgs, 95% (white solid). $^1$H NMR (400 MHz, d$_6$-DMSO) δ=7.99 (s, 1H), 7.82 (d, J=9.6 Hz, 1H), 7.37 (d, J=7.2 Hz, 1H), 6.65 (s, 2H), 5.02 (t, J=6.8 Hz, 2H), 3.98 (t, J=5.8 Hz, 2H), 2.35 (t, J=6.0 Hz, 2H), 2.25 (s, 6H). $^{13}$C NMR (400 MHz, d$_6$-DMSO) δ=166.6, 161.6, 150.1, 141.6, 133.1, 132.7, 131.8, 130.2, 128.6, 126.0, 124.8, 119.8, 70.2, 55.0, 50.4, 35.1, 25.6, 13.6.

Synthesis of 5-chloro-2-(2-(4-chloro-3,5-dimethylphenoxy)ethyl)-2H-indazole-3-carboxylic acid (11)

Follow General Procedure 5 with 9c (0.56 mmol). Yield=205 mgs, 93% (white solid). $^1$H NMR (400 MHz, d$_6$-DMSO) δ=7.99 (s, 1H), 7.84 (d, J=9.2 Hz, 1H), 7.38 (d, J=9.2 Hz, 1H), 6.73 (s, 2H), 5.25 (t, J=5.2 Hz, 2H), 4.50 (t, J=5.4 Hz, 2H), 2.24 (s, 6H). $^{13}$C NMR (400 MHz, d$_6$-DMSO) δ=165.7, 161.1, 150.3, 141.7, 134.4, 132.4, 130.5, 128.6, 125.3, 119.9, 71.8, 57.1, 48.5, 46.3, 25.5.

Synthesis of 5-chloro-2-(4-(4-chloro-3,5-dimethylphenoxy)benzyl)-2H-indazole-3-carboxylic acid (12)

Follow General Procedure 5 with 9b (0.40 mmol). Yield=164 mgs, 92% (yellow solid). $^1$H NMR (400 MHz, d$_6$-DMSO) δ=7.96 (s, 1H), 7.82 (d, J=8.4 Hz, 1H), 7.35 (d, J=7.2 Hz, 1H), 7.26 (d, J=8.8 Hz, 2H), 6.92 (d, J=8.8 Hz, 2H), 6.83 (s, 2H), 6.02 (s, 2H), 2.24 (s, 6H). $^{13}$C NMR (400 MHz, d$_6$-DMSO) δ=165.7, 161.6, 159.4, 150.5, 142.6, 136.7, 134.8, 134.7, 133.5, 132.5, 129.5, 128.7, 125.4, 124.2, 123.5, 60.3, 25.5.

Synthesis of 4-chlorobenzenesulfonamide (13)

4-chlorobenzenesufonyl chloride (1.0 mmol) was dissolved in dioxane (0.1 M) and cooled to 0° C. NH$_4$OH (5.0 mmol) was added dropwise to the reaction. The reaction stirred at 0° C. for 30 minutes. Completion of the reaction was monitored via TLC with a 1:1 gradient of Hexanes/Ethyl Acetate. The reaction was partitioned between Ethyl Acetate and Brine. The organic layer was collected, dried with Na$_2$SO$_4$, filtered, concentrated down and azeotroped with CHCl$_3$ to produce the desired product. Yield=169 mgs, 88% (white solid). $^1$H and $^{13}$C spectra were consistent with the literature.

Synthesis of 4-morpholino-3-nitrobenzenesulfonamide (14)

Follow General Procedure 1 using 4-fluoro-3-nitrobenzenesulfonamide (0.91 mmol) and morpholine. Yield=201 mgs, 77% (yellow solid). $^1$H (400 MHz, DMSO) δ=8.22 (s, 1H), 7.92 (d, J=7.4 Hz, 1H), 7.46 (d, J=8 Hz, 2H), 3.72 (t, J=6.8 Hz, 4H), 3.14 (t, J=6.8 Hz, 4H), 2.00 (s, 1H). $^{13}$C NMR (400 MHz, DMSO) δ=152.3, 144.1, 140.2, 136.1, 129.5, 126.2, 71.0, 55.8, 51.0.

Synthesis of 4-((2-morpholinoethyl)amino)-3-nitrobenzenesulfonamide (15)

Follow General Procedure 1 using 4-fluoro-3-nitrobenzenesulfonamide (0.91 mmol) and 2-morpholinoethan-1-amine. Yield=195 mgs, 65% (yellow solid). $^1$H (400 MHz, DMSO) δ=8.78 (t, J=7 Hz, 1H), 8.48 (s, 1H), 7.85 (d, J=7.4 Hz, 1H), 7.35 (s, 2H), 7.23 (d, J=7.4 Hz, 1H), 3.61 (m, 4H), 3.50 (q, J=6.8 Hz, 2H), 2.64 (t, J=6.8 Hz, 2H), 2.46 (s, 4H). $^{13}$C NMR (400 MHz, DMSO) δ=151.6, 138.0, 135.3, 134.6, 129.8, 121.1, 71.5, 60.5, 58.0, 45.3.

Synthesis of 4-((furan-2-ylmethyl)amino)-3-nitrobenzenesulfonamide (16)

Follow General Procedure 1 using 4-fluoro-3-nitrobenzenesulfonamide (0.91 mmol) and furan-2-ylmethanamine. Yield=197 mgs, 73% (yellow solid). $^1$H (400 MHz, DMSO) δ=8.89 (t, J=7.4 Hz, 1H), 8.49 (s, 1H), 7.83 (d, J=7 Hz, 1H), 7.62 (s, 1H), 7.31-7.33 (m, 2H), 6.41 (s, 2H), 4.71 (d, J=6.8 Hz, 2H). $^{13}$C NMR (400 MHz, DMSO) δ=156.1, 151.3, 147.9, 137.8, 135.8, 129.8, 121.0, 115.7, 113.1, 45.1.

Synthesis of 4-((2-(furan-2-yl)ethyl)amino)-3-nitrobenzenesulfonamide (17)

Follow General Procedure 1 using 4-fluoro-3-nitrobenzenesulfonamide (0.91 mmol) and 2-(furan-2-yl)ethan-1-amine. Yield=209 mgs, 74% (yellow solid). $^1$H NMR (400 MHz, d$_6$-DMSO) δ=8.58 (t, J=5.4 Hz, 1H), 8.50 (d, J=2.4 Hz, 2H), 7.86 (d, J=9.6 Hz, 1H), 7.59 (s, 1H), 7.38 (s, 2H), 7.25 (d, J=9.2 Hz, 1H), 6.41 (s, 1H), 6.28 (d, J=2.8 Hz, 1H), 3.72 (q, J=6.4 Hz, 2H), 3.03 (t, J=7.0 Hz, 2H). $^{13}$C NMR (400 MHz, d$_6$-DMSO) δ=157.5, 151.5, 147.2, 138.0, 135.5, 134.7, 129.9, 120.6, 115.8, 111.9, 46.5, 32.1.

Synthesis of 4-(((1-methyl-H-pyrazol-3-yl)methyl)amino)-3-nitrobenzenesulfonamide (18)

Follow General Procedure 1 using 4-fluoro-3-nitrobenzenesulfonamide (0.91 mmol) and (1-methyl-1H-pyrazol-3-yl)methanamine. Yield=178 mgs, 63% (yellow solid). H NMR (400 MHz, d$_6$-DMSO) δ=8.83 (t, J=5.6 Hz, 1H), 8.51 (s, 1H), 7.84 (d, J=8.4 Hz, 1H), 7.71 (s, 1H), 7.48 (s, 1H), 7.36 (s, 2H), 7.28 (d, J=9.6 Hz, 1H), 4.53 (d, J=6.0 Hz, 2H), 3.80 (s, 3H). $^{13}$C NMR (400 MHz, d$_6$-DMSO) δ=149.6, 141.5, 136.2, 133.7, 133.1, 128.2, 120.9, 119.3, 43.7, 40.6.

Synthesis of 3-nitro-4-((pyridin-3-ylmethyl)amino)benzenesulfonamide (19)

Follow General Procedure 1 using 4-fluoro-3-nitrobenzenesulfonamide (0.91 mmol) and pyridin-3-ylmethanamine. Yield=193 mgs, 69% (yellow solid). $^1$H (400 MHz, DMSO) δ=9.11 (t, J=7.8 Hz, 1H), 8.64 (s, 1H), 8.47-8.50 (m, 2H), 7.77 (m, 2H), 7.35-7.38 (m, 1H), 7.31 (s, 2H), 7.11 (d, J=8.4 Hz, 1H), 4.75 (d, J=8.4 Hz, 2H). $^{13}$C NMR (400 MHz, d$_6$-DMSO) δ=149.0, 148.8, 146.5, 135.3, 134.1, 133.2, 131.0, 130.6, 125.2, 124.1, 116.1, 43.8.

Synthesis of 3-nitro-4-((2-(pyridin-3-yl)ethyl)amino)benzenesulfonamide (20)

Follow General Procedure 1 using 4-fluoro-3-nitrobenzenesulfonamide (0.91 mmol) and 2-(pyridin-3-yl)ethan-1-amine. Yield=187 mgs, 64% (yellow solid). $^1$H NMR (400 MHz, d$_6$-DMSO) δ=8.56 (d, J=7.2 Hz, 2H), 8.50 (s, 1H), 8.47 (d, J=4.0 Hz, 1H), 7.87 (d, J=8.8 Hz, 1H), 7.76 (d, J=7.6 Hz, 1H), 7.37 (d, J=12.0 Hz, 4H), 3.74 (q, J=6.4 Hz, 2H), 3.00 (t, J=7.2 Hz, 2H). $^{13}$C NMR (400 MHz, d$_6$-DMSO) δ=150.4, 148.1, 146.7, 136.9, 134.6, 133.3, 130.7, 129.9, 125.2, 123.9, 116.0, 43.9, 31.8.

Synthesis of 3-nitro-4-((pyridin-4-ylmethyl)amino)benzenesulfonamide (21)

Follow General Procedure 1 using 4-fluoro-3-nitrobenzenesulfonamide (0.91 mmol) and pyridin-4-ylmethanamine.

Yield=162 mgs, 58% (yellow solid). $^1$H NMR (400 MHz, d$_6$-DMSO) δ=9.13 (t, J=6.2 Hz, 1H), 8.52 (d, J=2.4 Hz, 3H), 7.75 (d, J=7.6 Hz, 1H), 7.35-7.33 (m, 4H), 6.97 (d, J=8.4 Hz, 1H), 4.77 (d, J=6.0 Hz, 2H). $^{13}$C NMR (400 MHz, d$_6$-DMSO) δ=155.0, 154.9, 152.2, 151.7, 148.2, 135.8, 130.0, 129.9, 127.1, 127.0, 120.8, 49.9.

Synthesis of 3-nitro-4-((2-(pyridin-4-yl)ethyl)amino)benzenesulfonamide (22)

Follow General Procedure 1 using 4-fluoro-3-nitrobenzenesulfonamide (0.91 mmol) and 2-(pyridin-4-yl)ethan-1-amine. Yield=161 mgs, 55% (yellow solid). $^1$H NMR (400 MHz, d$_6$-DMSO) δ=8.54 (bs, 2H), 8.26 (d, J=8.4 Hz, 2H), 7.67 (s, 2H), 7.51 (s, 1H), 7.37 (bs, 2H), 7.08 (d, J=8.8 Hz, 1H), 3.69 (t, J=5.8 Hz, 2H), 3.03 (t, J=6.6 Hz, 2H). $^{13}$C NMR (400 MHz, d$_6$-DMSO) δ=155.7, 154.8, 153.0, 149.6, 137.5, 133.1, 129.5, 116.9, 116.7, 48.0, 38.5.

Synthesis of 3-nitro-4-((2-(pyridin-4-yl)ethyl)amino)benzenesulfonamide (23)

Follow General Procedure 1 using 3-fluoro-4-nitrobenzenesulfonamide (0.91 mmol) and morpholine. Yield=196 mgs, 75% (yellow solid). $^1$H NMR (400 MHz, DMSO) δ=8.02 (d, J=8.8 Hz, 1H), 7.68 (s, 1H), 7.62 (s, 2H), 7.51 (d, J=8.8 Hz), 3.72 (t, J=4.4 Hz, 4H), 3.05 (t, J=4.4 Hz, 4H). $^{13}$C NMR (400 MHz, d$_6$-DMSO) δ=148.7, 145.5, 144.0, 127.1, 118.9, 118.6, 66.4, 51.5.

Synthesis of 3-((furan-2-ylmethyl)amino)-4-nitrobenzenesulfonamide (24)

Follow General Procedure 1 using 3-fluoro-4-nitrobenzenesulfonamide (0.91 mmol) and furan-2-ylmethanamine. Yield=189 mgs, 70% (yellow solid). $^1$H NMR (400 MHz, DMSO) δ=8.64 (t, J=5.8 Hz, 1H), 8.26 (d, J=8.4 Hz, 1H), 7.64 (s, 3H), 7.54 (s, 1H), 7.09 (d, J=8.8 Hz, 1H), 6.41 (d, J=16.4 Hz, 2H), 4.66 (d, J=6.4 Hz, 2H). $^{13}$C NMR (400 MHz, d$_6$-DMSO) δ=151.4, 150.7, 144.7, 143.2, 133.0, 128.2, 112.4, 112.3, 111.1, 108.3.

Synthesis of 3-((2-(furan-2-yl)ethyl)amino)-4-nitrobenzenesulfonamide (25)

Follow General Procedure 1 using 3-fluoro-4-nitrobenzenesulfonamide (0.91 mmol) and 2-(furan-2-yl)ethan-1-amine. Yield=221 mgs, 78% (yellow solid). $^1$H NMR (400 MHz, d$_6$-DMSO) δ=8.30 (t, J=5.4 Hz, 1H), 8.26 (d, J=8.4 Hz, 1H), 7.65 (s, 2H), 7.59 (s, 1H), 7.47 (s, 1H), 7.08 (d, 9.6 Hz, 1H), 6.41 (t, J=2.4 Hz, 1H), 6.28 (d, J=2.8 Hz, 1H), 3.68 (q, J=6.4 Hz, 2H), 3.05 (t, J=7.0 Hz, 2H). $^{13}$C NMR (400 MHz, d$_6$-DMSO) δ=157.5, 155.7, 149.6, 147.2, 137.4, 133.0, 116.8, 116.7, 115.7, 111.8, 46.4, 32.0.

Synthesis of 3-(((1-methyl-H-pyrazol-3-yl)methyl)amino)-4-nitrobenzenesulfonamide (26)

Follow General Procedure 1 using 3-fluoro-4-nitrobenzenesulfonamide (0.91 mmol) and (1-methyl-1H-pyrazol-3-yl)methanamine. Yield=192 mgs, 68% (yellow solid). $^1$H NMR (400 MHz, d$_6$-DMSO) δ=8.54 (t, J=5.4 Hz, 1H), 8.27 (d, J=9.2 Hz, 1H), 7.71 (s, 1H), 7.68 (s, 2H), 7.52 (s, 1H), 7.47 (s, 1H), 7.07 (d, J=9.2 Hz, 1H), 4.48 (d, J=5.6 Hz, 2H), 3.81 (s, 3H). $^{13}$C NMR (400 MHz, d$_6$-DMSO) δ=153.8, 147.9, 141.5, 135.8, 133.2, 120.9, 115.5, 114.9, 43.7, 40.6.

Synthesis of 4-nitro-3-((pyridin-3-ylmethyl)amino)benzenesulfonamide (27)

Follow General Procedure 1 using 3-fluoro-4-nitrobenzenesulfonamide (0.91 mmol) and pyridin-3-ylmethanamine. Yield=168 mgs, 60% (yellow solid). $^1$H NMR (400 MHz, DMSO) δ=8.84 (t, J=6.2 Hz, 1H), 8.63 (s, 1H), 8.49 (d, J=3.6 Hz, 1H), 8.28 (d, J=8.8 Hz, 1H), 7.79 (d, J=7.6 Hz, 1H), 7.61 (s, 2H), 7.40-7.37 (m, 1H), 7.33 (s, 1H), 7.07 (d, J=8.4 Hz, 1H), 4.70 (d, J=6.4 Hz, 2H). $^{13}$C NMR (400 MHz, d$_6$-DMSO) δ=150.7, 149.0, 144.7, 135.3, 134.1, 133.1, 128.3, 124.2, 112.21, 112.16, 44.0.

Synthesis of 4-nitro-3-((2-(pyridin-3-yl)ethyl)amino)benzenesulfonamide (28)

Follow General Procedure 1 using 3-fluoro-4-nitrobenzenesulfonamide (0.91 mmol) and 2-(pyridin-3-yl)ethan-1-amine. Yield=187 mgs, 64% (yellow solid). $^1$H NMR (400 MHz, d$_6$-DMSO) δ=8.56 (s, 1H), 8.48 (s, 1H), 8.27 (d, J=8.4 Hz, 2H), 7.77 (d, J=8.0 Hz, 1H), 7.67 (s, 2H), 7.51 (s, 1H), 7.40 (t, J=6.2 Hz, 1H), 7.08 (d, J=9.6 Hz, 1H), 3.68 (q, J=6.8 Hz, 2H), 3.03 (t, J=7.0 Hz, 2H). $^{13}$C NMR (400 MHz, d$_6$-DMSO) δ=150.9, 150.2, 148.1, 144.8, 137.0, 134.7, 132.7, 128.3, 124.1, 112.2, 111.9, 44.0, 31.6.

Synthesis of 4-nitro-3-((pyridin-4-ylmethyl)amino)benzenesulfonamide (29)

Follow General Procedure 1 using 3-fluoro-4-nitrobenzenesulfonamide (0.91 mmol) and pyridin-4-ylmethanamine. Yield=154 mgs, 55% (yellow solid). $^1$H NMR (400 MHz, d$_6$-DMSO) δ=8.89 (t, J=5.8 Hz, 1H), 8.55 (d, J=5.6 Hz, 2H), 8.31 (d, J=9.2 Hz, 1H), 7.60 (s, 1H), 7.39 (d, J=4.4 Hz, 2H), 7.22 (s, 1H), 7.09 (d, J=9.6 Hz, 1H), 4.73 (d, J=6.4 Hz, 2H). $^{13}$C NMR (400 MHz, d$_6$-DMSO) δ=155.5, 155.0, 152.5, 149.5, 137.9, 133.1, 127.1, 125.7, 117, 116.9, 50.1.

Synthesis of 4-nitro-3-((2-(pyridin-4-yl)ethyl)amino)benzenesulfonamide (30)

Follow General Procedure 1 using 3-fluoro-4-nitrobenzenesulfonamide (0.91 mmol) and 2-(pyridin-4-yl)ethan-1-amine. Yield=170 mgs, 58% (yellow solid). $^1$H NMR (400 MHz, d$_6$-DMSO) δ=8.57-8.50 (m, 4H), 7.88 (d, J=8.8 Hz, 1H), 7.39-7.36 (m, 5H), 3.78-3.73 (m, 2H), 3.00 (t, J=7.4 Hz, 2H). $^{13}$C NMR (400 MHz, d$_6$-DMSO) δ=154.8, 152.9, 151.4, 138.1, 135.5, 134.7, 129.9, 129.6, 120.8, 47.9, 38.6.

Synthesis of 6-chloro-2-(4-(4-chloro-3,5-dimethylphenoxy)benzyl)-N-((4-chlorophenyl)sulfonyl)-2H-indazole-3-carboxamide (31)

Follow General Procedure 2 with 12 (0.23 mmol) and 13. The product was purified via flash column chromatography in a gradient of 92:7:1 DCM/MeOH/H$_2$O. Yield=77 mgs, 55% (yellow solid). $^1$H NMR (400 MHz, DMSO) δ=8.21 (s, 1H), 7.89 (d, J=8.4 Hz, 2H), 7.69 (d, J=9.6 Hz, 1H), 7.51 (d, J=8.4 Hz, 2H), 7.27 (dd, J=9.6, 1.6, 1H), 7.19 (d, J=8.8 Hz, 2H), 6.86-6.82 (m, 4H), 6.03 (s, 2H), 2.29 (s, 6H); $^{13}$C NMR (400 MHz, DMSO) δ=156.7, 154.6, 145.5, 137.9, 132.6, 130.3, 129.6, 128.7, 128.5, 127.1, 122.9, 119.8, 119.5, 118.4, 55.7, 20.8.

Synthesis of 6-chloro-2-(4-(4-chloro-3,5-dimethylphenoxy)benzyl)-N-((4-morpholino-3-nitrophenyl)sulfonyl)-2H-indazole-3-carboxamide (32)

Follow General Procedure 2 with 12 (0.23 mmol) and 14. The product was purified via flash column chromatography in a gradient of 92:7:1 DCM/MeOH/H$_2$O. Yield=68 mgs, 42% (yellow solid). $^1$H NMR (400 MHz, DMSO) δ=8.27 (d, J=8.0, 2H), 8.00 (d, J=8.8, 1H), 7.67 (d, J=9.2, 1H), 7.31 (d, J=8.8, 1H), 7.26-7.23 (m, 3H), 6.85-6.84 (m, 4H), 6.08 (s, 2H), 3.66 (s, 4H), 3.03 (s, 4H), 2.29 (s, 6H). $^{13}$C NMR (400 MHz, DMSO) δ=156.5, 154.8, 146.8, 145.5, 139.5, 139.8, 137.8, 132.9, 130.4, 128.6, 127.5, 126.9, 125.8, 123.0, 122.4, 120.4, 119.7, 119.3, 118.6, 66.3, 51.3, 20.7.

Synthesis of 6-chloro-2-(4-(4-chloro-3,5-dimethylphenoxy)benzyl)-N-((4-((morpholinomethyl)amino)-3-nitrophenyl)sulfonyl)-2H-indazole-3-carboxamide (33)

Follow General Procedure 2 with 12 (0.23 mmol) and 15. The product was purified via flash column chromatography in a gradient of 92:7:1 DCM/MeOH/H$_2$O. Yield=75 mgs, 44% (yellow solid). $^1$H NMR (400 MHz, DMSO) δ=8.64 (s, br, 1H), 8.58 (s, 1H), 8.29 (s, 1H), 8.97 (d, J=8.0, 1H), 7.64 (d, J=9.6, 1H), 7.27-7.22 (m, 3H), 7.07 (d, J=7.6, 1H), 6.85-6.83 (m, 4H), 6.11 (s, 2H), 3.58 (s, br, 4H), 3.42 (s, br, 2H), 2.60 (s, br, 2H), 2.42 (s, br, 4H), 2.28 (s, 6H). $^{13}$C NMR (400 MHz, DMSO) δ=163.7, 156.4, 154.8, 146.2, 145.5, 137.8, 135.3, 133.1, 132.7, 132.0, 130.4, 128.6, 127.3, 126.9, 126.1, 123.0, 122.6, 119.6, 119.2, 118.6, 114.6, 66.5, 55.6, 54.6, 53.0, 20.7.

Synthesis of 6-chloro-2-(4-(4-chloro-3,5-dimethylphenoxy)benzyl)-N-((4-((furan-2-ylmethyl)amino)-3-nitrophenyl)sulfonyl)-2H-indazole-3-carboxamide (34)

Follow General Procedure 2 with 12 (0.23 mmol) and 16. The product was purified via flash column chromatography in a gradient of 92:7:1 DCM/MeOH/H$_2$O. Yield=91 mgs, 56% (yellow solid). $^1$H NMR (400 MHz, DMSO) δ=8.73 (m, 1H), 8.58 (s, 1H), 8.25 (s, 1H), 7.94 (d, J=8.4, 1H), 7.66 (d, J=8.4, 1H), 7.58 (s, 1H), 7.26-7.24 (m, 3H), 7.19 (d, J=9.6, 1H), 6.84-6.83 (4H), 6.38 (s, 2H), 6.08 (s, 2H), 4.65 (d, J=6.4, 2H), 2.28 (s, 6H). $^{13}$C NMR (400 MHz, DMSO) δ=163.3, 156.5, 154.8, 151.5, 146.0, 145.5, 143.1, 137.8, 135.0, 133.0, 132.5, 130.3, 128.6, 127.5, 127.0, 126.2, 123.0, 122.4, 119.7, 119.3, 118.6, 118.2, 114.7, 110.9, 108.2, 54.6, 20.7.

Synthesis of 6-chloro-2-(4-(4-chloro-3,5-dimethylphenoxy)benzyl)-N-((4-((2-(furan-2-yl)ethyl)amino)-3-nitrophenyl)sulfonyl)-2H-indazole-3-carboxamide (35)

Follow General Procedure 2 with 12 (0.23 mmol) and 17. The product was purified via flash column chromatography in a gradient of 92:7:1 DCM/MeOH/H$_2$O. Yield=90 mgs, 54% (yellow solid). H NMR (400 MHz, d$_6$-DMSO) δ=8.64 (s, 1H), 8.61 (br, 1H), 8.03 (s, 1H), 7.98 (d, J=9.2, 1H), 7.79 (d, J=8.4, 1H), 7.56 (s, 1H), 7.36 (d, J=9.6, 1H), 7.21 (d, J=9.2 Hz, 1H), 7.15 (d, J=8.4 Hz, 2H), 6.81 (d, J=8.0 Hz, 5H), 6.37 (s, 1H), 6.24 (d, J=3.2 Hz, 1H), 5.93 (s, 2H), 3.68 (q, J=6.4 Hz, 2H), 2.99 (t, J=7.2 Hz, 2H), 2.29 (s, 6H). $^{13}$C NMR (400 MHz, DMSO) δ=161.2, 156.6, 154.7, 152.7, 146.9, 145.5, 142.4, 137.8, 135.0, 133.5, 132.4, 130.2, 127.4, 127.2, 122.7, 121.3, 120.1, 119.2, 118.6, 114.8, 112.0, 111.0, 107.1, 55.0, 41.7, 27.3, 20.7.

Synthesis of 6-chloro-2-(4-(4-chloro-3,5-dimethylphenoxy)benzyl)-N-((4-(((1-methyl-1H-pyrazol-3-yl)methyl)amino)-3-nitrophenyl)sulfonyl)-2H-indazole-3-carboxamide (36)

Follow General Procedure 2 with 12 (0.23 mmol) and 18. The product was purified via flash column chromatography in a gradient of 92:7:1 DCM/MeOH/NH$_4$OH. Yield=73 mgs, 44% (yellow solid). H NMR (400 MHz, d$_6$-DMSO) δ=8.69 (t, J=5.6 Hz, 1H), 8.61 (s, 1H), 8.21 (s, 1H), 7.97 (d, J=9.6 Hz, 1H), 7.71 (s, 1H), 7.69 (s, 1H), 7.45 (s, 1H), 7.31 (s, 2H), 7.24 (d, J=8.4 Hz, 2H), 7.18 (t, J=4.0 Hz, 2H), 7.05 (s, 1H), 6.84 (d, J=7.2 Hz, 4H), 6.06 (s, 2H), 4.46 (d, J=5.6 Hz, 2H), 3.78 (s, 3H), 2.29 (s, 6H). $^{13}$C NMR (400 MHz, d$_6$-DMSO) δ=156.5, 154.8, 146.2, 145.5, 138.4, 137.8, 135.1, 132.8, 130.3, 130.0, 128.6, 127.7, 127.1, 126.5, 122.9, 122.1, 119.8, 119.3, 118.6, 117.8, 114.8, 54.7, 46.2, 41.8, 40.6, 37.4, 20.7.

Synthesis of 6-chloro-2-(4-(4-chloro-3,5-dimethylphenoxy)benzyl)-N-((3-nitro-4-((pyridin-3-ylmethyl)amino)phenyl)sulfonyl)-2H-indazole-3-carboxamide (37)

Follow General Procedure 2 with 12 (0.23 mmol) and 19. The product was purified via flash column chromatography in a gradient of 92:7:1 DCM/MeOH/H$_2$O. Yield=65 mgs, 39% (yellow solid). $^1$H NMR (400 MHz, DMSO) δ=8.94 (t, J=6.2, 1H), 8.64 (s, br, 1H), 8.59 (s, 1H), 8.45 (s, br, 1H), 8.23 (s, 1H), 7.89 (d, J=8.4, 1H), 7.78 (d, J=8.0, 1H), 7.64 (d, J=9.6, 1H), 7.34 (m, 1H), 7.26-7.22 (m, 3H), 7.00 (d, J=9.6, 1H), 6.85-6.83 (m, 4H), 6.09 (S, 2H), 4.69 (d, J 6.4, 2H), 2.28 (s, 6H). $^{13}$C NMR (400 MHz, d$_6$-DMSO) δ=184.9, 163.7, 156.4, 154.8, 148.8, 148.5, 145.9, 145.5, 137.8, 135.5, 135.1, 133.1, 133.0, 131.9, 130.4, 128.6, 127.3, 126.9, 126.1, 124.0, 123.0, 122.6, 119.6, 119.3, 118.6, 114.5, 43.8, 20.7.

Synthesis of 6-chloro-2-(4-(4-chloro-3,5-dimethylphenoxy)benzyl)-N-((3-nitro-4-((2-(pyridin-3-yl)ethyl)amino)phenyl)sulfonyl)-2H-indazole-3-carboxamide (38)

Follow General Procedure 2 with 12 (0.23 mmol) and 20. The product was purified via flash column chromatography in a gradient of 84:14:2 DCM/MeOH/NH$_4$OH. Yield=59 mgs, 35% (yellow solid). $^1$H NMR (400 MHz, d$_6$-DMSO) δ=8.63 (s, 1H), 8.60 (s, 1H), 8.55 (d, J=4.0 Hz, 1H), 8.44 (t, J=5.8 Hz, 1H), 8.29 (s, 1H), 7.99 (d, J=8.4 Hz, 1H), 7.93 (d, J=7.6 Hz, 1H), 7.67 (d, J=8.4 Hz, 1H), 7.52 (t, J=6.2 Hz, 1H), 7.37 (1H), 7.29-7.23 (m, 4H), 7.12 (s, 1H), 6.86 (d, J=8.8 Hz, 2H), 6.82 (s, 2H), 6.11 (s, 2H), 3.69 (q, J=6.4 Hz, 2H), 3.01 (t, J=7.4 Hz, 2H), 2.27 (s, 6H). $^{13}$C NMR (400 MHz, d$_6$-DMSO) δ=168.1, 161.2, 159.6, 153.0, 150.9, 150.8, 150.2, 144.2, 142.5, 140.7, 140.1, 137.8, 137.2, 136.5, 135.1, 132.1, 131.7, 131.1, 129.5, 127.7, 127.2, 124.4, 123.9, 123.4, 119.2, 59.3, 48.4, 36.5, 25.5.

Synthesis of 6-chloro-2-(4-(4-chloro-3,5-dimethylphenoxy)benzyl)-N-((3-nitro-4-((pyridin-4-ylmethyl)amino)phenyl)sulfonyl)-2H-indazole-3-carboxamide (39)

Follow General Procedure 2 with 12 (0.23 mmol) and 21. The product was purified via flash column chromatography in a gradient of 84:14:2 DCM/MeOH/NH$_4$OH. Yield=61 mgs, 37% (yellow solid). $^1$H NMR (400 MHz, d$_6$-DMSO) δ=9.06 (bs, 1H), 8.70 (bs, 1H), 8.67 (d, J=18.0 Hz, 2H), 8.22 (s, 1H), 7.89 (d, J=9.2 Hz, 1H), 7.74 (bs, 2H), 7.68 (d, J=8.8 Hz, 1H), 7.26 (d, J=8.8 Hz, 3H), 6.86 (d, J=3.2 Hz, 5H), 6.08 (s, 2H), 4.89 (d, J=4.8 Hz, 2H), 2.30 (s, 6H). $^{13}$C NMR (400 MHz, d$_6$-DMSO) δ=163.0, 156.5, 155.9, 154.8, 145.9, 145.5, 144.9, 137.8, 135.1, 132.9, 132.5, 131.1, 130.9, 130.3, 128.6, 127.6, 127.0, 126.5, 124.3, 122.9, 122.2, 119.8, 119.3, 118.6, 114.6, 71.5, 45.6, 20.8.

Synthesis of 6-chloro-2-(4-(4-chloro-3,5-dimethylphenoxy)benzyl)-N-((3-nitro-4-((2-(pyridin-4-yl)ethyl)amino)phenyl)sulfonyl)-2H-indazole-3-carboxamide (40)

Follow General Procedure 2 with 12 (0.23 mmol) and 22. The product was purified via flash column chromatography in a gradient of 84:14:2 DCM/MeOH/NH$_4$OH. Yield=66 mgs, 39% (yellow solid). $^1$H NMR (400 MHz, d$_6$-DMSO) δ=8.66 (d, J=4.8 Hz, 2H), 8.30 (s, 1H), 8.24 (t, J=6.0 Hz, 1H), 8.12 (d, J=8.4 Hz, 1H), 7.73 (d, J=5.6 Hz, 2H), 7.68 (d, J=9.6 Hz, 2H), 7.31-7.23 (m, 4H), 7.11 (d, J=8.4 Hz, 1H), 6.84 (t, J=3.8 Hz, 4H), 6.11 (s, 2H), 3.75 (q, J=6.0 Hz, 2H), 3.20 (t, J=7.0 Hz, 2H), 2.29 (s, 6H). $^{13}$C NMR (400 MHz, d$_6$-DMSO) δ=168.6, 161.2, 160.4, 159.5, 157.3, 150.3, 149.7, 149.1, 142.6, 137.7, 136.8, 136.5, 134.9, 132.2, 131.8, 131.7, 131.3, 127.8, 127.3, 124.5, 124.1, 123.3, 118.5, 59.4, 47.7, 39.0, 25.5.

Synthesis of 6-chloro-2-(4-(4-chloro-3,5-dimethylphenoxy)benzyl)-N-((3-morpholino-4-nitrophenyl)sulfonyl)-2H-indazole-3-carboxamide (41)

Follow General Procedure 2 with 12 (0.23 mmol) and 23. The product was purified via flash column chromatography in a gradient of 92:7:1 DCM/MeOH/NH$_4$OH. Yield=92 mgs, 57% (yellow solid). H NMR (400 MHz, DMSO) δ=8.29 (s, 1H), 7.86 (d, J=8.8 Hz, 1H), 7.76 (s, 1H), 7.67 (d, J=9.2 Hz, 1H), 7.57 (d, J=9.2 Hz, 1H), 7.25 (d, J=9.2 Hz, 3H), 6.87 (d, J=11.2 Hz, 4H), 6.09 (s, 2H), 3.66 (bs, 4H), 2.98 (bs, 4H), 2.28 (s, 6H). $^{13}$C NMR (400 MHz, d$_6$-DMSO) δ=168.0, 163.9, 156.6, 154.7, 150.5, 145.6, 144.9, 143.7, 137.9, 133.0, 131.6, 130.3, 128.7, 127.5, 127.0, 125.9, 123.0, 122.5, 120.7, 119.7, 119.4, 118.5, 66.4, 51.8, 20.7.

Synthesis of 6-chloro-2-(4-(4-chloro-3,5-dimethylphenoxy)benzyl)-N-((3-((furan-2-ylmethyl)amino)-4-nitrophenyl)sulfonyl)-2H-indazole-3-carboxamide (42)

Follow General Procedure 2 with 12 (0.23 mmol) and 24. The product was purified via flash column chromatography in a gradient of 92:7:1 DCM/MeOH/NH$_4$OH. Yield=82 mgs, 50% (yellow solid). $^1$H NMR (400 MHz, DMSO) δ=8.53 (t, J=5.8 Hz, 1H), 8.31 (s, 1H), 8.10 (d, J=8.8 Hz, 1H), 7.67 (d, J=9.2 Hz, 1H), 7.61 (s, 1H), 7.48 (s, 1H), 7.27 (d, J=8.0 Hz, 3H), 7.11 (d, J=9.2 Hz, 1H), 6.86 (t, J=8.0 Hz, 4H), 6.29 (d, J=2.4 Hz, 1H), 6.19 (s, 1H), 6.10 (s, 2H), 4.60 (d, J=5.6 Hz, 2H), 2.28 (s, 6H). $^{13}$C NMR (400 MHz, d$_6$-DMSO) δ=163.8, 156.5, 154.8, 152.9, 151.5, 145.5, 144.6, 142.9, 137.8, 133.1, 132.2, 131.7, 130.2, 128.6, 127.4, 126.94, 126.89, 123.1, 122.6, 119.7, 119.3, 118.6, 114.1, 113.3, 110.8, 108.2, 40.6, 20.7.

Synthesis of 6-chloro-2-(4-(4-chloro-3,5-dimethylphenoxy)benzyl)-N-((3-((2-(furan-2-yl)ethyl)amino)-4-nitrophenyl)sulfonyl)-2H-indazole-3-carboxamide (43)

Follow General Procedure 2 with 12 (0.23 mmol) and 25. The product was purified via flash column chromatography in a gradient of 92:7:1 DCM/MeOH/H$_2$O. Yield=87 mgs, 52% (yellow solid). $^1$H NMR (400 MHz, d$_6$-DMSO) δ=8.27 (br, 1H), 8.24 (s, 1H), 8.14 (d, J=9.6 Hz, 1H), 7.72 (d, J=8.8 Hz, 1H), 7.62 (s, 1H), 7.51 (s, 1H), 7.30 (d, J=10.0 Hz, 1H), 7.27 (s, 1H), 7.23 (d, J=8.8 Hz, 2H), 7.10 (d, J=9.2 Hz, 1H), 6.84 (d, J=6.0 Hz, 4H), 6.34 (s, 1H), 6.21 (d, J=3.2 Hz, 1H), 6.05 (s, 2H), 3.66 (q, J=4.4 Hz, 2H), 3.05 (t, J=6.6 Hz, 2H), 2.23 (s, 6H). $^{13}$C NMR (400 MHz, d$_6$-DMSO) δ=161.3, 159.5, 150.3, 149.3, 147.1, 142.6, 134.9, 131.9, 127.7, 126.8, 124.6, 124.1, 123.3, 118.4, 115.6, 111.7, 60.9, 46.4, 31.9, 25.5.

Synthesis of 6-chloro-2-(4-(4-chloro-3,5-dimethylphenoxy)benzyl)-N-((3-(((1-methyl-1H-pyrazol-3-yl)methyl)amino)-4-nitrophenyl)sulfonyl)-2H-indazole-3-carboxamide (44)

Follow General Procedure 2 with 12 (0.23 mmol) and 26. The product was purified via flash column chromatography in a gradient of 92:7:1 DCM/MeOH/NH$_4$OH. Yield=78 mgs, 47% (yellow solid). H NMR (400 MHz, d$_6$-DMSO) δ=8.42 (t, J=5.6 Hz, 1H), 8.33 (s, 1H), 8.11 (d, J=9.6 Hz, 1H), 7.67 (t, J=11.8 Hz, 3H), 7.45 (s, 1H), 7.28 (t, J=7.0 Hz, 3H), 7.08 (d, J=8.8 Hz, 1H), 6.88 (d, J=8.4 Hz, 2H), 6.85 (s, 2H), 6.14 (s, 2H), 4.44 (d, J=4.4 Hz, 2H), 3.71 (s, 3H), 2.29 (s, 6H). $^{13}$C NMR (400 MHz, d$_6$-DMSO) δ=163.8, 156.5, 152.9, 145.5, 144.6, 138.5, 137.8, 133.1, 131.8, 130.2, 130.0, 128.6, 127.4, 126.9, 123.1, 122.6, 119.7, 119.3, 118.6, 118.0, 113.7, 113.5, 54.6, 37.4, 20.7.

Synthesis of 6-chloro-2-(4-(4-chloro-3,5-dimethylphenoxy)benzyl)-N-((4-nitro-3-((pyridin-3-ylmethyl)amino)phenyl)sulfonyl)-2H-indazole-3-carboxamide (45)

Follow General Procedure 2 with 12 (0.23 mmol) and 27. The product was purified via flash column chromatography in a gradient of 92:7:1 DCM/MeOH/NH$_4$OH. Yield=66 mgs, 40% (yellow solid). $^1$H NMR (400 MHz, DMSO) δ=8.72 (s, 1H), 8.25 (s, 1H), 8.11 (d, J=8.4 Hz, 1H), 7.74 (bs, 2H), 7.68 (d, J=8.4 Hz, 1H), 7.45 (s, 1H), 7.25 (d, J=7.6 Hz, 4H), 7.08 (d, J=8.8 Hz, 1H), 6.85 (t, J=7.2 Hz, 4H), 6.07 (s, 2H), 4.66 (s, 2H), 2.27 (s, 6H). $^{13}$C NMR (400 MHz, d$_6$-DMSO) δ=168.5, 161.2, 159.5, 157.7, 153.6, 153.2, 150.3, 149.3, 142.6, 140.3, 139.2, 137.8, 137.1, 136.4, 135.0, 132.2, 131.7, 128.8, 128.4, 127.8, 127.4, 124.4, 124.1, 123.3, 118.7, 118.1, 59.4, 48.8, 25.5.

Synthesis of 6-chloro-2-(4-(4-chloro-3,5-dimethylphenoxy)benzyl)-N-((4-nitro-3-((2-(pyridin-3-yl)ethyl)amino)phenyl)sulfonyl)-2H-indazole-3-carboxamide (46)

Follow General Procedure 2 with 12 (0.23 mmol) and 28. The product was purified via flash column chromatography in a gradient of 84:14:2 DCM/MeOH/NH$_4$OH. Yield=64 mgs, 38% (yellow solid). $^1$H NMR (400 MHz, d$_6$-DMSO) δ=8.31 (s, 1H), 8.23 (t, J=5.6 Hz, 1H), 8.11 (d, J=8.4 Hz, 1H), 7.88 (d, J=8.0 Hz, 1H), 7.72 (s, 1H), 7.67 (d, J=9.2 Hz, 1H), 7.46 (s, 1H), 7.33 (s, 1H), 7.25 (d, J=10.8 Hz, 3H), 7.21 (s, 1H), 7.11 (d, J=9.2 Hz, 1H), 6.83 (d, J=8.4 Hz, 4H), 6.10 (s, 2H), 3.68 (q, J=7.2 Hz, 2H), 3.07 (t, J=7.0 Hz, 2H), 2.29 (s, 6H). $^{13}$C NMR (400 MHz, d$_6$-DMSO) δ=168.6, 162.7, 161.2, 159.5, 157.4, 153.0, 150.8, 150.3, 149.3, 143.9, 142.6, 137.7, 136.7, 136.5, 134.9, 133.4, 132.2, 131.8, 131.7, 129.6, 127.8, 127.3, 124.5, 124.1, 123.2, 118.5, 118.4, 76.1, 59.4, 48.5, 36.3, 25.5.

Synthesis of 6-chloro-2-(4-(4-chloro-3,5-dimethylphenoxy)benzyl)-N-((4-nitro-3-((pyridin-4-ylmethyl)amino)phenyl)sulfonyl)-2H-indazole-3-carboxamide (47)

Follow General Procedure 2 with 12 (0.23 mmol) and 29. The product was purified via flash column chromatography in a gradient of 84:14:2 DCM/MeOH/NH$_4$OH. Yield=58 mgs, 35% (yellow solid). H NMR (400 MHz, d$_6$-DMSO) δ=8.83 (t, J=6.2 Hz, 1H), 8.63 (d, J=5.2 Hz, 2H), 8.24 (s, 1H), 8.17 (d, J=8.4 Hz, 1H), 7.77 (d, J=5.6 Hz, 2H), 7.69 (d, J=8.8 Hz, 1H), 7.30-7.23 (m, 4H), 7.14 (d, J=8.0 Hz, 1H), 6.90-6.86 (m, 4H), 6.04 (s, 2H), 4.88 (d, J=6.4 Hz, 2H), 2.30 (s, 6H). $^{13}$C NMR (400 MHz, d$_6$-DMSO) δ=168.35, 161.25, 159.51, 157.59, 150.24, 149.84, 148.93, 142.59, 137.76, 136.30, 134.94, 132.17, 131.89, 131.71, 128.92, 127.69, 127.28, 124.45, 124.09, 123.57, 123.35, 119.14, 117.95, 59.29, 50.41, 25.50.

Synthesis of 6-chloro-2-(4-(4-chloro-3,5-dimethylphenoxy)benzyl)-N-((4-nitro-3-((2-(pyridin-4-yl)ethyl)amino)phenyl)sulfonyl)-2H-indazole-3-carboxamide (48)

Follow General Procedure 2 with 12 (0.23 mmol) and 30. The product was purified via flash column chromatography in a gradient of 84:14:2 DCM/MeOH/NH$_4$OH. Yield=61 mgs, 36% (yellow solid). H NMR (400 MHz, d$_6$-DMSO) δ=8.65 (d, J=4.0 Hz, 2H), 8.61 (s, 1H), 8.43 (t, J=5.4 Hz, 1H), 8.29 (s, 1H), 8.02 (d, J=9.6 Hz, 1H), 7.67 (d, J=8.8 Hz, 1H), 7.64 (d, J=4.8 Hz, 2H), 7.30-7.24 (m, 5H), 6.73 (d, J=8.8 Hz, 2H), 6.82 (s, 2H), 6.12 (s, 2H), 3.73 (q, J=6.4 Hz, 2H), 3.09 (t, J=7.2 Hz, 2H), 2.27 (s, 6H). $^{13}$C NMR (400 MHz, d$_6$-DMSO) δ=168.1, 161.2, 159.6, 158.3, 151.1, 150.8, 150.2, 142.6, 140.1, 137.8, 137.2, 136.4, 135.1, 134.8, 132.1, 131.7, 131.1, 130.9, 127.7, 127.3, 124.4, 123.9, 123.4, 119.2, 59.3, 47.6, 39.0, 25.5.

Synthesis of 6-chloro-2-(4-(4-chloro-3,5-dimethylphenoxy)benzyl)-2H-indazole-3-carboxylic acid (49)

6-chloro-1H-indazole-3-carboxylic acid (2.55 mmol) underwent General Procedure 1 and General Procedure 2 with 9b to create methyl 6-chloro-2-(4-(4-chloro-3,5-dimethylphenoxy)benzyl)-2H-indazole-3-carboxylate. Yield=522 mgs, 45% (yellow oil). The resulting product was purified in a gradient of 2:1 Hexanes/Ethyl Acetate and then used in General Procedure 3 to yield the purified product. Yield=460 mgs, 91% (white solid). $^1$H NMR (400 MHz, d$_6$-DMSO) δ=8.07 (d, J=9.2 Hz, 1H), 7.91 (s, 1H), 7.34 (d, J=8.8 Hz, 3H), 6.98 (d, J=8.4 Hz, 2H), 6.88 (s, 2H), 6.09 (s, 2H), 2.30 (6H). $^{13}$C NMR (400 MHz, d$_6$-DMSO) δ=168.5, 161.6, 159.4, 146.0, 142.6, 141.8, 137.1, 136.7, 134.7, 133.5, 128.7, 128.5, 127.1, 124.2, 123.7, 115.6, 57.0, 25.5.

Synthesis of 5-chloro-1-(4-(4-chloro-3,5-dimethylphenoxy)benzyl)-1H-indazole-3-carboxylic acid (50)

Follow General Procedure 4 with 8 (0.95 mmol) and 9b expect isolate the N1-alkylated isomer. Yield=229 mgs, 53% (yellow oil). The N1-alkylated isomer was then used in General Procedure 3 to yield the purified product. Yield=209 mgs, 94% (white solid). $^1$H NMR (400 MHz, d$_6$-DMSO) δ=13.32 (s, 1H), 8.08 (s, 1H), 7.98 (d, J=8.4 Hz, 1H), 7.54 (d, J=9.6 Hz, 1H), 7.33 (d, J=8.4 Hz, 2H), 6.98 (d, J=7.6 Hz, 2H), 6.87 (s, 2H), 5.78 (s, 2H), 2.29 (s, 6H). $^{13}$C NMR (400 MHz, d$_6$-DMSO) δ=168.2, 161.6, 159.4, 144.2, 142.6, 140.0, 136.5, 134.7, 133.5, 133.0, 132.4, 129.2, 125.6, 124.2, 123.7, 118.0, 57.3, 25.5.

Synthesis of 5-chloro-1-(4-(4-chloro-3,5-dimethylphenoxy)benzyl)-N-((4-morpholino-3-nitrophenyl)sulfonyl)-1H-indazole-3-carboxamide (51)

Follow General Procedure 2 with 50 (0.23 mmol) and 14. The product was purified via flash column chromatography in a gradient of 92:7:1 DCM/MeOH/H$_2$O. Yield=85 mgs, 53% (yellow solid). $^1$H NMR (400 MHz, d$_6$-DMSO) δ=8.34 (s, 1H), 8.27 (s, 1H), 8.05 (d, J=8.8 Hz, 1H), 7.83 (d, J=8.8 Hz, 1H), 7.43 (d, J=8.4 Hz, 1H), 7.36 (d, J=9.6 Hz, 1H), 7.29 (d, J=8.4 Hz, 2H), 6.94 (d, J=8.0 Hz, 2H), 6.86 (s, 2H), 5.68 (s, 2H), 3.71 (bs, 4H), 3.11 (bs, 4H), 2.29 (s, 6H). $^{13}$C NMR (400 MHz, d$_6$-DMSO) δ=177.3, 156.7, 154.7, 147.1, 139.7, 139.3, 137.9, 135.6, 133.0, 132.3, 129.8, 128.7, 127.0, 126.1, 124.2, 122.3, 120.5, 119.4, 118.9, 112.5, 66.3, 52.2, 51.3, 20.7.

Synthesis of 5-chloro-1-(4-(4-chloro-3,5-dimethylphenoxy)benzyl)-N-((3-nitro-4-((pyridin-3-ylmethyl)amino)phenyl)sulfonyl)-1H-indazole-3-carboxamide (52)

Follow General Procedure 2 with 50 (0.23 mmol) and 19. The product was purified via flash column chromatography in a gradient of 92:7:1 DCM/MeOH/H$_2$O. Yield=103 mgs, 62% (yellow solid). $^1$H NMR (400 MHz, d$_6$-DMSO) δ=9.15 (bs, 1H), 8.71 (s, 1H), 8.67 (s, 1H), 8.48 (s, 1H), 8.10 (s, 1H), 7.96 (d, J=8.8 Hz, 1H), 7.89 (d, J=8.4 Hz, 1H), 7.81 (d, J=7.2 Hz, 1H), 7.48 (d, J=8.4 Hz, 1H), 7.34 (d, J=7.6 Hz, 3H), 7.10 (d, J=9.2 Hz, 1H), 6.95 (d, J=8.0 Hz, 2H), 6.86 (s, 2H), 5.73 (s, 2H), 4.85 (s, 1H), 4.76 (s, 2H), 2.29 (s, 6H). $^{13}$C NMR (400 MHz, d$_6$-DMSO) δ=167.4, 161.6, 159.4, 153.7, 153.5, 151.7, 144.2, 142.6, 140.2, 139.6, 138.8, 136.5, 135.5, 134.7, 133.5, 132.7, 132.4, 128.8, 126.0, 124.2, 123.6, 120.1, 117.8, 76.3, 57.3, 48.6, 25.5.

Fluorescence Polarization Competition Assay:

The fluorescence polarization assays were performed in 96 well polypropylene F-bottom black microplates (Greiner Bio-One) with a final volume of 100 µL. During the competition assay, a fluorescently-labeled Bak-BH3 peptide (FITC-Ahx-GQVGRQLAIIGDDINR-CONH$_2$, hereafter "FITC-Bak", where FITC=fluorescein isocyanate; Ahx=6-aminohexanoyl linker) was competed off of either MCL-1$^{172-327}$, BCL-X$_L^{1-212}$ or BCL-2$^{1-211}$ with the synthesized inhibitors. The binding affinities of FITC-Bak to MCL-1, BCL-X$_L$ and BCL-2 were determined via a fluorescence polarization assay where various concentrations of the selected proteins were titrated into solutions of 10 nM FITC-Bak in 20 mM HEPES, pH 6.8, 50 mM NaCl, 3 mM DTT, 0.01% Triton X-100 and 5% DMSO at room temperature. The changes in the fluorescence polarization were then measured using a BMG PHERAstar FS multimode microplate reader equipped with two PMTs for simultaneous measurements of both the perpendicular and parallel fluorescence emission at a 485 nm excitation and 520 nm emission filter. Regression analysis was then performed on the polarization data using Origin (OriginLab, Northampton, Mass.) and the data was fitted to the Hill equation, thus producing binding curves for FITC-Bak with MCL-1, BCL- $X_L$ and BCL-2. FITC-Bak's $K_d$'s were then determined to be 42 nM for MCL-1, 6 nM for BCL-$X_L$ and 33 nM for BCL-2.

The fluorescence polarization competition assays were setup using a Biomek FXP Automated Liquid Handling System. Protein concentrations of either 100 nM of MCL-1, 15 nM of BCL-$X_L$ or 75 nM of BCL-2 with 10 nM of FITC-Bak (in 20 mM HEPES, pH 6.8, 50 mM NaCl, 3 mM DTT, 0.01% Triton X-100 and 1% DMSO) were chosen and various concentrations of the inhibitors were titrated into the solutions. Wells possessing only the peptide, only the desired protein and both the peptide plus the desired protein without inhibitor were used as controls. Changes in fluorescence polarization were measured after 4 hours of incubation at room temperature using the BMG PHERAstar FS multimode plate reader previously mentioned and regression analysis was performed using Prism 8 (Graphpad) with the data fitted to a sigmoidal curve to determine inhibitor $IC_{50}$ values. The $IC_{50}$ values were then converted to $K_i$ values using an equation derived by Nikolovska-Coleska et al. All inhibitors were tested in triplicate.

REFERENCES

1. Shamas-Din, A., Kale, J., Leber, B., and Andrews, D. W., "Mechanisms of Action of Bcl-2 Family Proteins". *Cold Spring Harbor Perspectives in Biology,* 2013, 5, 4.
2. Hanahan, D. and Weinberg, R. "Hallmarks of Cancer: The Next Generation". *Cell* 2011, 144, 5, pp. 646-674.
3. Gross, A., McDonnell, J. M., and Korsmeyer, S. J. "BCL-2 Family Members and the Mitochondria in Apoptosis". *Genes & Development.* 1999, 13, 15, pp. 1899-1911.
4. Ashkenazi, A., Fairbrother, W. J., Leverson, J. D., and Souers, A. J. "From Basic Apoptosis Discoveries to Advanced Selective BCL-2 Family Inhibitors". *Nature Reviews Drug Discovery,* 2017, 16, 4, pp. 273-84.
5. Delbridge, A. R. D., and Strasser, A. "The BCL-2 Protein Family, BH3-Mimetics and Cancer Therapy". *Cell Death and Differentiation,* 2015, 22, 7, pp. 1071-80.
6. Tse, C., Shoemaker, A. R., Adickes, J., Anderson, M. G., et al. "ABT-263: A Potent and Orally Bioavailable Bcl-2 Family Inhibitor." *Cancer Research,* 2008, 68, 9, pp. 3421-3428.
7. Shoemaker, A. R., Mitten, M. J., Adickes, J., Oleksijew, A., Zhang, H., et al. "The Bcl-2 Family Inhibitor ABT-263 Shows Significant but Reversible Thrombocytopenia in Mice." *Blood,* 2006, 108, 11, p. 1107.
8. Souers, A. J., Leverson, J. D., Boghaert, E. R., Ackler, S. L., Catron, N. D., Chen, J., Dayton, B. D., et al. "ABT-199, a Potent and Selective BCL-2 Inhibitor, Achieves Antitumor Activity while Sparing Platelets". *Nature Medicine,* 2013, 19, 2, pp. 202-208.
9. "FDA approves Venetoclax in Combination for AML in Adults". U.S Food and Drug Administration, 2018. https://www.fda.gov/drugs/fda-approves-venetoclax-combination-aml-adults.
10. Tahir, S. K., Smith, M. L., Hessler, P., Rapp, L. R., Idler, K. B., Park, C. H., Leverson, J. D., and Lam, L. T. "Potential Mechanisms of Resistance to Venetoclax and Strategies to Circumvent it". *BMC Cancer,* 2017, 17, 399.
11. Xiang, W., Yang, C., and Bai, L. "MCL-1 Inhibition in Cancer Treatment". *OncoTargets and Therapy,* 2018, 11, pp. 7301-7314.
12. Tron, A. E., Belmonte, M. A., Adam, A., Aquila, B. M., Boise, L. H., Chiarparin, E., Cidado, J., et al. "Discovery of Mcl-1-Specific Inhibitor AZD5991 and Preclinical Activity in Multiple Myeloma and Acute Myeloid Leukemia". *Nature Communications,* 2018, 9, 1, pp. 5341.
13. Caenepeel, S., Brown, S. P., Belmontes, B., Moody, G., Keegan, K. S., Chui, D., Whittington, D. A., et al. "AMG 176, a Selective MCL1 Inhibitor, Is Effective in Hematologic Cancer Models Alone and in Combination with Established Therapies". *Cancer Discovery,* 2018, 8, 12, pp. 1582-1597.
14. Ramsey, H. E., Fischer, M. A., Lee, T., Gorska, A. E., Arrate, M. P., Fuller, L., et al. "A Novel MCL-1 Inhibitor Combined with Venetoclax Rescues Venetoclax-Resistant Acute Myelogenous Leukemia". *Cancer Discovery,* 2018, 8, 12.
15. Prukova, D., Andrea, L., Nahacka, Z., Karolova, J., Svaton, M., Klanova, M., Havranek, O., et al. "Co-targeting of BCL-2 with Venetoclax and MCL-1 with S63845 is Synthetically Lethal In Vivo in Relapsed Mantle Cell Lymphoma". *Clinical Cancer Research,* 2019, https://doi.org/10.1158/1078-0432.CCR-18-3275.
16. Anighoro, A., Bajorath, J., and Rastelli, G. "Polypharmacology: Challenges and Opportunities in Drug Discovery". *Journal of Medicinal Chemistry,* 2014, 57, pp. 7874-7887.
17. Albert, A. A., Workman, P., Mestres, J., and Al-Lazikani, B. "Polypharmacology in Precision Oncology: Current Applications and Future Prospects". *Current Pharmaceutical Design,* 2016, 22, pp. 6935-6945.
18. Friberg, A., Vigil, D., Zhao, B., Daniels, N. R., Burke, J. P., Garcia-Barrantes, P. M., et al. "Discovery of Potent Myeloid Cell Leukemia 1 (MCL-1) Inhibitors Using Fragment-Based Methods and Structure-Based Design". *Journal of Medicinal Chemistry,* 2013, 56, pp. 15-30.
19. Pelz, N. F., Bian, Z., Zhao, B., Shaw, S., Tarr, J. C., Belmar, J., Gregg, C., et al. "Discovery of 2-Indole-Acylsulfonamide Myeloid Cell Leukemia 1 (Mcl-1) Inhibitors Using Fragment-Based Methods". *Journal of Medicinal Chemistry,* 2016, 59, 5, pp. 2054-2066.
20. Lee, E. F., Czabotar, P. E., Smith, B. J., Deshayes, K., Zobel, K., Colman, P. M., and Fairlie, W. D. "Crystal Structure of ABT-737 Complexed with BCL-$X_L$: Implications for Selectivity of Antagonists of the Bcl-2 Family". *Cell Death & Differentiation,* 2007, 14, pp. 1711-1713.
21. Longworth, M., Banister, S. D., Mack, J. B. C., Glass, M., Connor, M., and Kassiou, M. "The 2-Alkyl-2H-Indazole Regioisomers of Synthetic Cannabinoids AB-CHMINACA, AB-FUBINACA, AB-PINACA, and 5F-AB-PINACA are Possible Manufacturing Impurities with Cannabimimetic Activities". *Forensic Toxicology,* 2016, 34, pp. 286-303.
22. Cheung, M., Boloor, A., and Stafford, J. A. "Efficient and Regioselective Synthesis of 2-Alkyl-2H-Indazoles". *Journal of Organic Chemistry,* 2003, 68, 10, pp. 4093-4095.
23. Kotschy, A., Szlavik, Z., Murray, J., Davidson, J., Maragno, A. L., Toumelin-Braizat, G., Chanrion, M., et al. "The MCL1 Inhibitor S63845 Is Tolerable and Effective in Diverse Cancer Models." *Nature,* 2016, 538, 7626, pp. 477-482.
24. Hird, A. W., and Tron, A. E. "Recent Advances in the Development of MCL-1 Inhibitors for Cancer Therapy". *Pharmacology & Therapeutics,* 2019, 198, pp. 59-67.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

The invention claimed is:

1. A compound of formula (I), or a pharmaceutically acceptable salt, solvate, hydrate, cocrystal, or prodrug thereof:

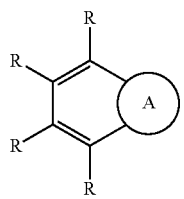
(I)

wherein:

A is a substituted heterocycle selected from:

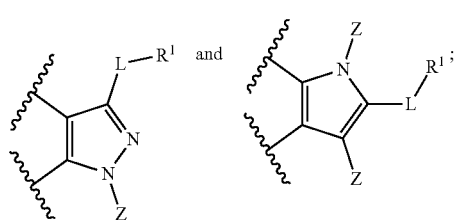

L is —C(O)NR$^a$SO$_2$— or —C(O)O—; and

R, R$^1$, R$^a$, and Z are independently selected at each occurrence from H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl, wherein one of Z is

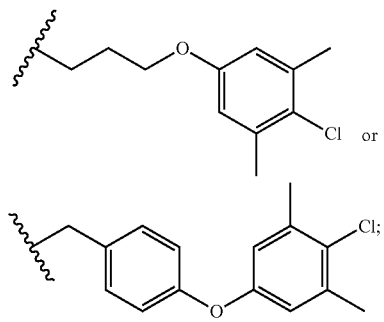

with the proviso that when A is

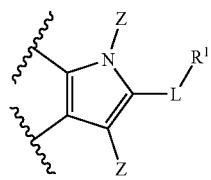

and Z bonded to the carbon atom is

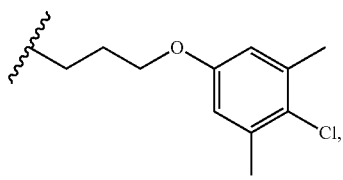

the compound of formula (I) is limited by at least one of i) or ii):

i) R$^1$ is

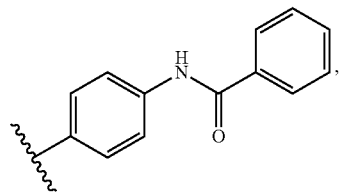 [SMILES: *c1ccc(NC(=O)c2ccccc2)cc1]

or the optional substituent of R$^1$ is selected from

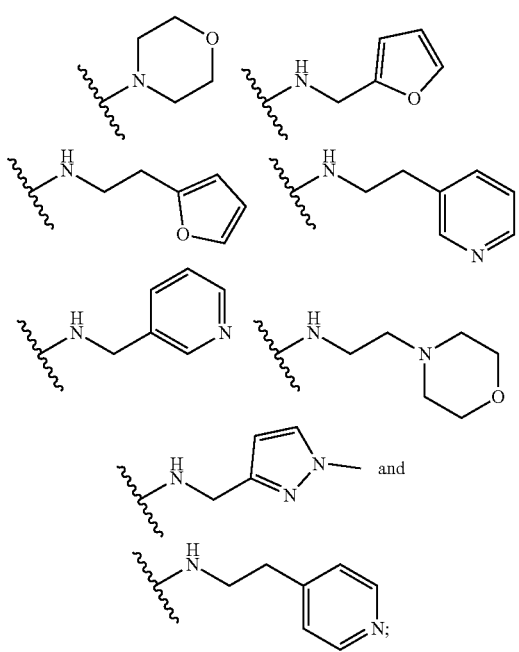

ii) $R^1$ is a group selected from:

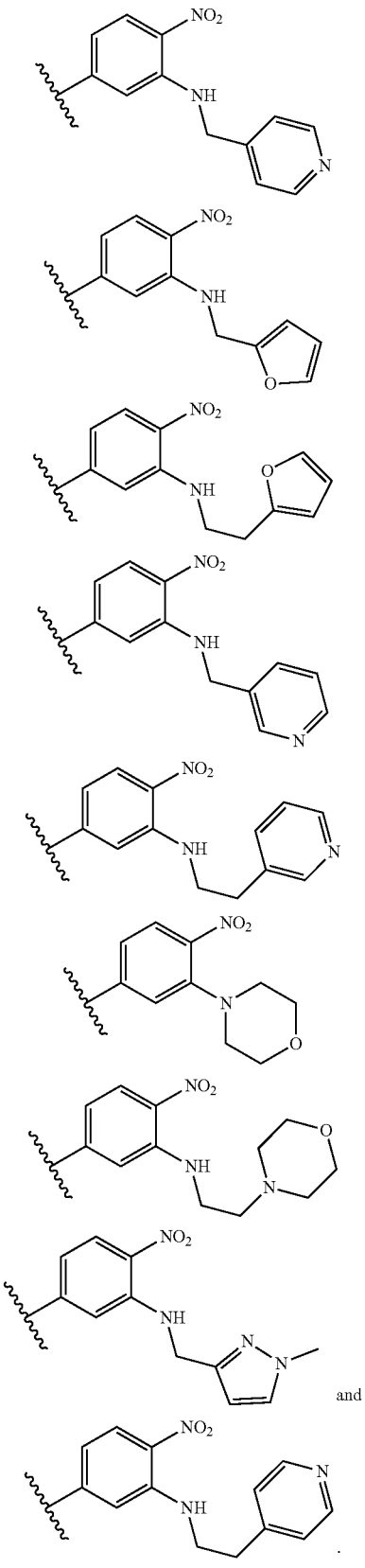

and

2. The compound of claim 1, or a pharmaceutically acceptable salt, solvate, hydrate, cocrystal, or prodrug thereof, wherein $R^1$ is selected from H, alkyl, and substituted aryl.

3. The compound of claim 1, or a pharmaceutically acceptable salt, solvate, hydrate, cocrystal, or prodrug thereof, wherein when A is

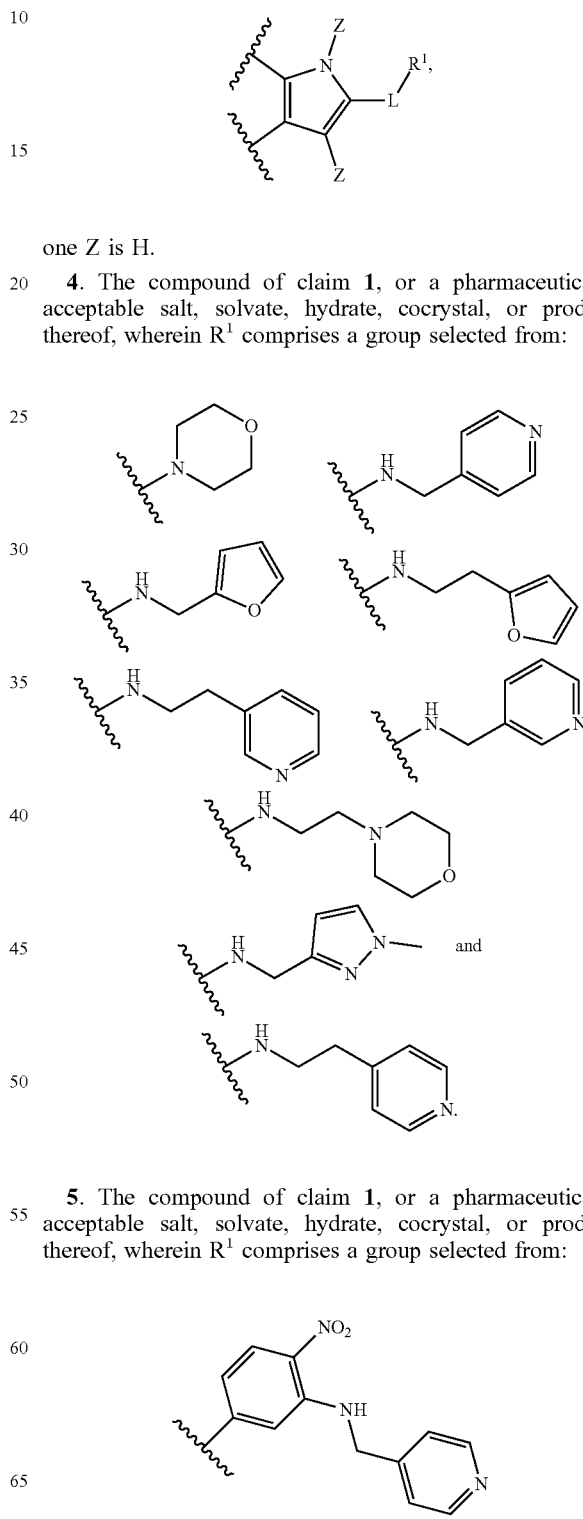

one Z is H.

4. The compound of claim 1, or a pharmaceutically acceptable salt, solvate, hydrate, cocrystal, or prodrug thereof, wherein $R^1$ comprises a group selected from:

and

5. The compound of claim 1, or a pharmaceutically acceptable salt, solvate, hydrate, cocrystal, or prodrug thereof, wherein $R^1$ comprises a group selected from:

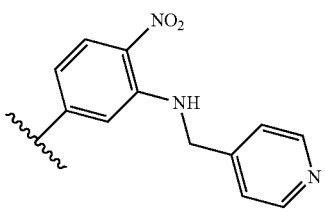

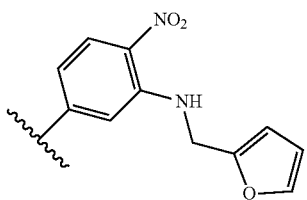

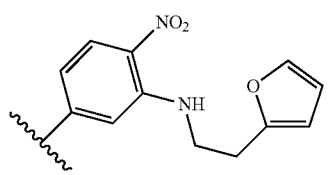

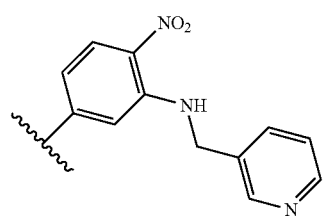

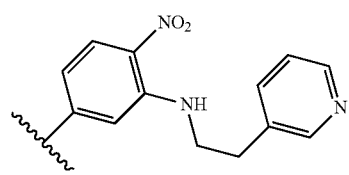

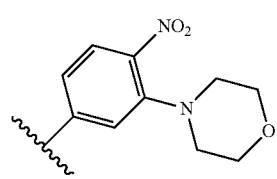

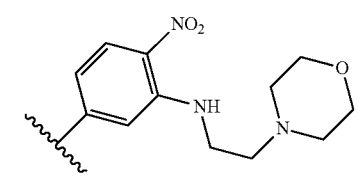

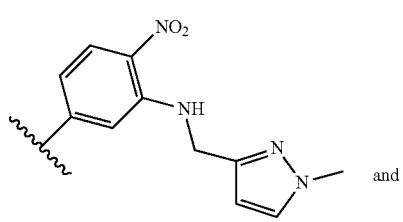 and

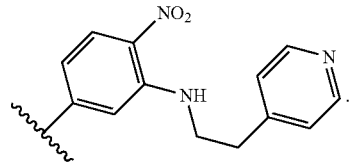

6. The compound of claim 1, or a pharmaceutically acceptable salt, solvate, hydrate, cocrystal, or prodrug thereof, wherein Z is

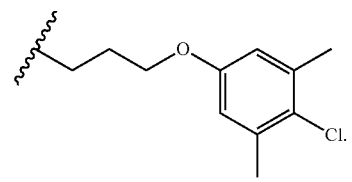 [SMILES: *CCCOc1cc(C)c(Cl)c(C)c1]

7. The compound of claim 1, or a pharmaceutically acceptable salt, solvate, hydrate, cocrystal, or prodrug thereof, wherein Z comprises a group selected from:

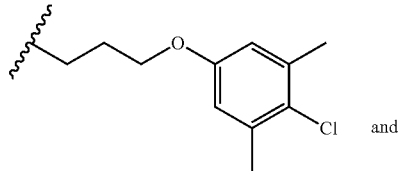 and

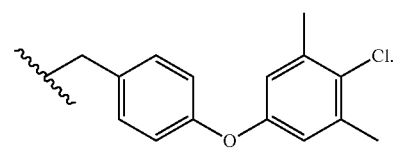

8. The compound of claim 1, or a pharmaceutically acceptable salt, solvate, hydrate, cocrystal, or prodrug thereof, wherein the compound of formula (I) is selected from Table 1, wherein R is independently selected from H, a halogen, and —COCH$_3$; and Z is independently selected from H, halogen, optionally substituted alkyl, optionally substituted cycloalkyl, optionally substituted aralkyl, and optionally substituted heteroaryl, wherein one of Z is

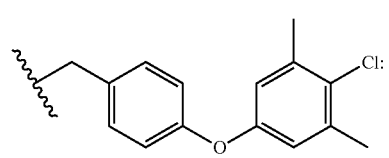

TABLE 1
| Compound # | A | L | R¹ |
|---|---|---|---|
| 1002 | 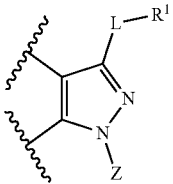 | —C(O)O— | H |
| 1008 | 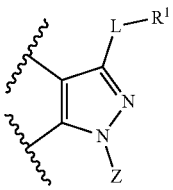 | —C(O)NHSO₂— | 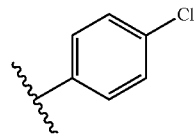 [SMILES: *c1ccc(Cl)cc1] |
| 1014 | 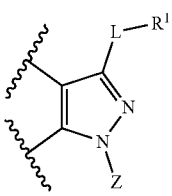 | —C(O)NHSO₂— | 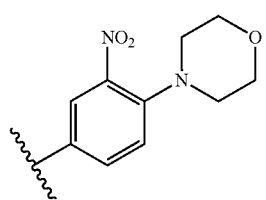 [SMILES: *c1ccc(N2CCOCC2)c([N+](=O)[O-])c1] |
| 1026 | 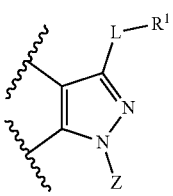 | —C(O)NHSO₂— | 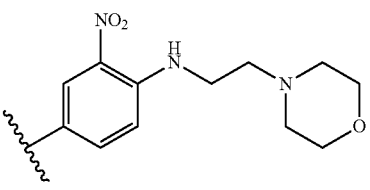 [SMILES: *c1ccc(NCCN2CCOCC2)c([N+](=O)[O-])c1] |
| 1032 | 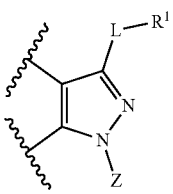 | —C(O)NHSO₂— | 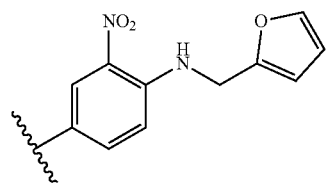 [SMILES: *c1ccc(NCc2ccco2)c([N+](=O)[O-])c1] |
| 1038 | 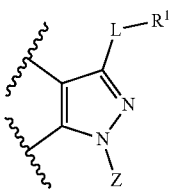 | —C(O)NHSO₂— | 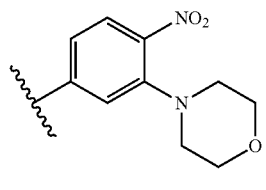 [SMILES: *c1ccc([N+](=O)[O-])c(N2CCOCC2)c1] |
| 1044 | 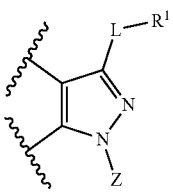 | —C(O)NHSO₂— | 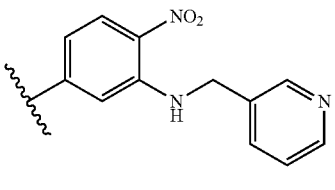 [SMILES: *c1ccc([N+](=O)[O-])c(NCc2cccnc2)c1] |
| 1050 | 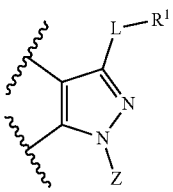 | —C(O)NHSO₂— | 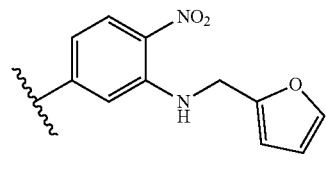 [SMILES: *c1ccc([N+](=O)[O-])c(NCc2ccco2)c1] |

TABLE 1-continued

| Compound # | A | L | R¹ |
| --- | --- | --- | --- |
| 1056 | pyrazole-A | —C(O)NHSO₂— | 4-(2-morpholinoethylamino)-3-nitrophenyl |
| 1062 | pyrazole-A | —C(O)NHSO₂— | 3-(4-ethylpiperazin-1-yl)-4-nitrophenyl |
| 1068 | pyrazole-A | —C(O)NHSO₂— | 4-benzamidophenyl |
| 1074 | pyrazole-A | —C(O)NHSO₂— | 4-(furan-2-ylamino)-3-nitrophenyl |
| 1080 | pyrazole-A | —C(O)NHSO₂— | 3-nitro-4-((tetrahydrofuran-2-yl)methylamino)phenyl |
| 1086 | pyrazole-A | —C(O)NHSO₂— | 3-nitro-4-(piperazin-1-yl)phenyl |
| 1092 | pyrazole-A | —C(O)NHSO₂— | 4-(methylamino)-3-nitrophenyl |

TABLE 1-continued

| Compound # | A | L | R¹ |
|---|---|---|---|
| 1097 | pyrrole (with Z, Z, N-L-R¹) | —C(O)O— | H |
| 1098 | pyrrole (with Z, Z, N-L-R¹) | —C(O)NHSO$_2$— | 4-chlorophenyl |
| 1099 | pyrrole (with Z, Z, N-L-R¹) | —C(O)NHSO$_2$— | 3-nitro-4-morpholinophenyl |
| 1100 | pyrrole (with Z, Z, N-L-R¹) | —C(O)NHSO$_2$— | 3-nitro-4-((pyridin-3-ylmethyl)amino)phenyl |
| 1101 | pyrrole (with Z, Z, N-L-R¹) | —C(O)NHSO$_2$— | 3-nitro-4-((2-morpholinoethyl)amino)phenyl |
| 1102 | pyrrole (with Z, Z, N-L-R¹) | —C(O)NHSO$_2$— | 3-nitro-4-((furan-2-ylmethyl)amino)phenyl |
| 1103 | pyrrole (with Z, Z, N-L-R¹) | —C(O)NHSO$_2$— | 4-nitro-3-morpholinophenyl |
| 1104 | pyrrole (with Z, Z, N-L-R¹) | —C(O)NHSO$_2$— | 4-nitro-3-((pyridin-3-ylmethyl)amino)phenyl |

TABLE 1-continued

| Compound # | A | L | R¹ |
|---|---|---|---|
| 1105 | | —C(O)NHSO$_2$— | |
| 1106 | | —C(O)NHSO$_2$— | |
| 1107 | | —C(O)NHSO$_2$— | |
| 1108 | | —C(O)NHSO$_2$— | |
| 1109 | | —C(O)NHSO$_2$— | |
| 1110 | | —C(O)NHSO$_2$— | |

TABLE 1-continued

| Compound # | A | L | R¹ |
|---|---|---|---|
| 1111 | pyrrole with Z, Z, L-R¹ | —C(O)NHSO₂— | nitrophenyl-piperazine |
| 1112 | pyrrole with Z, Z, L-R¹ | —C(O)NHSO₂— | nitrophenyl-NHMe |
| 1114 | pyrazole with L-R¹, Z | —C(O)O— | —CH₃ |
| 1119 | pyrrole with Z, Z, L-R¹ | —C(O)O— | —CH₃. |

9. The compound of claim 1, or a pharmaceutically acceptable salt, solvate, hydrate, cocrystal, or prodrug thereof, wherein the compound of formula (I) is selected from Table 2:

TABLE 2

NB-1-070

TABLE 2-continued

NB-1-084

TABLE 2-continued
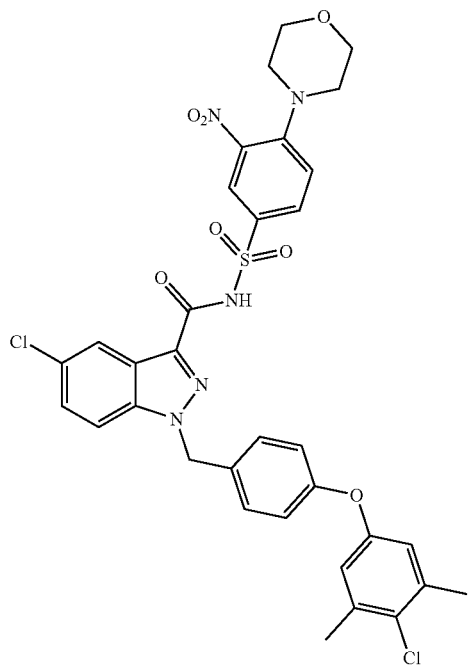 [SMILES: Cc1cc(Oc2ccc(Cn3nc(C(=O)NS(=O)(=O)c4ccc(N5CCOCC5)c([N+](=O)[O-])c4)c4cc(Cl)ccc43)cc2)cc(C)c1Cl]
NB-1-086
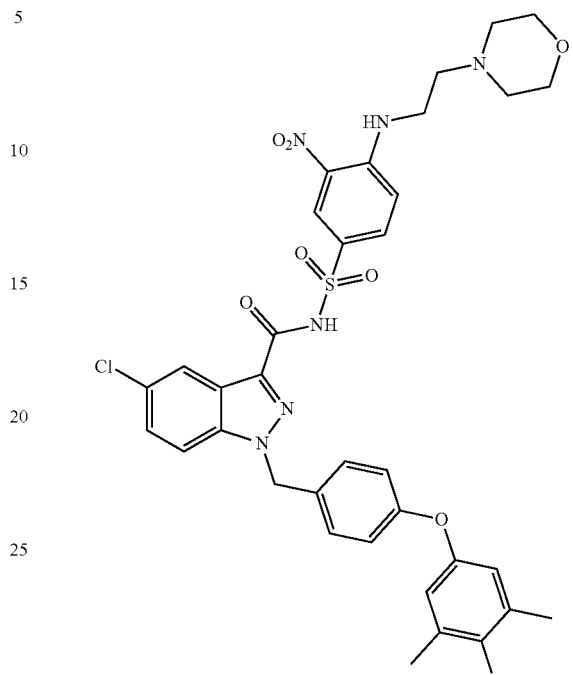
NB-1-088
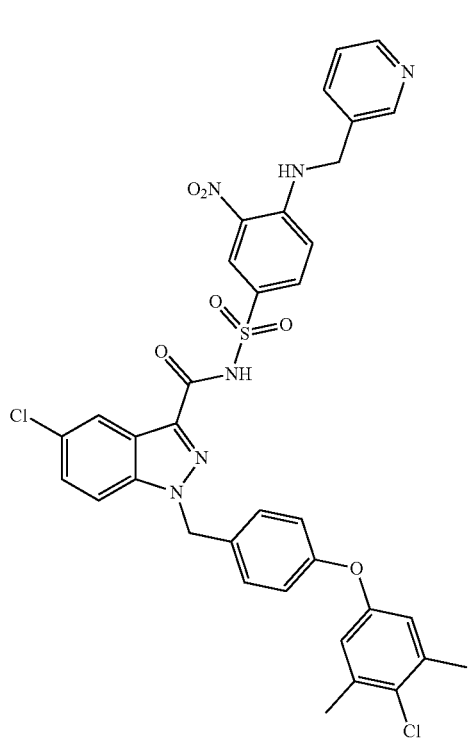 [SMILES: Cc1cc(Oc2ccc(Cn3nc(C(=O)NS(=O)(=O)c4ccc(NCc5cccnc5)c([N+](=O)[O-])c4)c4cc(Cl)ccc43)cc2)cc(C)c1Cl]
NB-1-087
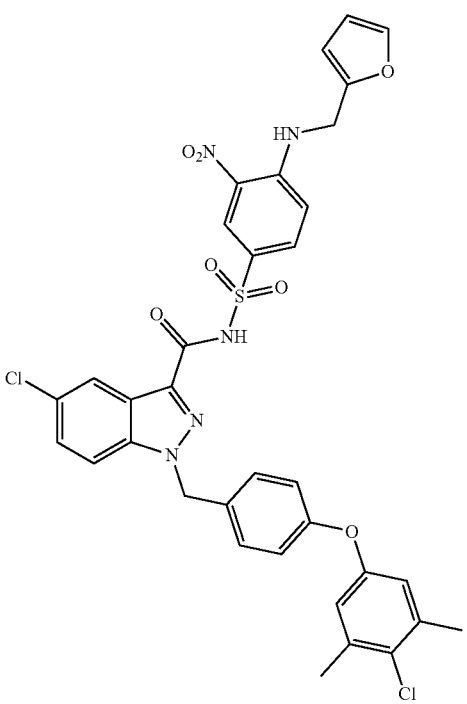 [SMILES: Cc1cc(Oc2ccc(Cn3nc(C(=O)NS(=O)(=O)c4ccc(NCc5ccco5)c([N+](=O)[O-])c4)c4cc(Cl)ccc43)cc2)cc(C)c1Cl]
NB-1-089

TABLE 2-continued
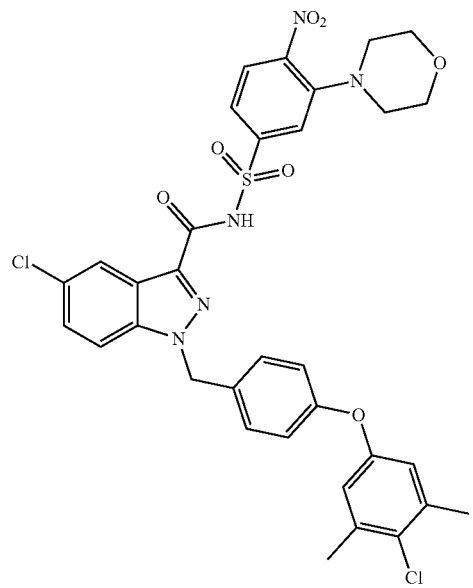 [SMILES: Cc1cc(Oc2ccc(Cn3nc(C(=O)NS(=O)(=O)c4ccc([N+](=O)[O-])c(N5CCOCC5)c4)c4cc(Cl)ccc43)cc2)cc(C)c1Cl]
CG-1-016
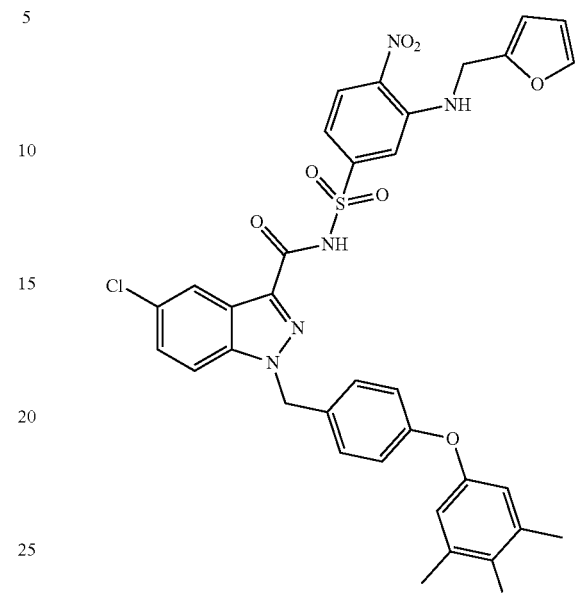
CG-1-019
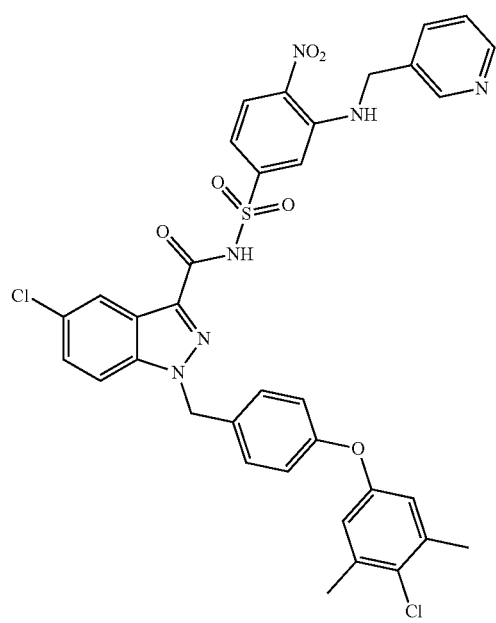 [SMILES: Cc1cc(Oc2ccc(Cn3nc(C(=O)NS(=O)(=O)c4ccc([N+](=O)[O-])c(NCc5cccnc5)c4)c4cc(Cl)ccc43)cc2)cc(C)c1Cl]
CG-1-018
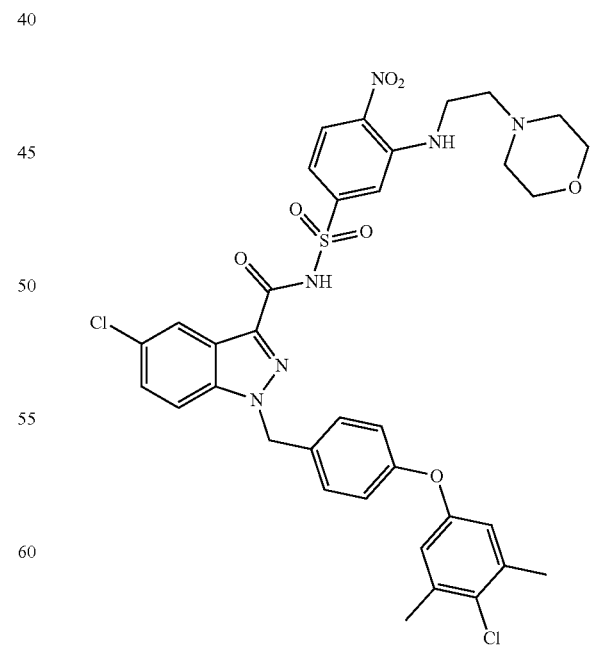
CG-1-022

TABLE 2-continued
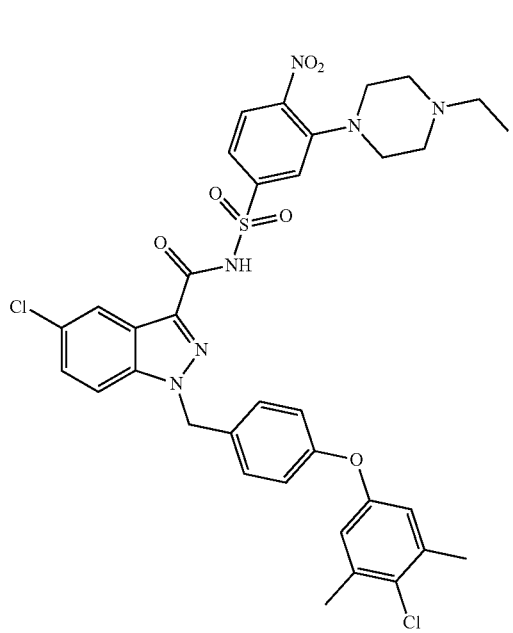 [SMILES: CCN1CCN(c2cc(S(=O)(=O)NC(=O)c3nn(Cc4ccc(Oc5cc(C)c(Cl)c(C)c5)cc4)c4ccc(Cl)cc34)ccc2[N+](=O)[O-])CC1]
CG-1-023
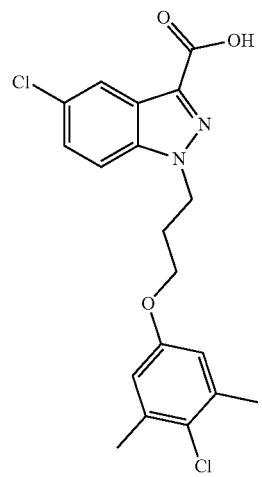
BD-3-173
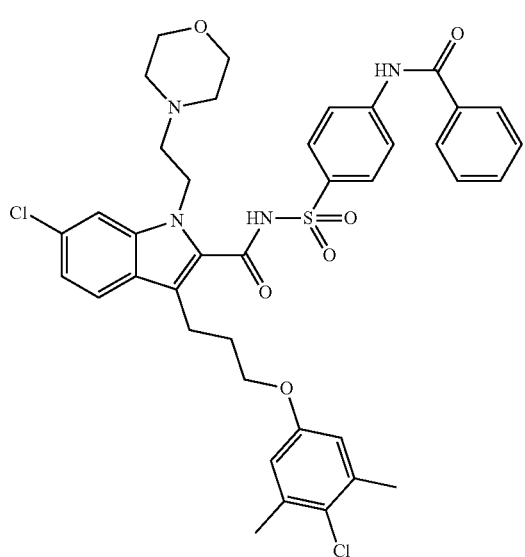 [SMILES: Cc1cc(OCCCc2c(C(=O)NS(=O)(=O)c3ccc(NC(=O)c4ccccc4)cc3)n(CCN3CCOCC3)c3cc(Cl)ccc23)cc(C)c1Cl]
GV-1-028
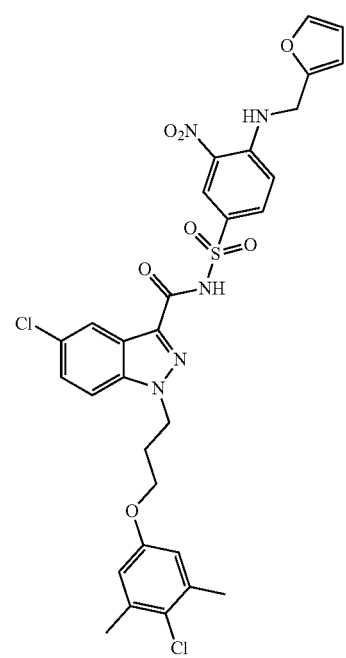 [SMILES: Cc1cc(OCCCn2nc(C(=O)NS(=O)(=O)c3ccc(NCc4ccco4)c([N+](=O)[O-])c3)c3cc(Cl)ccc32)cc(C)c1Cl]
BD-3-180

TABLE 2-continued
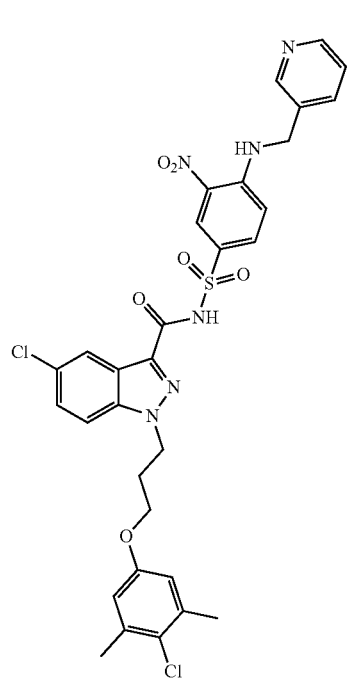 [SMILES: Cc1cc(OCCCn2nc(C(=O)NS(=O)(=O)c3ccc(NCc4cccnc4)c([N+](=O)[O-])c3)c3cc(Cl)ccc32)cc(C)c1Cl]
BD-3-181
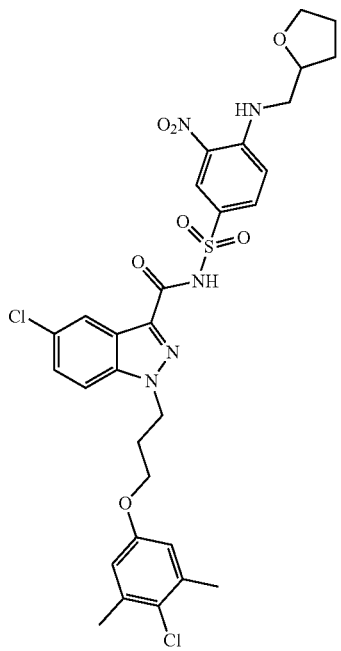
BD-3-184
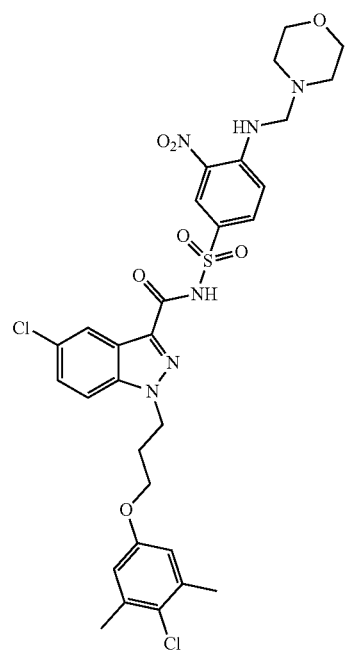 [SMILES: Cc1cc(OCCCn2nc(C(=O)NS(=O)(=O)c3ccc(NCN4CCOCC4)c([N+](=O)[O-])c3)c3cc(Cl)ccc32)cc(C)c1Cl]
BD-3-183
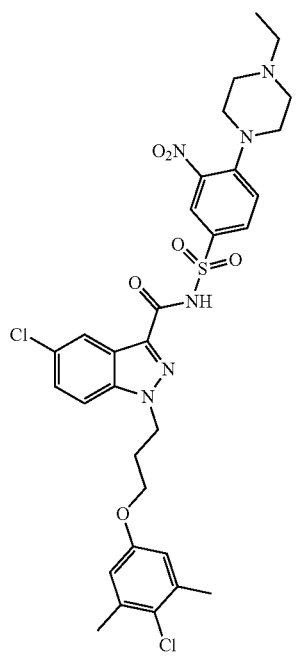 [SMILES: CCN1CCN(c2ccc(S(=O)(=O)NC(=O)c3nn(CCCOc4cc(C)c(Cl)c(C)c4)c4ccc(Cl)cc34)cc2[N+](=O)[O-])CC1]
BD-3-187

TABLE 2-continued
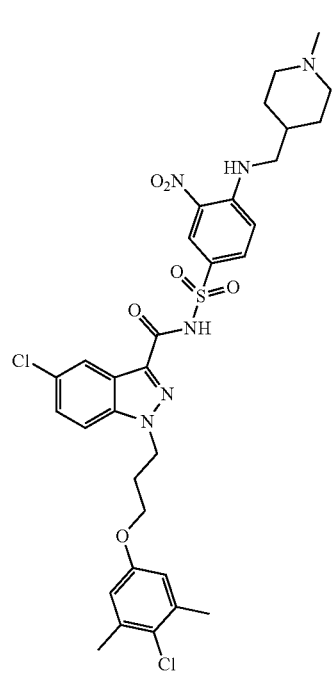 [SMILES: Cc1cc(OCCCn2nc(C(=O)NS(=O)(=O)c3ccc(NCC4CCN(C)CC4)c([N+](=O)[O-])c3)c3cc(Cl)ccc32)cc(C)c1Cl]
BD-3-190
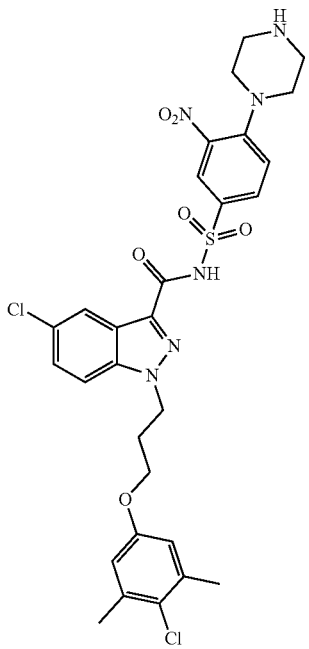
BD-3-187-b
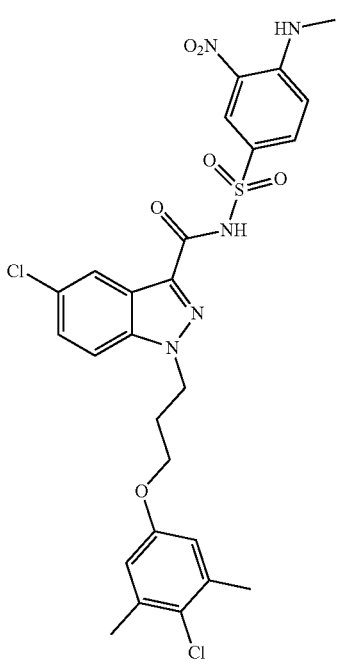 [SMILES: CNc1ccc(S(=O)(=O)NC(=O)c2nn(CCCOc3cc(C)c(Cl)c(C)c3)c3ccc(Cl)cc23)cc1[N+](=O)[O-]]
BD-3-190-b
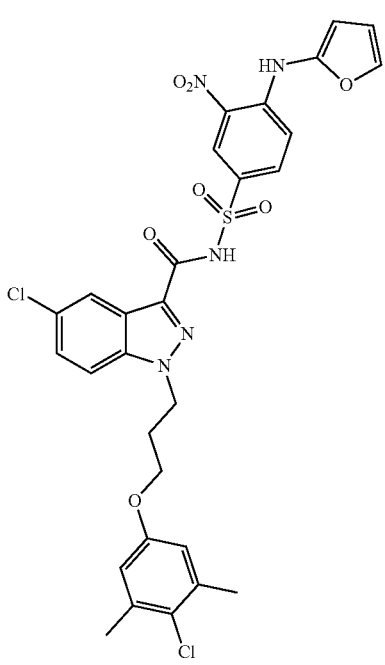 [SMILES: Cc1cc(OCCCn2nc(C(=O)NS(=O)(=O)c3ccc(Nc4ccco4)c([N+](=O)[O-])c3)c3cc(Cl)ccc32)cc(C)c1Cl]
BD-3-180-b TABLE 2-continued

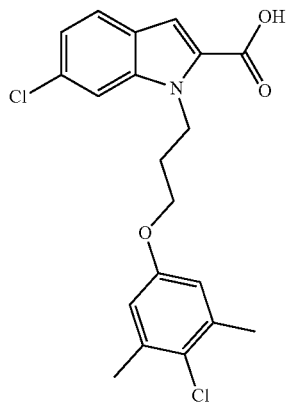 [SMILES: Cc1cc(OCCCn2c(C(=O)O)cc3ccc(Cl)cc32)cc(C)c1Cl]

2005

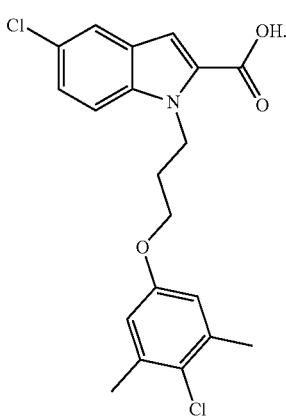 [SMILES: Cc1cc(OCCCn2c(C(=O)O)cc3cc(Cl)ccc32)cc(C)c1Cl]

2006

10. A pharmaceutical composition for treating leukemia, the pharmaceutical composition comprising one or more compounds according to claim 1, or a pharmaceutically acceptable salt, solvate, hydrate, cocrystal, or prodrug thereof, and a pharmaceutically acceptable carrier.

11. A pharmaceutical composition for treating lymphoma, the pharmaceutical composition comprising one or more compounds according to claim 1, or a pharmaceutically acceptable salt, solvate, hydrate, cocrystal, or prodrug thereof, and a pharmaceutically acceptable carrier.

12. The pharmaceutical composition of claim 11, wherein the lymphoma is non-Hodgkin's lymphoma.

13. The pharmaceutical composition of claim 10, wherein the leukemia is selected from myeloid leukemia, acute myeloid leukemia, acute lymphocytic leukemia, chronic lymphocytic leukemia, acute myelogenous leukemia, chronic myelogenous leukemia, chronic granulocytic leukemia, acute granulocytic leukemia, and hairy cell leukemia.

14. The compound of claim 1, or a pharmaceutically acceptable salt, solvate, hydrate, cocrystal, or prodrug thereof, wherein Z is

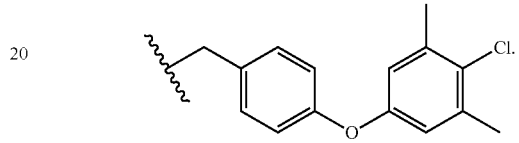

15. The compound of claim 1, or a pharmaceutically acceptable salt, solvate, hydrate, cocrystal, or prodrug thereof, wherein the compound of formula (I) is selected from Table 1, wherein R is independently selected from H, a halogen, and —COCH$_3$; and Z is independently selected from H, halogen, optionally substituted alkyl, optionally substituted cycloalkyl, optionally substituted aralkyl, and optionally substituted heteroaryl, wherein one of Z is

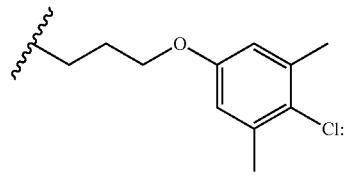

TABLE 1

| Compound # | A | L | R$^1$ |
|---|---|---|---|
| J1002 | 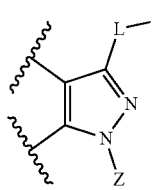 | —C(O)O— | H |
| 1008 | 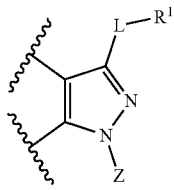 | —C(O)NHSO$_2$— | 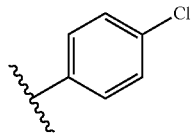 [SMILES: *c1ccc(Cl)cc1] |

TABLE 1-continued

| Compound # | A | L | R¹ |
|---|---|---|---|
| 1014 | pyrazole(A-L-R¹, N-Z) | —C(O)NHSO₂— | 4-morpholino-3-nitrophenyl |
| 1020 | pyrazole(A-L-R¹, N-Z) | —C(O)NHSO₂— | 3-nitro-4-((pyridin-3-ylmethyl)amino)phenyl |
| 1026 | pyrazole(A-L-R¹, N-Z) | —C(O)NHSO₂— | 4-((2-morpholinoethyl)amino)-3-nitrophenyl |
| 1032 | pyrazole(A-L-R¹, N-Z) | —C(O)NHSO₂— | 4-((furan-2-ylmethyl)amino)-3-nitrophenyl |
| 1038 | pyrazole(A-L-R¹, N-Z) | —C(O)NHSO₂— | 3-morpholino-4-nitrophenyl |
| 1044 | pyrazole(A-L-R¹, N-Z) | —C(O)NHSO₂— | 4-nitro-3-((pyridin-3-ylmethyl)amino)phenyl |
| 1050 | pyrazole(A-L-R¹, N-Z) | —C(O)NHSO₂— | 3-((furan-2-ylmethyl)amino)-4-nitrophenyl |
| 1056 | pyrazole(A-L-R¹, N-Z) | —C(O)NHSO₂— | 3-((2-morpholinoethyl)amino)-4-nitrophenyl |

TABLE 1-continued

| Compound # | A | L | R¹ |
|---|---|---|---|
| 1062 | pyrazole (L-R¹ at 3, Z at N1, attachments at 4,5) | —C(O)NHSO₂— | 4-(4-ethylpiperazin-1-yl)-3-nitrophenyl |
| 1068 | pyrazole (L-R¹ at 3, Z at N1, attachments at 4,5) | —C(O)NHSO₂— | 4-(benzamido)phenyl |
| 1074 | pyrazole (L-R¹ at 3, Z at N1, attachments at 4,5) | —C(O)NHSO₂— | 4-((furan-2-yl)amino)-3-nitrophenyl |
| 1080 | pyrazole (L-R¹ at 3, Z at N1, attachments at 4,5) | —C(O)NHSO₂— | 4-(((tetrahydrofuran-2-yl)methyl)amino)-3-nitrophenyl |
| 1086 | pyrazole (L-R¹ at 3, Z at N1, attachments at 4,5) | —C(O)NHSO₂— | 3-nitro-4-(piperazin-1-yl)phenyl |
| 1092 | pyrazole (L-R¹ at 3, Z at N1, attachments at 4,5) | —C(O)NHSO₂— | 4-(methylamino)-3-nitrophenyl |
| 1098 | pyrrole (N-Z, L-R¹ at 2, attachments at 3,4) | —C(O)NHSO₂— | 4-chlorophenyl |
| 1099 | pyrrole (N-Z, L-R¹ at 2, attachments at 3,4) | —C(O)NHSO₂— | 4-morpholino-3-nitrophenyl |

TABLE 1-continued

| Compound # | A | L | R¹ |
|---|---|---|---|
| 1100 | pyrrole(Z,Z,N-L-R¹) | —C(O)NHSO₂— | 4-(NH-CH₂-(pyridin-3-yl))-3-nitrophenyl |
| 1101 | pyrrole(Z,Z,N-L-R¹) | —C(O)NHSO₂— | 4-(NH-CH₂CH₂-morpholin-4-yl)-3-nitrophenyl |
| 1102 | pyrrole(Z,Z,N-L-R¹) | —C(O)NHSO₂— | 4-(NH-CH₂-(furan-2-yl))-3-nitrophenyl |
| 1103 | pyrrole(Z,Z,N-L-R¹) | —C(O)NHSO₂— | 3-(morpholin-4-yl)-4-nitrophenyl |
| 1104 | pyrrole(Z,Z,N-L-R¹) | —C(O)NHSO₂— | 3-(NH-CH₂-(pyridin-3-yl))-4-nitrophenyl |
| 1105 | pyrrole(Z,Z,N-L-R¹) | —C(O)NHSO₂— | 3-(NH-CH₂-(furan-2-yl))-4-nitrophenyl |
| 1106 | pyrrole(Z,Z,N-L-R¹) | —C(O)NHSO₂— | 3-(NH-CH₂CH₂-morpholin-4-yl)-4-nitrophenyl |
| 1107 | pyrrole(Z,Z,N-L-R¹) | —C(O)NHSO₂— | 3-(4-ethylpiperazin-1-yl)-4-nitrophenyl |

TABLE 1-continued

| Compound # | A | L | R¹ |
|---|---|---|---|
| 1108 | pyrrole (N-Z, with Z substituents) | —C(O)NHSO₂— | 4-(benzoylamino)phenyl |
| 1109 | pyrrole (N-Z, with Z substituents) | —C(O)NHSO₂— | 3-nitro-4-(furan-2-ylamino)phenyl |
| 1110 | pyrrole (N-Z, with Z substituents) | —C(O)NHSO₂— | 3-nitro-4-((tetrahydrofuran-2-ylmethyl)amino)phenyl |
| 1111 | pyrrole (N-Z, with Z substituents) | —C(O)NHSO₂— | 3-nitro-4-(piperazin-1-yl)phenyl |
| 1112 | pyrrole (N-Z, with Z substituents) | —C(O)NHSO₂— | 3-nitro-4-(methylamino)phenyl |
| 1114 | pyrazole (N-Z) | —C(O)O— | —CH₃ |
| 1119 | pyrrole (N-Z, with Z substituents) | —C(O)O— | —CH₃. |

* * * * *